United States Patent [19]

Keene et al.

[11] Patent Number: 5,525,495

[45] Date of Patent: Jun. 11, 1996

[54] METHODS AND COMPOSITIONS USEFUL IN THE RECOGNITION, BINDING AND EXPRESSION OF RIBONUCLEIC ACIDS INVOLVED IN CELL GROWTH, NEOPLASIA AND IMMUNOREGULATION

[75] Inventors: Jack D. Keene, Durham, N.C.; Todd Levine, St. Louis, Mo.; FenBiao Gao, Durham, N.C.

[73] Assignee: Duke University, Durham, N.C.

[21] Appl. No.: 120,827

[22] Filed: Sep. 15, 1993

Related U.S. Application Data

[63] Continuation-in-part of Ser. No. 881,075, May 11, 1992, Pat. No. 5,444,149.

[51] Int. Cl.[6] .............................. C12N 15/00; C07K 14/00
[52] U.S. Cl. ..................... 435/172.3; 435/172.1; 935/19; 935/22; 935/77; 935/80; 530/350; 530/300
[58] Field of Search ........................... 536/23.5; 530/350; 435/172.3

[56] References Cited

PUBLICATIONS

Tsai et al. VAR 19(18):4931, 1991.
Starr et al. Cell 46:659, 1986.
Tuerh et al. Science 249:505, 1990.
Levine et al. Mol Cell Biol 13(6):3494, 1993.

*Primary Examiner*—Suzanne E. Ziska
*Attorney, Agent, or Firm*—Oblon, Spivak, McClelland, Maier & Neustadt

[57] ABSTRACT

Methods and compounds are described that allow partitioning of messenger RNAs encoding runctionally related proteins, in particular those involved in cellular growth and differentiation, based upon binding to target sequences in the untranslated portions of the RNAs. The preparation of mRNA-subset libraries containing genes encoding such growth regulatory factors is described together with novel gene sequences derived useing these mRNA partitioning methods. These methods of mRNA partitioning allow access to growth regulatory factors unique to a given cell, tissue or tumor and provide a method of fingerprinting such factors.

7 Claims, 21 Drawing Sheets

| | | | | | | |
|---|---|---|---|---|---|---|
| ELAV | M D F I M A N T | - - - - - - - | - - - - - - - | G A G G G V D T Q A Q L M Q S A A A A A A A A V A A T N A A A | 37 |
| Hel-N1 | M - E - - T - - | - - - - - - - | - - Q L S - - | - - - - - - - - - - - N G P - T C N N - T - - A - - | 15 |
| K3(rbp9) | M V E G Q T A V Q Q Q Q Q Q P S G A G G A S G V G S T T G S A G G P A T A N N V T N S Q A | 45 |
| | | | | | | |
| ELAV | A P V Q N A A A V A A A Q L Q Q Q V Q Q A I L Q V Q Q Q T Q Q A V A A A A A A A V T Q | 82 |
| Hel-N1 | - N G P T - - - | - - - - - - - | - - - - - - - | - - T I N - - - - - - N N C S S - - P V D S G N T - - | 34 |
| K3(rbp9) | Q T N G G T T A T T T A A A G A G S T T N A A V G Q A T A N N A A S N N N N N N N T N N | 90 |
| | | | | | | |
| ELAV | Q L Q Q Q Q Q A V V A Q Q A V Q Q A A A A V V Q Q A A A A V V Q Q A V V P Q P Q Q A Q P | 127 |
| Hel-N1 | - - - - - - - | - - E - D S - - | - - - - - - - | - - - - - - - - - - - - - - - - - - - - - - - - - | 37 |
| K3(rbp9) | N N N N T A N N N N N E P D P - - - - - - - - - - - - - - - - - - - - - - - - - - | 108 |
| | | | | | | |
| ELAV | N T N G N A G S G S Q N G S N G S T E T R T N L I V N Y L P Q T M T E D E I R S L F S S V | 172 |
| Hel-N1 | - - - - - - - | - - - - - - - | - - - - - - - | - - K T N L - - - - N M T Q E E L K S L F G S I - - | 62 |
| K3(rbp9) | - - - - - - - | - - - - - - - | - - - - - - - | - - K T N L I V N Y L P Q T M S Q D E I R S L F V S F | 133 |

*FIG. 1A*

```
ELAV     GEIESVKLIRDKSQVYIDPLNPQAPSKGQSLGYGFVNYVRPQDAE  217
Hel-N1   GEIESCKLVRDKIT---------GQSLGYGFVNYIDPKDAE         15
K3(rbp9) GEVESCKLIRDKVT---------GQSLGYGFVNYVKQEDAE         45

ELAV     QAVNVLNGLRLQNKTIKVSFARPSSDAIKGANLYVSGLPKTMTQQ     262
Hel-N1   KAINTLNGLRLQTKTIKVSYARPSSASIRDANLYVSGLPKTMTQK     139
K3(rbp9) KAINALNGLRLQNKTIKVSIARPSSESIKGANLYVSGLPKNMTQS     210

ELAV     ELEAIFAPFGAIITSRILQNAGND---TQTKGVGFIRFDKREEA      303
Hel-N1   ELEQLFSQYGRIITSRILVDQVT---GISRGVGFIRFDKRIEA      179
K3(rbp9) DLESLFSPYGKIITSRILCDNITDEHAAGLSKGVGFIRFDQRFEA    255

ELAV     TRAIIALNGTTPSSCTDPIVVKFSNTPGSTSKIIQPQLPAFLNPQ    348
Hel-N1   EEAIKGLNGQKPPGATEPITVKFANNPSQKTNQAILSQLYQSP-N    223
K3(rbp9) DRAIKELNGTTPKNSTEPITVKFANNPSSNKNSMQPLAAYIAPQN    300
```

FIG. 1B

| | | |
|---|---|---|
| ELAV | LVRRIGGAMHTPVNKGLARFSPMAGDMLDVMLPNGLGAAAATT | 393 |
| Hel-N1 | ----R---YP------GPLAQQAQRFRLDNLLNMAYGVKRFSPMTIDG | 259 |
| K3(rbp9) | TRGGRAFPANAAGAAAAAAAIHPNAGRYSSVISRYSPLTSDL | 345 |

| | | |
|---|---|---|
| ELAV | LASGPGGAYP------IFIYNLAPETEEAALWQLFGPFGAVQS | 430 |
| Hel-N1 | MTSLAGINIPGHPGTGWC IFVYNLAPDADESILWQMFGPFGAVTN | 304 |
| K3(rbp9) | IT-NGMIQGNTIASSGWC IFVYNLAPETEENVLWQLFGPFGAVQS | 389 |

| | | |
|---|---|---|
| ELAV | VKIVKDPTTNQC KGYGFVSMTNYDEAAMAIRALNGYTMGNRVLQV | 475 |
| Hel-N1 | VKVIRDFNTNKC KGFVTMTNYDEAAMAIRSLNGYRLGDRVLQV | 349 |
| K3(rbp9) | VKVIRDLQSNKC KFGFVTMTNYEEAVLAIQSLNGYTLGNRVLQV | 434 |

| | | |
|---|---|---|
| ELAV | SFKTNK-AK-- | 483 |
| Hel-N1 | SFKTNKTHKA- | 359 |
| K3(rbp9) | SFKTNK-NKQT | 444 |

HEL-N1 SELECTED SEQUENCES

| | |
|---|---|
| B-14 | UCCAGUAACCCCACCUCCUUUUU |
| C-14 | UCAGUAAACGUGUAAACCUUUUAA |
| B-7  | UCAUAGCACCACCUCCUUUUUA |
| C-3  | UCAUAGCACCACCCACCCUUUUUA |
| A-6  | GGGCUAGGCUUAUCUCCUUUCC |
| B-13 | AUCAUAAAUUCAGUCGUCAUUUUCU |
| C-6  | UUAUUUAUUGCGUCUCCUUUAUUA |
| C-4  | AACUACCGGAGUACAGAUUUUUUA |
| A-4  | UCAGUGGCAUCCUUUCUUUACUUU |
| B-20 | CACAAACCUAACUUUCAUUUGCUUU |
| C-2  | UGACCGAUACAUUCAUUUAUUUA |
| B-18 | AUUGACUUCGUUAUUGUUUUAUUG |

*FIG. 3A*

B-3    AGACGCAAUUA AUGAUUUGUUUUUA
C-7    UAGCUCGGACA UUUAUUUUAUUU
C-7'   UUAGG UUUCUUUUAUUUGAGCAUA
B-19   A AUUCUCAUUAACGUCUCUCCUUU
A-1    ACACC UUUUUAGUUCCUGUAUUU
B-1    CUAAUUUCCGAUAUAAAGCUUAUUA
B-4    AUGAUUUAGAUUUCGCACAUUUCA
C-9    UACUUUCGGUACUAAAAUCGAUCAG
B-12   UCCUUUUUGUACCACUCUCAGUUGU

*FIG. 3B*

```
C-6R   UUAUUAUUGCGUCUCCUUUAUUA
B-10   UUAUUUAUUUGCGUCUCCUUUAUUA
C-5    UUUGUUUCGUGUAACGCAUAUACU
A-7    UUUAGUUUUAAUAGGAUAAAUACUUA
B-9    UUUGUUUCGUGUAACGCAUAUACU
B-15   UUGAUUUUCGGCCCCGCCCUUAG
```

*FIG. 3C*

| SELECTED HEL-N1 RNA-BINDING SEQUENCES | FOUND IN mRNA INSTABILITY REGIONS |
|---|---|
| AUUUA | GM-CSF, α-β-γ IFN, IL1-2-3, c-myc, c-myb |
| UAUUUAU | TNF, c-IFN, GM-CSF |
| AUUUUA | βIFN, c-myb, c-fos, IgG1-IF, IL-2 |
| AUUUUA | βIFN, c-myc, IL-2, c-fos, c-myb |
| AUUUC | βIFN |
| GUUUUA | c-myc, c-fos |
| CUUUUA | βIFN, c-myc |
| AUUUUUUC | c-myc |
| AUUUG | c-myb, c-myc |
| AUUUC | c-sis |
| CUUUA | c-sis |
| CUUUA | IL-2 |

FIG. 4

```
CCAATAGTAGTCATTTAAAATATATATTCTGAAATCTTTG CAAATTTAACAGAAGAGTCGAAGCTCTGCCGAGACCCAAT ATTTGCCAATAAGAGAATGGTTATGATAATTAGCACCATGGA
                                                                                                   M  V  M  I  I  S  T  M  E )

GCCTCAGGTGTCAAATGGTCCGACATCCAATACAAGCAAT GGACCCTCCAGCAACAACAGAAACTGTCCTTCTCCCATGC AAACAGGGGCAACCACAGATGACAGCAAAACCAACCTCAT
 P  Q  V  S  N  G  P  T  S  N  T  S  N    G  P  S  S  N  N  R  N  C  P  S  P  M    Q  T  G  A  T  T  D  D  S  K  T  N  L  I )

CGTCAACTATTTACCCCAGAATATGACCCAAGAAGAATTC AGGAGTCTCTTCGGAGCATTGGTGAAATAGAATCCTGCA AACTTGTGAGAGACAAAATTACAGGACAGAGTTTAGGGTA
 V  N  Y  L  P  Q  N  M  T  Q  E  E  F    R  S  L  F  G  S  I  G  E  I  E  S  C    K  L  V  R  D  K  I  T  G  G  S  L  G  Y )

TGGATTTGTTAACTATATTGATCCAAAGGATGCAGAGAAA GCCATCAACACTTTAAATGGACTCAGACTCCAGACCAAAA CCATAAAGGTCTCATATATGCCGTCCGAGCTCTGCCTCAAT
 G  F  V  N  Y  I  D  P  K  D  A  E  K    A  I  N  T  L  N  G  L  R  L  Q  T  K    T  I  K  V  S  Y  A  R  P  S  S  A  S  I )

CAGGGATGCTAACCTCTATGTTAGCGGCCTTCCCAAAACC ATGACCCAGAAGGAACTGGAGCAACTTTCTCGCAATACG GCCGTATCATCACCTCACGAATCTGGTTGATCAAGTCAC
 R  D  A  N  L  Y  V  S  G  L  P  K  T    M  T  Q  K  B  L  B  Q  L  F  S  Q  Y    G  R  I  I  T  S  R  I  L  V  D  Q  V  T )
```

FIG. 6A

```
                                                                                                                    720
         640                                    680                                                                  *
          *                                      *
AGGAGTGTCCAGAGGGGTGGATTCATCCGCTTTGATAAG AGGATTGAGGCAGAAGAAGCCATCAAAGGGCTGAATGGCC AGAAGCCCAGGGTGCTACGGAACCGATTACTGTGAAGTT
 G  V  S  R  G  V  G  F  I  R  F  D  K   R  I  E  A  E  E  A  I  K  G  L  N  G   Q  K  P  S  G  A  T  E  P  I  T  V  K  P >

840
         760                                    800                                                                  *
          *                                      *
TGCCAACAACCCCAGCCAGAAGTCCAGCCAGGCCCTGCTC TCCCAGCTCTACCAGTCCCCTAACCGGCGCTACCAGGTC CACTTCACCACCAGGTTCAGGTTCAGGCTGACAATTT
 A  N  N  P  S  Q  K  S  S  Q  A  L  L   S  Q  L  Y  Q  S  P  N  R  R  Y  P  G   P  L  N  N  Q  R  F  L  D  N  L >

960
         880                                    920                                                                  *
          *                                      *
GCTTAATATGGCCTATGGCGTAAAGAGACTGATGTCTGGA CCAGTCCCCCCTTCTGCTTGTTCCCCAGGTTCTCCCCAA TTACCATTGATGGAATGACAAGCCTTGTGGGAATGAACAT
 L  N  M  A  Y  G  V  K  R  L  M  S  G   P  V  P  P  S  A  C  S  P  R  F  S  P   I  T  I  D  G  M  T  S  L  V  G  M  N  I >

1080
        1000                                   1040                                                                  *
          *                                      *
CCCTGGTCACACAGGAACTGGGTGGTGCATCTTTGTCTAC AACCTGTCCCCCGATTCCGATGAGAGTGTCCTCTGGCAGC TCTTTGGCCCCTTTGGAGCAGTGAACAACGTAAAGGTGAT
 P  G  H  T  G  T  G  W  C  I  F  V  Y   N  L  S  P  D  S  D  E  S  V  L  W  Q   L  F  G  P  F  G  A  V  N  N  V  K  V  I >
```

*FIG. 6B*

```
                                                              1120                                 1160                                                     1200
                                                                *                                   *                                                       *
TCGTGACTTCAACACCAACAAGTGCAAGGATTCGGCTTT GTCACCATGACCAACTATGATGAGGCGGCCATGGCCATCG CCAGCCTCAACGGTACCGCCTGGGAGACAGAGTGTTGCA
 R  D  F  N  T  N  K  C  K  G  P  G  F   V  T  M  T  N  Y  D  E  A  A  M  A  I    A  S  L  N  G  Y  R  R  L  G  D  R  V  L  Q>

1240                                      1280                                  1320
                    *                                         *                                     *
AGTTCCTTTAAAACCAACAAGCCCACAAGTCCTGAATT TCCCATTCTTACTACTAAAATATATATAGAAATATATAC GAACAAAACACACGCGCACACACACATACACGAAAG
 V  S  F  K  T  N  K  A  N  K  S>

1360                                  1400                                             1440
              *                                     *                                               *
AGAGAGAAACAAACTTTTCAAGGCTTATATTCAACCATGG ACTTTATAAGCCAGTGTTGCCTAGTATTAAAACATTGGGT TATCCTGAGGTGTACCAGGAAAGGATTATAATGCTTAGAA

*
AAAAAAAAAAGAAAAAAAAAAAACAAAAAA
```

FIG. 6C

ΔHel-N1 SELECTED RNA SEQUENCES

| | |
|---|---|
| e-1 | AU<u>UUUAUUUA</u>CAUUCGUUUCAUUAU |
| e-2 | AU<u>UUUAUUUAG</u>UUUAGCCACCGUUUAU |
| e-3 | UUCCACCAUAAACUG<u>UUUUAUUUA</u>CGUU |
| e-4 | AGCGUAUUG<u>UUUUAUUUA</u>AAUUUUUG |
| e-5 | CGAACCCGGAUCUUUG<u>UUUUAUUG</u>AGUU |
| e-6 | CGUAUUUUAUUG<u>UUUUAUUUG</u>AAGUU |
| e-7 | AU<u>UUUUAGUUAG</u>CGCUUUUCGAAUUUG |
| e-8 | AU<u>UUAUAUAG</u>UUUUUUUAAUUUCG |
| e-9 | AU<u>UUAUUUUG</u>AUUUUAAGUAUGUAUCUU |
| e-10 | AU<u>UUAUUUUA</u>UGUUCUCGAUUCUA |
| e-11 | AU<u>UUAUUUUUA</u>UUUUUCUUAAGUUACUC |
| e-12 | AU<u>UUAUAC</u>UUUUUACACACAUUAUUGC |
| e-13 | AUUUACUUCGUAU<u>UUUUAUUUA</u>AAAG |
| e-14 | AGAGUUGCCAAAAU<u>CUUAUAUUUUUUUG</u>GUU |
| e-15 | AACCCAUCCAU<u>UUUAUUUUU</u>CUUUCGUUGUUG |
| e-16 | ACGUUCUACUCCAA<u>UUUG</u>AUUUUAGUU |
| e-17 | AUUUGUUUUUUG<u>UUUUU</u>CAUUUUAGUCC |
| e-18 | GUCCCAAAUCAGUUUUU<u>C</u>UUUUAUUGUU |
| e-19 | ACACCCAG<u>UUUUG</u>UUUUUUAAGUU |
| e-20 | AUUAUUA<u>UUUUG</u>UAUUGUUUUUUAAAUC |

Hel-N1 SELECTED RNA SEQUENCES

| | |
|---|---|
| H-1 | AU<u>UUCCG</u>UUUUGCCACUUUCUUUUC |
| H-2 | CCCCAAUUUUAUUG<u>U</u>UUCAUUUUAA |
| H-3 | AGUCAG<u>UUUUAUUUUA</u>GGCCUUCC |
| H-4 | AUUUUUAA<u>UUUUAAUUUUA</u>GCAGUA |
| H-5 | GAAUGGC<u>AUUUAUUUUG</u>ACGAA |
| H-6 | AU<u>UUAC</u>UUUAGACACUUUAAUUUG |

CONSENSUS SEQUENCE:  $\begin{smallmatrix} AU & & UA \\ GA \end{smallmatrix} UUUAUUU \begin{smallmatrix} UA \\ AG \end{smallmatrix}$

*FIG. 11*

SEQUENCE LISTING ( 1 ) GENERAL INFORMATION:

( i i i ) NUMBER OF SEQUENCES: 101

( 2 ) INFORMATION FOR SEQ ID NO:1:

( i ) SEQUENCE CHARACTERISTICS:
        ( A ) LENGTH: 485 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:1:

```
Asp  Cys  Met  Asp  Phe  Ile  Met  Ala  Asn  Thr  Gly  Ala  Gly  Gly  Gly  Val
 1              5                         10                         15

Asp  Thr  Gln  Ala  Gln  Leu  Met  Gln  Ser  Ala  Ala  Ala  Ala  Ala  Ala  Val
              20                        25                        30

Ala  Ala  Thr  Asn  Ala  Ala  Ala  Ala  Pro  Val  Gln  Asn  Ala  Ala  Ala  Val
              35                        40                        45

Ala  Ala  Ala  Ala  Gln  Leu  Gln  Gln  Gln  Gln  Val  Gln  Gln  Ala  Ile e  Leu
         50                        55                        60

Gln  Val  Gln  Gln  Gln  Gln  Thr  Gln  Gln  Ala  Val  Ala  Ala  Ala  Ala  Ala
65                             70                        75                        80

Ala  Val  Thr  Gln  Gln  Leu  Gln  Gln  Gln  Gln  Gln  Ala  Val  Val  Ala  Gln
                        85                        90                        95

Gln  Ala  Val  Val  Gln  Gln  Gln  Gln  Gln  Gln  Ala  Ala  Ala  Val  Val  Gln
                   100                       105                       110
```

```
Gln  Ala  Ala  Val  Gln  Gln  Ala  Val  Val  Pro  Gln  Pro  Gln  Gln  Ala  Gln
          115                 120                      125

Pro  Asn  Thr  Asn  Gly  Asn  Ala  Gly  Ser  Gly  Ser  Gln  Asn  Gly  Ser  Asn
          130                 135                      140

Gly  Ser  Thr  Glu  Thr  Arg  Thr  Asn  Leu  Ile  Val  Asn  Tyr  Leu  Pro  Gln
145                      150                      155                      160

Thr  Met  Thr  Glu  Asp  Glu  Ile  Arg  Ser  Leu  Phe  Ser  Ser  Val  Gly  Glu
               165                      170                      175

Ile  Glu  Ser  Val  Lys  Leu  Ile  Arg  Asp  Lys  Ser  Gln  Val  Tyr  Ile  Asp
               180                 185                      190

Pro  Leu  Asn  Pro  Gln  Ala  Pro  Ser  Lys  Gly  Gln  Ser  Leu  Gly  Xaa  Gly
          195                 200                      205

Phe  Val  Xaa  Tyr  Val  Arg  Pro  Gln  Asp  Ala  Glu  Gln  Ala  Val  Asn  Val
          210                 215                      220

Leu  Asn  Gly  Leu  Arg  Leu  Gln  Asn  Lys  Thr  Ile  Lys  Val  Ser  Phe  Ala
225                      230                 235                          240

Arg  Pro  Ser  Ser  Asp  Ala  Ile  Lys  Gly  Ala  Asn  Leu  Tyr  Val  Ser  Gly
               245                      250                      255

Leu  Pro  Lys  Thr  Met  Thr  Gln  Gln  Glu  Leu  Glu  Ala  Ile  Phe  Ala  Pro
               260                      265                      270

Phe  Gly  Ala  Ile  Ile  Thr  Ser  Arg  Ile  Leu  Gln  Asn  Ala  Gly  Asn  Asp
          275                      280                 285

Thr  Gln  Thr  Lys  Gly  Val  Gly  Phe  Ile  Arg  Phe  Asp  Lys  Arg  Glu  Glu
     290                      295                 300

Ala  Thr  Arg  Ala  Ile  Ile  Ala  Leu  Asn  Gly  Thr  Thr  Pro  Ser  Ser  Cys
305                      310                      315                      320

Thr  Asp  Pro  Ile  Val  Val  Lys  Phe  Ser  Asn  Thr  Pro  Gly  Ser  Thr  Ser
               325                      330                      335

Lys  Ile  Ile  Gln  Pro  Gln  Leu  Pro  Ala  Phe  Leu  Asn  Pro  Gln  Leu  Val
          340                      345                      350

Arg  Arg  Ile  Gly  Gly  Ala  Met  His  Thr  Pro  Val  Asn  Lys  Gly  Leu  Ala
          355                      360                      365

Arg  Phe  Ser  Pro  Met  Ala  Gly  Asp  Met  Leu  Asp  Val  Met  Leu  Pro  Asn
     370                      375                      380

Gly  Leu  Gly  Ala  Ala  Ala  Ala  Ala  Thr  Thr  Leu  Ala  Ser  Gly  Pro
385                      390                      395                      400

Gly  Gly  Ala  Tyr  Pro  Ile  Phe  Ile  Tyr  Asn  Leu  Ala  Pro  Glu  Thr  Glu
               405                      410                      415

Glu  Ala  Ala  Leu  Trp  Gln  Leu  Phe  Gly  Pro  Phe  Gly  Ala  Val  Gln  Ser
               420                      425                      430

Val  Lys  Ile  Val  Lys  Asp  Pro  Thr  Thr  Asn  Gln  Cys  Lys  Gly  Tyr  Gly
          435                      440                      445

Phe  Val  Ser  Met  Thr  Asn  Tyr  Asp  Glu  Ala  Ala  Met  Ala  Ile  Arg  Ala
     450                      455                      460

Leu  Asn  Gly  Tyr  Thr  Met  Gly  Asn  Arg  Val  Leu  Gln  Val  Ser  Phe  Lys
465                      470                      475                      480

Thr  Asn  Lys  Ala  Lys
               485
```

( 2 ) INFORMATION FOR SEQ ID NO:2:

( i ) SEQUENCE CHARACTERISTICS:
        ( A ) LENGTH: 359 amino acids
        ( B ) TYPE: amino acid
        ( D ) TOPOLOGY: unknown (ii) MOLECULE TYPE: protein (xi) SEQUENCE DESCRIPTION: SEQ ID NO:2:

```
Met Glu Thr Gln Leu Ser Asn Gly Pro Thr Cys Asn Asn Thr Ala Asn
 1               5                  10                  15
Gly Pro Thr Thr Ile Asn Asn Asn Cys Ser Ser Pro Val Asp Ser Gly
            20                  25                  30
Asn Thr Glu Asp Ser Lys Thr Asn Leu Ile Val Asn Tyr Leu Pro Gln
        35                  40                  45
Asn Met Thr Gln Glu Glu Leu Lys Ser Leu Phe Gly Ser Ile Gly Glu
    50                  55                  60
Ile Glu Ser Cys Lys Leu Val Arg Asp Lys Ile Thr Gly Gln Ser Leu
65                  70                  75                  80
Gly Tyr Gly Phe Val Xaa Tyr Ile Asp Pro Lys Asp Ala Glu Lys Ala
                85                  90                  95
Ile Asn Thr Leu Asn Gly Leu Arg Leu Gln Thr Lys Thr Ile Lys Val
            100                 105                 110
Ser Tyr Ala Arg Pro Ser Ser Ala Ser Ile Arg Asp Ala Asn Leu Tyr
        115                 120                 125
Val Ser Gly Leu Pro Lys Thr Met Thr Gln Lys Glu Leu Glu Gln Leu
    130                 135                 140
Phe Ser Gln Tyr Gly Arg Ile Ile Thr Ser Arg Ile Leu Val Asp Gln
145                 150                 155                 160
Val Thr Gly Ile Ser Arg Gly Val Gly Phe Ile Arg Phe Asp Lys Arg
                165                 170                 175
Ile Glu Ala Glu Glu Ala Ile Lys Gly Leu Asn Gly Gln Lys Pro Pro
            180                 185                 190
Gly Ala Thr Glu Pro Ile Thr Val Lys Phe Ala Asn Asn Pro Ser Gln
        195                 200                 205
Lys Thr Asn Gln Ala Ile Leu Ser Gln Leu Tyr Gln Ser Pro Asn Arg
    210                 215                 220
Arg Tyr Pro Gly Pro Leu Ala Gln Gln Ala Gln Arg Phe Arg Leu Asp
225                 230                 235                 240
Asn Leu Leu Asn Met Ala Tyr Gly Val Lys Arg Phe Ser Pro Met Thr
                245                 250                 255
Ile Asp Gly Met Thr Ser Leu Ala Gly Ile Asn Ile Pro Gly His Pro
            260                 265                 270
Gly Thr Gly Trp Cys Ile Phe Val Tyr Asn Leu Ala Pro Asp Ala Asp
        275                 280                 285
Glu Ser Ile Leu Trp Gln Met Phe Gly Pro Phe Gly Ala Val Thr Asn
    290                 295                 300
Val Lys Val Ile Arg Asp Phe Asn Thr Asn Lys Cys Lys Gly Phe Gly
305                 310                 315                 320
Phe Val Thr Met Thr Asn Tyr Asp Glu Ala Ala Met Ala Ile Arg Ser
                325                 330                 335
Leu Asn Gly Tyr Arg Leu Gly Asp Arg Val Leu Gln Val Ser Phe Lys
            340                 345                 350
Thr Asn Lys Thr His Lys Ala
        355
```

(2) INFORMATION FOR SEQ ID NO:3:

(i) SEQUENCE CHARACTERISTICS:
        (A) LENGTH: 444 amino acids
        (B) TYPE: amino acid
        (D) TOPOLOGY: unknown ( i i ) MOLECULE TYPE: protein ( x i ) SEQUENCE DESCRIPTION: SEQ ID NO:3:

| Met | Val | Glu | Gly | Gln | Thr | Ala | Val | Gln | Gln | Gln | Gln | Gln | Pro | Ser |
| 1 | | | | 5 | | | | | 10 | | | | | 15 |

| Gly | Ala | Gly | Gly | Ala | Ser | Gly | Val | Gly | Ser | Thr | Thr | Gly | Ser | Ala | Gly |
| | | | 20 | | | | | 25 | | | | | 30 | | |

| Gly | Pro | Ala | Thr | Ala | Asn | Asn | Val | Thr | Asn | Ser | Gln | Ala | Gln | Thr | Asn |
| | | | 35 | | | | 40 | | | | | 45 | | | |

| Gly | Gly | Thr | Thr | Ala | Thr | Thr | Thr | Ala | Ala | Ala | Gly | Ala | Gly | Ser | Thr |
| | 50 | | | | | 55 | | | | | 60 | | | | |

| Thr | Asn | Ala | Ala | Val | Gly | Gln | Ala | Thr | Ala | Asn | Ala | Ala | Ser | Asn |
| 65 | | | | | 70 | | | | 75 | | | | | 80 |

| Asn | Asn | Asn | Asn | Asn | Asn | Thr | Asn | Asn | Asn | Asn | Asn | Asn | Ala |
| | | | | 85 | | | | | 90 | | | | | 95 |

| Thr | Ala | Asn | Asn | Asn | Asn | Asn | Asn | Glu | Pro | Asp | Pro | Lys | Thr | Asn | Leu |
| | | | 100 | | | | | 105 | | | | | 110 | | |

| Ile | Val | Asn | Tyr | Leu | Pro | Gln | Thr | Met | Ser | Gln | Asp | Glu | Ile | Arg | Ser |
| | | 115 | | | | | 120 | | | | | 125 | | | |

| Leu | Phe | Val | Ser | Phe | Gly | Glu | Val | Glu | Ser | Cys | Lys | Leu | Ile | Arg | Asp |
| | 130 | | | | | 135 | | | | | 140 | | | | |

| Lys | Val | Thr | Gly | Gln | Ser | Leu | Gly | Tyr | Gly | Phe | Val | Xaa | Tyr | Val | Lys |
| 145 | | | | | 150 | | | | | 155 | | | | | 160 |

| Gln | Glu | Asp | Ala | Glu | Lys | Ala | Ile | Asn | Ala | Leu | Asn | Gly | Leu | Arg | Leu |
| | | | | 165 | | | | | 170 | | | | | 175 | |

| Gln | Asn | Lys | Thr | Ile | Lys | Val | Ser | Ile | Ala | Arg | Pro | Ser | Ser | Glu | Ser |
| | | | 180 | | | | | 185 | | | | | 190 | | |

| Ile | Lys | Gly | Ala | Asn | Leu | Tyr | Val | Ser | Gly | Leu | Pro | Lys | Asn | Met | Thr |
| | | 195 | | | | | 200 | | | | | 205 | | | |

| Gln | Ser | Asp | Leu | Glu | Ser | Leu | Phe | Ser | Pro | Tyr | Gly | Lys | Ile | Ile | Thr |
| | 210 | | | | | 215 | | | | | 220 | | | | |

| Ser | Arg | Ile | Leu | Cys | Asp | Asn | Ile | Thr | Asp | Glu | His | Ala | Ala | Gly | Leu |
| 225 | | | | | 230 | | | | | 235 | | | | | 240 |

| Ser | Lys | Gly | Val | Gly | Phe | Ile | Arg | Phe | Asp | Gln | Arg | Phe | Glu | Ala | Asp |
| | | | | 245 | | | | | 250 | | | | | 255 | |

| Arg | Ala | Ile | Lys | Glu | Leu | Asn | Gly | Thr | Thr | Pro | Lys | Asn | Ser | Thr | Glu |
| | | | 260 | | | | | 265 | | | | | 270 | | |

| Pro | Ile | Thr | Val | Lys | Phe | Ala | Asn | Asn | Pro | Ser | Ser | Asn | Lys | Asn | Ser |
| | | 275 | | | | | 280 | | | | | 285 | | | |

| Met | Gln | Pro | Leu | Ala | Ala | Tyr | Ile | Ala | Pro | Gln | Asn | Thr | Arg | Gly | Gly |
| | 290 | | | | | 295 | | | | | 300 | | | | |

| Arg | Ala | Phe | Pro | Ala | Asn | Ala | Ala | Ala | Gly | Ala | Ala | Ala | Ala | Ala | Ala |
| 305 | | | | | 310 | | | | | 315 | | | | | 320 |

| Ala | Ala | Ala | Ile | His | Pro | Asn | Ala | Gly | Arg | Tyr | Ser | Ser | Val | Ile | Ser |
| | | | | 325 | | | | | 330 | | | | | 335 | |

| Arg | Tyr | Ser | Pro | Leu | Thr | Ser | Asp | Leu | Ile | Thr | Asn | Gly | Met | Ile | Gln |
| | | | 340 | | | | | 345 | | | | | 350 | | |

| Gly | Asn | Thr | Ile | Ala | Ser | Ser | Gly | Trp | Cys | Ile | Phe | Val | Tyr | Asn | Leu |
| | | 355 | | | | | 360 | | | | | 365 | | | |

| Ala | Pro | Glu | Thr | Glu | Glu | Asn | Val | Leu | Trp | Gln | Leu | Phe | Gly | Pro | Phe |
| | 370 | | | | | 375 | | | | | 380 | | | | |

| Gly | Ala | Val | Gln | Ser | Val | Lys | Val | Ile | Arg | Asp | Leu | Gln | Ser | Asn | Lys |
| 385 | | | | | 390 | | | | | 395 | | | | | 400 |

```
            Cys    Lys    Gly    Phe    Gly    Phe    Val    Thr    Met    Thr    Asn    Tyr    Glu    Glu    Ala    Val
                                        405                         410                         415

Leu    Ala    Ile    Gln    Ser    Leu    Asn    Gly    Tyr    Thr    Leu    Gly    Asn    Arg    Val    Leu
                                 420                         425                         430

Gln    Val    Ser    Phe    Lys    Thr    Asn    Lys    Asn    Lys    Gln    Thr
                          435                         440
```

( 2 ) INFORMATION FOR SEQ ID NO:4:

( i ) SEQUENCE CHARACTERISTICS:
        ( A ) LENGTH: 76 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:4:

```
    Val    Ile    His    Ile    Arg    Lys    Leu    Pro    Ile    Asp    Val    Thr    Glu    Gly    Glu    Val
    1                          5                                  10                                 15

Ile    Ser    Leu    Gly    Leu    Pro    Phe    Gly    Lys    Val    Thr    Asn    Leu    Leu    Met    Leu
                         20                                 25                                 30

Lys    Gly    Lys    Asn    Gln    Ala    Phe    Ile    Glu    Met    Asn    Thr    Glu    Glu    Ala    Ala
                         35                                 40                                 45

Asn    Thr    Met    Val    Asn    Tyr    Tyr    Thr    Ser    Val    Thr    Pro    Val    Leu    Arg    Gly
                  50                                 55                                 60

Gln    Pro    Ile    Tyr    Ile    Gln    Phe    Ser    Asn    His    Lys    Glu
    65                                 70                                 75
```

( 2 ) INFORMATION FOR SEQ ID NO:5:

( i ) SEQUENCE CHARACTERISTICS:
        ( A ) LENGTH: 78 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:5:

```
    Arg    Ile    Ile    Val    Glu    Asn    Leu    Phe    Tyr    Pro    Val    Thr    Leu    Asp    Val    Leu
    1                          5                                  10                                 15

Met    Gln    Ile    Phe    Ser    Lys    Phe    Gly    Thr    Val    Leu    Lys    Ile    Ile    Thr    Phe
                         20                                 25                                 30

Thr    Lys    Asn    Asn    Gln    Phe    Gln    Ala    Leu    Leu    Gln    Tyr    Ala    Asp    Pro    Val
                         35                                 40                                 45

Ser    Ala    Gln    His    Ala    Lys    Leu    Ser    Leu    Asp    Gly    Gln    Asn    Ile    Tyr    Asn
                  50                                 55                                 60

Ala    Cys    Cys    Thr    Leu    Arg    Ile    Asp    Phe    Ser    Lys    Leu    Thr    Ser
    65                                 70                                 75
```

( 2 ) INFORMATION FOR SEQ ID NO:6:

( i ) SEQUENCE CHARACTERISTICS:
        ( A ) LENGTH: 76 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

```
    Val    Leu    Leu    Val    Ser    Asn    Leu    Asn    Pro    Glu    Arg    Val    Thr    Pro    Gln    Ser
    1                          5                                  10                                 15

Leu    Phe    Ile    Leu    Phe    Gly    Val    Tyr    Gly    Asp    Val    Gln    Arg    Val    Lys    Ile
                         20                                 25                                 30
```

```
        Leu  Phe  Asn  Lys  Lys  Glu  Asn  Ala  Leu  Val  Gln  Met  Ala  Asp  Gly  Asn
                       35                  40                       45

Gln  Ala  Gln  Leu  Ala  Met  Ser  His  Leu  Asn  Gly  His  Lys  Leu  His  Gly
                  50                       55                       60

Lys  Pro  Ile  Arg  Ile  Thr  Leu  Ser  Lys  His  Gln  Asn
        65                            70                       75
```

( 2 ) INFORMATION FOR SEQ ID NO:7:

( i ) SEQUENCE CHARACTERISTICS:
        ( A ) LENGTH: 76 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:7:

```
        Val  Val  His  Ile  Arg  Gly  Leu  Ile  Asp  Gly  Val  Val  Glu  Ala  Asp  Leu
        1                   5                        10                       15

Val  Glu  Ala  Leu  Gln  Glu  Phe  Gly  Pro  Ile  Ser  Tyr  Val  Val  Val  Met
                       20                       25                       30

Pro  Lys  Lys  Arg  Gln  Ala  Leu  Val  Glu  Phe  Glu  Asp  Val  Leu  Gly  Ala
                       35                       40                       45

Cys  Asn  Ala  Val  Asn  Tyr  Ala  Ala  Asp  Asn  Gln  Ile  Tyr  Ile  Ala  Gly
                  50                       55                       60

His  Pro  Ala  Phe  Val  Asn  Tyr  Ser  Thr  Ser  Gln  Lys
        65                       70                       75
```

( 2 ) INFORMATION FOR SEQ ID NO:8:

( i ) SEQUENCE CHARACTERISTICS:
        ( A ) LENGTH: 77 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:8:

```
        Leu  Phe  Thr  Ile  Leu  Asn  Pro  Ile  Tyr  Ser  Ile  Thr  Thr  Asp  Val  Leu
        1                   5                        10                       15

Tyr  Thr  Ile  Cys  Asn  Pro  Cys  Gly  Pro  Val  Gln  Arg  Ile  Val  Ile  Phe
                       20                       25                       30

Arg  Lys  Asn  Gly  Val  Gln  Ala  Met  Val  Glu  Phe  Asp  Ser  Val  Gln  Ser
                       35                       40                       45

Ala  Gln  Arg  Ala  Lys  Ala  Ser  Leu  Asn  Gly  Ala  Asp  Ile  Tyr  Ser  Gly
                  50                       55                       60

Cys  Cys  Thr  Leu  Lys  Ile  Glu  Tyr  Ala  Lys  Pro  Thr  Arg
        65                       70                       75
```

( 2 ) INFORMATION FOR SEQ ID NO:9:

( i ) SEQUENCE CHARACTERISTICS:
        ( A ) LENGTH: 76 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:9:

```
        Val  Leu  Met  Val  Tyr  Gly  Leu  Asp  Gln  Ser  Lys  Met  Asn  Gly  Asp  Arg
        1                   5                        10                       15

Val  Phe  Asn  Val  Phe  Cys  Leu  Tyr  Gly  Asn  Val  Glu  Lys  Val  Lys  Phe
```

|       |       |       | 20    |       |       | 25    |       |       | 30    |       |       |       |
|-------|-------|-------|-------|-------|-------|-------|-------|-------|-------|-------|-------|-------|
| Met   | Lys   | Ser   | Lys   | Pro   | Gly   | Ala   | Ala   | Met   | Val   | Glu   | Met   | Ala   | Asp   | Gly   | Tyr   |
|       |       | 35    |       |       |       | 40    |       |       |       | 45    |       |       |
| Ala   | Val   | Asp   | Arg   | Ala   | Ile   | Thr   | His   | Leu   | Asn   | Asn   | Asn   | Phe   | Met   | Phe   | Gly   |
|       |       | 50    |       |       |       | 55    |       |       |       | 60    |       |       |
| Gln   | Lys   | Leu   | Asn   | Val   | Cys   | Val   | Ser   | Lys   | Gln   | Pro   | Ala   |
| 65    |       |       |       |       | 70    |       |       |       |       | 75    |       |

( 2 ) INFORMATION FOR SEQ ID NO:10:

( i ) SEQUENCE CHARACTERISTICS:
        ( A ) LENGTH: 80 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:10:

| Asn | Leu | Ile | Val | Xaa | Leu | Pro | Gln | Asp | Met | Thr | Asp | Arg | Glu | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Tyr | Ala | Leu | Phe | Arg | Ala | Ile | Gly | Pro | Ile | Asn | Thr | Cys | Arg | Ile | Met |
|     |     |     | 20  |     |     |     |     | 25  |     |     |     |     | 30  |     |
| Arg | Asp | Tyr | Lys | Thr | Gly | Tyr | Ser | Phe | Gly | Tyr | Ala | Phe | Val | Asp | Phe |
|     |     | 35  |     |     |     |     | 40  |     |     |     |     | 45  |     |     |
| Thr | Ser | Glu | Met | Asp | Ser | Gln | Arg | Ala | Ile | Lys | Val | Leu | Asn | Gly | Ile |
|     |     | 50  |     |     |     | 55  |     |     |     |     | 60  |     |     |     |     |
| Thr | Val | Arg | Asn | Lys | Arg | Leu | Lys | Val | Ser | Tyr | Ala | Arg | Pro | Gly | Gly |
| 65  |     |     |     |     | 70  |     |     |     |     | 75  |     |     |     |     | 80  |

( 2 ) INFORMATION FOR SEQ ID NO:11:

( i ) SEQUENCE CHARACTERISTICS:
        ( A ) LENGTH: 82 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:11:

| Asn | Leu | Tyr | Val | Thr | Asn | Leu | Pro | Arg | Thr | Ile | Thr | Asp | Asp | Gln | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asp | Thr | Ile | Phe | Gly | Lys | Tyr | Gly | Ser | Ile | Val | Gln | Lys | Asn | Ile | Leu |
|     |     |     | 20  |     |     |     |     | 25  |     |     |     |     | 30  |     |     |
| Arg | Asp | Lys | Leu | Thr | Gly | Arg | Pro | Arg | Gly | Val | Ala | Phe | Val | Arg | Tyr |
|     |     | 35  |     |     |     |     | 40  |     |     |     |     | 45  |     |     |     |
| Asn | Lys | Arg | Glu | Glu | Ala | Gln | Glu | Ala | Ile | Ser | Ala | Leu | Asn | Asn | Val |
|     | 50  |     |     |     |     | 55  |     |     |     |     | 60  |     |     |     |     |
| Ile | Pro | Glu | Gly | Gly | Ser | Gln | Pro | Leu | Ser | Val | Arg | Leu | Ala | Glu | Glu |
| 65  |     |     |     |     | 70  |     |     |     |     | 75  |     |     |     |     | 80  |
| His | Gly |

( 2 ) INFORMATION FOR SEQ ID NO:12:

( i ) SEQUENCE CHARACTERISTICS:
        ( A ) LENGTH: 75 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:12:

| Lys | Val | Tyr | Val | Gly | Asn | Leu | Gly | Ser | Ser | Ala | Ser | Lys | His | Glu | Ile |
|-----|-----|-----|-----|-----|-----|-----|-----|-----|-----|-----|-----|-----|-----|-----|-----|

```
     1               5                    10                       15
Glu  Gly  Ala  Phe  Ala  Lys  Tyr  Gly  Pro  Leu  Arg  Asn  Val  Trp  Val  Ala
               20                      25                      30

Arg  Asn  Pro  Pro  Gly  Phe  Ala  Phe  Val  Glu  Phe  Glu  Asp  Arg  Arg  Asp
               35                      40                      45

Ala  Glu  Asp  Ala  Thr  Arg  Ala  Leu  Asp  Gly  Thr  Arg  Cys  Cys  Gly  Thr
          50                      55                      60

Arg  Ile  Arg  Val  Glu  Met  Ser  Ser  Gly  Arg  Ser
65                       70                      75
```

( 2 ) INFORMATION FOR SEQ ID NO:13:

( i ) SEQUENCE CHARACTERISTICS:
        ( A ) LENGTH: 81 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:13:

```
Ile  Ala  Phe  Val  Gly  Asn  Leu  Pro  Gln  Gly  Leu  Val  Gln  Gly  Asp  Val
1                   5                       10                      15

Ile  Lys  Ile  Phe  Gln  Asp  Phe  Glu  Val  Lys  Tyr  Val  Arg  Leu  Val  Lys
               20                      25                      30

Asp  Arg  Glu  Thr  Asp  Gln  Phe  Lys  Gly  Phe  Cys  Tyr  Val  Glu  Phe  Glu
               35                      40                      45

Thr  Leu  Asp  Asn  Leu  Glu  Arg  Ala  Leu  Glu  Cys  Asp  Gly  Arg  Ile  Lys
          50                      55                      60

Leu  Asp  Asp  Leu  Ser  Ala  Pro  Leu  Arg  Ile  Asp  Ile  Ala  Asp  Arg  Arg
65                       70                      75                      80

Lys
```

( 2 ) INFORMATION FOR SEQ ID NO:14:

( i ) SEQUENCE CHARACTERISTICS:
        ( A ) LENGTH: 93 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:14:

```
Asn  Leu  Ile  Val  Asn  Tyr  Leu  Pro  Gln  Thr  Met  Thr  Glu  Asp  Glu  Ile
1                   5                       10                      15

Arg  Ser  Leu  Phe  Ser  Ser  Val  Gly  Glu  Ile  Glu  Ser  Val  Lys  Leu  Ile
               20                      25                      30

Arg  Asp  Lys  Ser  Gln  Val  Tyr  Ile  Asp  Pro  Leu  Asn  Pro  Gln  Ala  Pro
               35                      40                      45

Ser  Lys  Gly  Gln  Ser  Leu  Gly  Tyr  Gly  Phe  Val  Asn  Tyr  Val  Arg  Pro
          50                      55                      60

Gln  Asp  Ala  Glu  Gln  Ala  Val  Asn  Val  Leu  Asn  Gly  Leu  Arg  Leu  Gln
65                       70                      75                      80

Asn  Lys  Thr  Ile  Lys  Val  Ser  Phe  Ala  Arg  Pro  Ser  Ser
               85                      90
```

( 2 ) INFORMATION FOR SEQ ID NO:15:

( i ) SEQUENCE CHARACTERISTICS:
        ( A ) LENGTH: 80 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:15:

| Asn | Leu | Ile | Val | Asn | Tyr | Leu | Pro | Gln | Thr | Met | Ser | Gln | Asp | Glu | Ile |
|---|---|---|---|---|---|---|---|---|---|---|---|---|---|---|---|
| 1 | | | | 5 | | | | | 10 | | | | | 15 | |

| Arg | Ser | Leu | Phe | Val | Ser | Phe | Gly | Val | Glu | Ser | Cys | Lys | Leu | Ile |
|---|---|---|---|---|---|---|---|---|---|---|---|---|---|---|
| | | | 20 | | | | 25 | | | | 30 | | | |

| Arg | Asp | Lys | Val | Thr | Gly | Gln | Ser | Leu | Gly | Tyr | Gly | Phe | Val | Asn | Tyr |
|---|---|---|---|---|---|---|---|---|---|---|---|---|---|---|---|
| | | 35 | | | | | 40 | | | | | 45 | | | |

| Val | Lys | Gln | Glu | Asp | Ala | Glu | Lys | Ala | Ile | Asn | Ala | Leu | Asn | Gly | Leu |
|---|---|---|---|---|---|---|---|---|---|---|---|---|---|---|---|
| | 50 | | | | | 55 | | | | | 60 | | | | |

| Arg | Leu | Gln | Asn | Lys | Thr | Ile | Lys | Val | Ser | Ile | Ala | Arg | Pro | Ser | Ser |
|---|---|---|---|---|---|---|---|---|---|---|---|---|---|---|---|
| 65 | | | | | 70 | | | | | 75 | | | | | 80 |

( 2 ) INFORMATION FOR SEQ ID NO:16:

( i ) SEQUENCE CHARACTERISTICS:
( A ) LENGTH: 80 amino acids
( B ) TYPE: amino acid
( D ) TOPOLOGY: unknown ( i i ) MOLECULE TYPE: peptide ( x i ) SEQUENCE DESCRIPTION: SEQ ID NO:16:

| Asn | Leu | Ile | Val | Asn | Tyr | Leu | Pro | Gln | Asn | Met | Thr | Gln | Glu | Glu | Leu |
|---|---|---|---|---|---|---|---|---|---|---|---|---|---|---|---|
| 1 | | | | 5 | | | | | 10 | | | | | 15 | |

| Lys | Ser | Leu | Phe | Gly | Ser | Ile | Gly | Glu | Ile | Glu | Ser | Cys | Lys | Leu | Val |
|---|---|---|---|---|---|---|---|---|---|---|---|---|---|---|---|
| | | | 20 | | | | 25 | | | | 30 | | | | |

| Arg | Asp | Lys | Ile | Thr | Gly | Gln | Ser | Leu | Gly | Tyr | Gly | Phe | Val | Asn | Tyr |
|---|---|---|---|---|---|---|---|---|---|---|---|---|---|---|---|
| | | 35 | | | | | 40 | | | | | 45 | | | |

| Ile | Asp | Pro | Lys | Asp | Ala | Glu | Lys | Ala | Ile | Asn | Thr | Leu | Asn | Gly | Leu |
|---|---|---|---|---|---|---|---|---|---|---|---|---|---|---|---|
| | 50 | | | | | 55 | | | | | 60 | | | | |

| Arg | Leu | Gln | Thr | Lys | Thr | Ile | Lys | Val | Ser | Tyr | Ala | Arg | Pro | Ser | Ser |
|---|---|---|---|---|---|---|---|---|---|---|---|---|---|---|---|
| 65 | | | | | 70 | | | | | 75 | | | | | 80 |

( 2 ) INFORMATION FOR SEQ ID NO:17:

( i ) SEQUENCE CHARACTERISTICS:
( A ) LENGTH: 83 amino acids
( B ) TYPE: amino acid
( D ) TOPOLOGY: unknown ( i i ) MOLECULE TYPE: peptide ( x i ) SEQUENCE DESCRIPTION: SEQ ID NO:17:

| Asn | Leu | Tyr | Val | Ser | Gly | Leu | Pro | Lys | Thr | Met | Thr | Gln | Gln | Glu | Leu |
|---|---|---|---|---|---|---|---|---|---|---|---|---|---|---|---|
| 1 | | | | 5 | | | | | 10 | | | | | 15 | |

| Glu | Ala | Ile | Phe | Ala | Pro | Phe | Gly | Ala | Ile | Ile | Thr | Ser | Arg | Ile | Leu |
|---|---|---|---|---|---|---|---|---|---|---|---|---|---|---|---|
| | | | 20 | | | | 25 | | | | 30 | | | | |

| Gln | Asn | Ala | Gly | Asn | Asp | Thr | Gln | Thr | Lys | Gly | Val | Gly | Phe | Ile | Arg |
|---|---|---|---|---|---|---|---|---|---|---|---|---|---|---|---|
| | | 35 | | | | | 40 | | | | | 45 | | | |

| Phe | Asp | Lys | Arg | Glu | Glu | Ala | Thr | Arg | Ala | Ile | Ile | Ala | Leu | Asn | Gly |
|---|---|---|---|---|---|---|---|---|---|---|---|---|---|---|---|
| | 50 | | | | | 55 | | | | | 60 | | | | |

| Thr | Thr | Pro | Ser | Ser | Cys | Thr | Asp | Pro | Ile | Val | Val | Lys | Phe | Ser | Asn |
|---|---|---|---|---|---|---|---|---|---|---|---|---|---|---|---|
| 65 | | | | | 70 | | | | | 75 | | | | | 80 |

| Thr | Pro | Gly |
|---|---|---|

( 2 ) INFORMATION FOR SEQ ID NO:18:

( i ) SEQUENCE CHARACTERISTICS:

(A) LENGTH: 87 amino acids
(B) TYPE: amino acid
(D) TOPOLOGY: unknown (ii) MOLECULE TYPE: peptide (xi) SEQUENCE DESCRIPTION: SEQ ID NO:18:

| Asn | Leu | Tyr | Val | Ser | Gly | Leu | Pro | Lys | Asn | Met | Thr | Gln | Ser | Asp | Leu |
| 1 | | | | 5 | | | | | 10 | | | | | 15 | |
| Glu | Ser | Leu | Phe | Ser | Pro | Tyr | Gly | Lys | Ile | Ile | Thr | Ser | Arg | Ile | Leu |
| | | | 20 | | | | | 25 | | | | | 30 | | |
| Cys | Asp | Asn | Ile | Thr | Asp | Glu | Asn | Ala | Ala | Gly | Leu | Ser | Lys | Gly | Val |
| | | 35 | | | | | 40 | | | | | 45 | | | |
| Gly | Phe | Ile | Arg | Phe | Asp | Gln | Arg | Phe | Glu | Ala | Asp | Arg | Ala | Ile | Lys |
| | | 50 | | | | 55 | | | | | 60 | | | | |
| Glu | Leu | Asn | Gly | Thr | Thr | Pro | Lys | Asn | Ser | Thr | Glu | Pro | Ile | Thr | Val |
| 65 | | | | | 70 | | | | | 75 | | | | | 80 |
| Lys | Phe | Ala | Asn | Asn | Pro | Ser | | | | | | | | | |
| | | | | 85 | | | | | | | | | | | |

(2) INFORMATION FOR SEQ ID NO:19:

(i) SEQUENCE CHARACTERISTICS:
(A) LENGTH: 82 amino acids
(B) TYPE: amino acid
(D) TOPOLOGY: unknown (ii) MOLECULE TYPE: peptide (xi) SEQUENCE DESCRIPTION: SEQ ID NO:19:

| Asn | Leu | Tyr | Val | Ser | Gly | Leu | Pro | Lys | Thr | Met | Thr | Gln | Lys | Glu | Leu |
| 1 | | | | 5 | | | | | 10 | | | | | 15 | |
| Glu | Gln | Leu | Phe | Ser | Gln | Tyr | Gly | Arg | Ile | Ile | Thr | Ser | Arg | Ile | Leu |
| | | | 20 | | | | | 25 | | | | | 30 | | |
| Val | Asp | Gln | Val | Thr | Gly | Ile | Ser | Arg | Gly | Val | Gly | Phe | Ile | Arg | Phe |
| | | | 35 | | | | | 40 | | | | | 45 | | |
| Asp | Lys | Arg | Ile | Glu | Ala | Glu | Glu | Ala | Ile | Lys | Gly | Leu | Asn | Gly | Gln |
| | 50 | | | | | 55 | | | | | 60 | | | | |
| Lys | Pro | Pro | Gly | Ala | Thr | Glu | Pro | Ile | Thr | Val | Lys | Phe | Ala | Asn | Asn |
| 65 | | | | | 70 | | | | | 75 | | | | | 80 |
| Pro | Ser | | | | | | | | | | | | | | |

(2) INFORMATION FOR SEQ ID NO:20:

(i) SEQUENCE CHARACTERISTICS:
(A) LENGTH: 80 amino acids
(B) TYPE: amino acid
(D) TOPOLOGY: unknown (ii) MOLECULE TYPE: peptide (xi) SEQUENCE DESCRIPTION: SEQ ID NO:20:

| Pro | Ile | Phe | Ile | Tyr | Asn | Leu | Ala | Pro | Glu | Thr | Glu | Glu | Ala | Ala | Leu |
| 1 | | | | 5 | | | | | 10 | | | | | 15 | |
| Trp | Gln | Leu | Phe | Gly | Pro | Phe | Gly | Ala | Val | Gln | Ser | Val | Lys | Ile | Val |
| | | | 20 | | | | | 25 | | | | | 30 | | |
| Lys | Asp | Pro | Thr | Thr | Asn | Gln | Cys | Lys | Gly | Tyr | Gly | Phe | Val | Ser | Met |
| | | 35 | | | | | 40 | | | | | 45 | | | |
| Thr | Asn | Tyr | Asp | Glu | Ala | Ala | Met | Ala | Ile | Arg | Ala | Leu | Asn | Gly | Tyr |
| | 50 | | | | | 55 | | | | | 60 | | | | |
| Thr | Met | Gly | Asn | Arg | Val | Leu | Gln | Val | Ser | Phe | Lys | Thr | Asn | Lys | Ala |

( 2 ) INFORMATION FOR SEQ ID NO:21:

( i ) SEQUENCE CHARACTERISTICS:
        ( A ) LENGTH: 80 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:21:

```
Cys Ile Phe Val Tyr Asn Leu Ala Pro Glu Thr Glu Glu Asn Val Leu
1               5                   10                  15
Trp Gln Leu Phe Gly Pro Phe Gly Ala Val Gln Ser Val Lys Val Ile
            20                  25                  30
Arg Asp Leu Gln Ser Asn Lys Cys Lys Gly Phe Gly Phe Val Thr Met
            35                  40                  45
Thr Asn Tyr Glu Glu Ala Val Leu Ala Ile Gln Ser Leu Asn Gly Tyr
        50                  55                  60
Thr Leu Gly Asn Arg Val Leu Gln Val Ser Phe Lys Thr Asn Lys Asn
65                  70                  75                  80
```

( 2 ) INFORMATION FOR SEQ ID NO:22:

( i ) SEQUENCE CHARACTERISTICS:
        ( A ) LENGTH: 80 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:22:

```
Cys Ile Phe Val Tyr Asn Leu Ala Pro Asp Ala Asp Glu Ser Ile Leu
1               5                   10                  15
Trp Gln Met Phe Gly Pro Phe Gly Ala Val Thr Asn Val Lys Val Ile
            20                  25                  30
Arg Asp Phe Asn Thr Asn Lys Cys Lys Gly Phe Gly Phe Val Thr Met
            35                  40                  45
Thr Asn Tyr Asp Glu Ala Ala Met Ala Ile Arg Ser Leu Asn Gly Tyr
        50                  55                  60
Arg Leu Gly Asp Arg Val Leu Gln Val Ser Phe Lys Thr Asn Lys Thr
65                  70                  75                  80
```

( 2 ) INFORMATION FOR SEQ ID NO:23:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:23:

UCCAGUAACC CCACCUCCUC UUUUU                            25

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown (i i) MOLECULE TYPE: RNA (genomic)

(x i) SEQUENCE DESCRIPTION: SEQ ID NO:24:

UCAGUUAAAC GUGUAAACCU UUUAA  25

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (i i) MOLECULE TYPE: RNA (genomic)

(x i) SEQUENCE DESCRIPTION: SEQ ID NO:25:

UCAUAGCACC ACCUCACCCU UUUUA  25

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (i i) MOLECULE TYPE: RNA (genomic)

(x i) SEQUENCE DESCRIPTION: SEQ ID NO:26:

UCAUAGCACC ACCUCACCCU UUUUA  25

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: unknown
        (D) TOPOLOGY: unknown (i i) MOLECULE TYPE: RNA (genomic)

(x i) SEQUENCE DESCRIPTION: SEQ ID NO:27:

GGGCUAGGCU UAUCCUCCUU UCC  23

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (i i) MOLECULE TYPE: RNA (genomic)

(x i) SEQUENCE DESCRIPTION: SEQ ID NO:28:

AUCAUAAAUU CAGUGUCAUU UUUCU  25

(2) INFORMATION FOR SEQ ID NO:29:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (i i) MOLECULE TYPE: RNA (genomic)

(x i) SEQUENCE DESCRIPTION: SEQ ID NO:29:

UUAUUUAUUU GCGUCUCCUU UAUUA  25

( 2 ) INFORMATION FOR SEQ ID NO:30:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:30:

AACUACCGGA GUACAGAUUU UUUUA 25

( 2 ) INFORMATION FOR SEQ ID NO:31:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:31:

UCAGUGGCAU CUCUUUCUUU ACUUU 25

( 2 ) INFORMATION FOR SEQ ID NO:32:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:32:

CACAACCCUA ACUUUCAUUU GCUUU 25

( 2 ) INFORMATION FOR SEQ ID NO:33:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:33:

UGACCGAUAC ACAUUCUUUU AUUUA 25

( 2 ) INFORMATION FOR SEQ ID NO:34:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:34:

AUUGACUUCG UUAUUGUUUU UAUUG 25

( 2 ) INFORMATION FOR SEQ ID NO:35:

( i ) SEQUENCE CHARACTERISTICS:

(A) LENGTH: 25 base pairs
(B) TYPE: nucleic acid
(C) STRANDEDNESS: unknown
(D) TOPOLOGY: unknown (ii) MOLECULE TYPE: RNA (genomic)

(xi) SEQUENCE DESCRIPTION: SEQ ID NO:35:

AGACGCAAUU AAUGAUUUGU UUUUA 25

(2) INFORMATION FOR SEQ ID NO:36:

(i) SEQUENCE CHARACTERISTICS:
(A) LENGTH: 24 base pairs
(B) TYPE: nucleic acid
(C) STRANDEDNESS: unknown
(D) TOPOLOGY: unknown (ii) MOLECULE TYPE: RNA (genomic)

(xi) SEQUENCE DESCRIPTION: SEQ ID NO:36:

UAGCUCGGAC AUUUAUUUUU AUUU 24

(2) INFORMATION FOR SEQ ID NO:37:

(i) SEQUENCE CHARACTERISTICS:
(A) LENGTH: 25 base pairs
(B) TYPE: nucleic acid
(C) STRANDEDNESS: unknown
(D) TOPOLOGY: unknown (ii) MOLECULE TYPE: RNA (genomic)

(xi) SEQUENCE DESCRIPTION: SEQ ID NO:37:

UUAGGUUUCU UUUUAUUUGA GCAUA 25

(2) INFORMATION FOR SEQ ID NO:38:

(i) SEQUENCE CHARACTERISTICS:
(A) LENGTH: 25 base pairs
(B) TYPE: nucleic acid
(C) STRANDEDNESS: unknown
(D) TOPOLOGY: unknown (ii) MOLECULE TYPE: RNA (genomic)

(xi) SEQUENCE DESCRIPTION: SEQ ID NO:38:

AUUUCUCAUU UAACGUCUCU CCUUU 25

(2) INFORMATION FOR SEQ ID NO:39:

(i) SEQUENCE CHARACTERISTICS:
(A) LENGTH: 24 base pairs
(B) TYPE: nucleic acid
(C) STRANDEDNESS: unknown
(D) TOPOLOGY: unknown (ii) MOLECULE TYPE: RNA (genomic)

(xi) SEQUENCE DESCRIPTION: SEQ ID NO:39:

ACACCCUUUU UAGUUCCUGU AUUU 24

(2) INFORMATION FOR SEQ ID NO:40:

(i) SEQUENCE CHARACTERISTICS:
(A) LENGTH: 26 base pairs
(B) TYPE: nucleic acid
(C) STRANDEDNESS: unknown
(D) TOPOLOGY: unknown ( i i ) MOLECULE TYPE: RNA (genomic)

( x i ) SEQUENCE DESCRIPTION: SEQ ID NO:40:

CUAAUUUCCG AUAUUAAAGC UUAUUA 26

( 2 ) INFORMATION FOR SEQ ID NO:41:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:41:

AUGAUUUAGA UUUUCGCACA UUUCA 25

( 2 ) INFORMATION FOR SEQ ID NO:42:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:42:

UACUUUCGGU ACUAAAAUCG AUCAG 25

( 2 ) INFORMATION FOR SEQ ID NO:43:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:43:

UCCUUUUUGU ACCACUCUCA GUUGU 25

( 2 ) INFORMATION FOR SEQ ID NO:44:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:44:

UUAUUUAUUU GCGUCUCCUU UAUUA 25

( 2 ) INFORMATION FOR SEQ ID NO:45:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:45:

UUAUUUAUUU GCGUCUCCUU UAUUA 25

( 2 ) INFORMATION FOR SEQ ID NO:46:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:46:

UUUGUUUCG UGUAACGCAU AUACU 25

( 2 ) INFORMATION FOR SEQ ID NO:47:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:47:

UUUAGUUUAA UAGGGAUAAU ACUUA 25

( 2 ) INFORMATION FOR SEQ ID NO:48:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:48:

UUUGUUUCG UGUAACGCAU AUACU 25

( 2 ) INFORMATION FOR SEQ ID NO:49:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:49:

UUGAUUUCG CGCCCGCCGC CUUAG 25

( 2 ) INFORMATION FOR SEQ ID NO:50:

( i ) SEQUENCE CHARACTERISTICS:
    ( A ) LENGTH: 1467 base pairs
    ( B ) TYPE: nucleic acid
    ( C ) STRANDEDNESS: unknown
    ( D ) TOPOLOGY: unknown ( i i ) MOLECULE TYPE: DNA (genomic)

( i x ) FEATURE:
    ( A ) NAME/KEY: CDS
    ( B ) LOCATION: 95..1234

( x i ) SEQUENCE DESCRIPTION: SEQ ID NO:50:

CCAATAGTAG TCATTTTAAA TATATATTCT GAAATCTTTG CAAATTTTAA CAGAAGAGTC 60

```
GAAGCTCTGC GAGACCCAAT ATTTGCCAAT AAGA ATG GTT ATG ATA ATT AGC          112
                                       Met Val Met Ile Ile Ser
                                        1               5

ACC ATG GAG CCT CAG GTG TCA AAT GGT CCG ACA TCC AAT ACA AGC AAT        160
Thr Met Glu Pro Gln Val Ser Asn Gly Pro Thr Ser Asn Thr Ser Asn
            10              15                  20

GGA CCC TCC AGC AAC AAC AGA AAC TGT CCT TCT CCC ATG CAA ACA GGG        208
Gly Pro Ser Ser Asn Asn Arg Asn Cys Pro Ser Pro Met Gln Thr Gly
            25              30              35

GCA ACC ACA GAT GAC AGC AAA ACC AAC CTC ATC GTC AAC TAT TTA CCC        256
Ala Thr Thr Asp Asp Ser Lys Thr Asn Leu Ile Val Asn Tyr Leu Pro
        40              45              50

CAG AAT ATG ACC CAA GAA GAA TTC AGG AGT CTC TTC GGG AGC ATT GGT        304
Gln Asn Met Thr Gln Glu Glu Phe Arg Ser Leu Phe Gly Ser Ile Gly
55              60              65                          70

GAA ATA GAA TCC TGC AAA CTT GTG AGA GAC AAA ATT ACA GGA CAG AGT        352
Glu Ile Glu Ser Cys Lys Leu Val Arg Asp Lys Ile Thr Gly Gln Ser
                75              80              85

TTA GGG TAT GGA TTT GTT AAC TAT ATT GAT CCA AAG GAT GCA GAG AAA        400
Leu Gly Tyr Gly Phe Val Asn Tyr Ile Asp Pro Lys Asp Ala Glu Lys
            90              95              100

GCC ATC AAC ACT TTA AAT GGA CTC AGA CTC CAG ACC AAA ACC ATA AAG        448
Ala Ile Asn Thr Leu Asn Gly Leu Arg Leu Gln Thr Lys Thr Ile Lys
            105             110             115

GTC TCA TAT GCC CGT CCG AGC TCT GCC TCA ATC AGG GAT GCT AAC CTC        496
Val Ser Tyr Ala Arg Pro Ser Ser Ala Ser Ile Arg Asp Ala Asn Leu
        120             125             130

TAT GTT AGC GGC CTT CCC AAA ACC ATG ACC CAG AAG GAA CTG GAG CAA        544
Tyr Val Ser Gly Leu Pro Lys Thr Met Thr Gln Lys Glu Leu Glu Gln
135             140             145             150

CTT TTC TCG CAA TAC GGC CGT ATC ATC ACC TCA CGA ATC CTG GTT GAT        592
Leu Phe Ser Gln Tyr Gly Arg Ile Ile Thr Ser Arg Ile Leu Val Asp
                155             160             165

CAA GTC ACA GGA GTG TCC AGA GGG GTG GGA TTC ATC CGC TTT GAT AAG        640
Gln Val Thr Gly Val Ser Arg Gly Val Gly Phe Ile Arg Phe Asp Lys
            170             175             180

AGG ATT GAG GCA GAA GAA GCC ATC AAA GGG CTG AAT GGC CAG AAG CCC        688
Arg Ile Glu Ala Glu Glu Ala Ile Lys Gly Leu Asn Gly Gln Lys Pro
            185             190             195

AGC GGT GCT ACG GAA CCG ATT ACT GTG AAG TTT GCC AAC AAC CCC AGC        736
Ser Gly Ala Thr Glu Pro Ile Thr Val Lys Phe Ala Asn Asn Pro Ser
200             205             210

CAG AAG TCC AGC CAG GCC CTG CTC TCC CAG CTC TAC CAG TCC CCT AAC        784
Gln Lys Ser Ser Gln Ala Leu Leu Ser Gln Leu Tyr Gln Ser Pro Asn
215             220             225             230

CGG CGC TAC CCA GGT CCA CTT CAC CAC CAG GCT CAG AGG TTC AGG CTG        832
Arg Arg Tyr Pro Gly Pro Leu His His Gln Ala Gln Arg Phe Arg Leu
            235             240             245

GAC AAT TTG CTT AAT ATG GCC TAT GGC GTA AAG AGA CTG ATG TCT GGA        880
Asp Asn Leu Leu Asn Met Ala Tyr Gly Val Lys Arg Leu Met Ser Gly
            250             255             260

CCA GTC CCC CCT TCT GCT TGT TCC CCC AGG TTC TCC CCA ATT ACC ATT        928
Pro Val Pro Pro Ser Ala Cys Ser Pro Arg Phe Ser Pro Ile Thr Ile
        265             270             275

GAT GGA ATG ACA AGC CTT GTG GGA ATG AAC ATC CCT GGT CAC ACA GGA        976
Asp Gly Met Thr Ser Leu Val Gly Met Asn Ile Pro Gly His Thr Gly
        280             285             290

ACT GGG TGG TGC ATC TTT GTC TAC AAC CTG TCC CCC GAT TCC GAT GAG       1024
Thr Gly Trp Cys Ile Phe Val Tyr Asn Leu Ser Pro Asp Ser Asp Glu
295             300             305             310
```

| | | | | | | | | | | | | | | | | |
|---|---|---|---|---|---|---|---|---|---|---|---|---|---|---|---|---|
| AGT | GTC | CTC | TGG | CAG | CTC | TTT | GGC | CCC | TTT | GGA | GCA | GTG | AAC | AAC | GTA | 1072 |
| Ser | Val | Leu | Trp | Gln | Leu | Phe | Gly | Pro | Phe | Gly | Ala | Val | Asn | Asn | Val | |
| | | | 315 | | | | 320 | | | | | 325 | | | | |
| AAG | GTG | ATT | CGT | GAC | TTC | AAC | ACC | AAC | AAG | TGC | AAG | GGA | TTC | GGC | TTT | 1120 |
| Lys | Val | Ile | Arg | Asp | Phe | Asn | Thr | Asn | Lys | Cys | Lys | Gly | Phe | Gly | Phe | |
| | | | 330 | | | | | 335 | | | | | 340 | | | |
| GTC | ACC | ATG | ACC | AAC | TAT | GAT | GAG | GCG | GCC | ATG | GCC | ATC | GCC | AGC | CTC | 1168 |
| Val | Thr | Met | Thr | Asn | Tyr | Asp | Glu | Ala | Ala | Met | Ala | Ile | Ala | Ser | Leu | |
| | | | 345 | | | | | 350 | | | | | 355 | | | |
| AAC | GGG | TAC | CGC | CTG | GGA | GAC | AGA | GTG | TTG | CAA | GTT | TCC | TTT | AAA | ACC | 1216 |
| Asn | Gly | Tyr | Arg | Leu | Gly | Asp | Arg | Val | Leu | Gln | Val | Ser | Phe | Lys | Thr | |
| | | | 360 | | | | | 365 | | | | | 370 | | | |
| AAC | AAA | GCC | CAC | AAG | TCC | TGAATTCCC | ATTCTTACTT | ACTAAAATAT | | | | | | | | 1264 |
| Asn | Lys | Ala | His | Lys | Ser | | | | | | | | | | | |
| 375 | | | | | 380 | | | | | | | | | | | |

ATATAGAAAT ATATACGAAC AAAACACACG CGCGCACACA CACATACACG AAAGAGAGAG 1324

AAACAAACTT TTCAAGGCTT ATATTCAACC ATGGACTTTA TAAGCCAGTG TTGCCTAGTA 1384

TTAAAACATT GGGTTATCCT GAGGTGTACC AGGAAAGGAT TATAATGCTT AGAAAAAAAA 1444

AAAGAAAAAA AAAAAACAAA AAA 1467

( 2 ) INFORMATION FOR SEQ ID NO:51:

( i ) SEQUENCE CHARACTERISTICS:
        ( A ) LENGTH: 380 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

| Met | Val | Met | Ile | Ile | Ser | Thr | Met | Glu | Pro | Gln | Val | Ser | Asn | Gly | Pro |
|---|---|---|---|---|---|---|---|---|---|---|---|---|---|---|---|
| 1 | | | | 5 | | | | | 10 | | | | | 15 | |
| Thr | Ser | Asn | Thr | Ser | Asn | Gly | Pro | Ser | Ser | Asn | Asn | Arg | Asn | Cys | Pro |
| | | | 20 | | | | | 25 | | | | | 30 | | |
| Ser | Pro | Met | Gln | Thr | Gly | Ala | Thr | Thr | Asp | Asp | Ser | Lys | Thr | Asn | Leu |
| | | | 35 | | | | | 40 | | | | | 45 | | |
| Ile | Val | Asn | Tyr | Leu | Pro | Gln | Asn | Met | Thr | Gln | Glu | Glu | Phe | Arg | Ser |
| | 50 | | | | | 55 | | | | | 60 | | | | |
| Leu | Phe | Gly | Ser | Ile | Gly | Glu | Ile | Glu | Ser | Cys | Lys | Leu | Val | Arg | Asp |
| 65 | | | | | 70 | | | | | 75 | | | | | 80 |
| Lys | Ile | Thr | Gly | Gln | Ser | Leu | Gly | Tyr | Gly | Phe | Val | Asn | Tyr | Ile | Asp |
| | | | | 85 | | | | | 90 | | | | | 95 | |
| Pro | Lys | Asp | Ala | Glu | Lys | Ala | Ile | Asn | Thr | Leu | Asn | Gly | Leu | Arg | Leu |
| | | | 100 | | | | | 105 | | | | | 110 | | |
| Gln | Thr | Lys | Thr | Ile | Lys | Val | Ser | Tyr | Ala | Arg | Pro | Ser | Ser | Ala | Ser |
| | | | 115 | | | | | 120 | | | | | 125 | | |
| Ile | Arg | Asp | Ala | Asn | Leu | Tyr | Val | Ser | Gly | Leu | Pro | Lys | Thr | Met | Thr |
| | | | 130 | | | | | 135 | | | | | 140 | | |
| Gln | Lys | Glu | Leu | Glu | Gln | Leu | Phe | Ser | Gln | Tyr | Gly | Arg | Ile | Ile | Thr |
| 145 | | | | | 150 | | | | | 155 | | | | | 160 |
| Ser | Arg | Ile | Leu | Val | Asp | Gln | Val | Thr | Gly | Val | Ser | Arg | Gly | Val | Gly |
| | | | | 165 | | | | | 170 | | | | | 175 | |
| Phe | Ile | Arg | Phe | Asp | Lys | Arg | Ile | Glu | Ala | Glu | Glu | Ala | Ile | Lys | Gly |
| | | | 180 | | | | | 185 | | | | | 190 | | |
| Leu | Asn | Gly | Gln | Lys | Pro | Ser | Gly | Ala | Thr | Glu | Pro | Ile | Thr | Val | Lys |
| | | | 195 | | | | | 200 | | | | | 205 | | |
| Phe | Ala | Asn | Asn | Pro | Ser | Gln | Lys | Ser | Ser | Gln | Ala | Leu | Leu | Ser | Gln |

|  | | | | 210 | | | | 215 | | | | 220 | | |
|---|---|---|---|---|---|---|---|---|---|---|---|---|---|---|

Leu Tyr Gln Ser Pro Asn Arg Tyr Pro Gly Pro Leu His His Gln
225                     230             235             240

Ala Gln Arg Phe Arg Leu Asp Asn Leu Leu Asn Met Ala Tyr Gly Val
                245             250             255

Lys Arg Leu Met Ser Gly Pro Val Pro Pro Ser Ala Cys Ser Pro Arg
            260             265             270

Phe Ser Pro Ile Thr Ile Asp Gly Met Thr Ser Leu Val Gly Met Asn
        275             280             285

Ile Pro Gly His Thr Gly Thr Gly Trp Cys Ile Phe Val Tyr Asn Leu
    290             295             300

Ser Pro Asp Ser Asp Glu Ser Val Leu Trp Gln Leu Phe Gly Pro Phe
305             310             315             320

Gly Ala Val Asn Asn Val Lys Val Ile Arg Asp Phe Asn Thr Asn Lys
                325             330             335

Cys Lys Gly Phe Gly Phe Val Thr Met Thr Asn Tyr Asp Glu Ala Ala
            340             345             350

Met Ala Ile Ala Ser Leu Asn Gly Tyr Arg Leu Gly Asp Arg Val Leu
            355             360             365

Gln Val Ser Phe Lys Thr Asn Lys Ala His Lys Ser
370             375             380

( 2 ) INFORMATION FOR SEQ ID NO:52:

( i ) SEQUENCE CHARACTERISTICS:
            ( A ) LENGTH: 57 base pairs
            ( B ) TYPE: nucleic acid
            ( C ) STRANDEDNESS: unknown
            ( D ) TOPOLOGY: unknown ( i i ) MOLECULE TYPE: DNA (genomic)

( i x ) FEATURE:
            ( A ) NAME/KEY: CDS
            ( B ) LOCATION: 1..57

( x i ) SEQUENCE DESCRIPTION: SEQ ID NO:52:

CGT TTT AGG TTG GAC AAT CTG CTC AAT ATG GCT TAT GGA GTA AAG AGG    48
Arg Phe Arg Leu Asp Asn Leu Leu Asn Met Ala Tyr Gly Val Lys Arg
  1               5                  10                  15

TTT TCT CCA                                                         57
Phe Ser Pro ( 2 ) INFORMATION FOR SEQ ID NO:53:

( i ) SEQUENCE CHARACTERISTICS:
            ( A ) LENGTH: 19 amino acids
            ( B ) TYPE: amino acid
            ( D ) TOPOLOGY: linear ( i i ) MOLECULE TYPE: protein ( x i ) SEQUENCE DESCRIPTION: SEQ ID NO:53:

Arg Phe Arg Leu Asp Asn Leu Leu Asn Met Ala Tyr Gly Val Lys Arg
  1               5                  10                  15

Phe Ser Pro ( 2 ) INFORMATION FOR SEQ ID NO:54:

( i ) SEQUENCE CHARACTERISTICS:
            ( A ) LENGTH: 25 base pairs
            ( B ) TYPE: nucleic acid
            ( C ) STRANDEDNESS: unknown (D) TOPOLOGY: unknown (ii) MOLECULE TYPE: RNA (genomic)

(xi) SEQUENCE DESCRIPTION: SEQ ID NO:54:

AUUUGAUUUA CAUUCGUUUC AUUAU  25

(2) INFORMATION FOR SEQ ID NO:55:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:55:

AUUUUAUUUA GUUUAGCCAC CGUUUAU  27

(2) INFORMATION FOR SEQ ID NO:56:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:56:

UUCCACCAUA AACUGUUUUA UUUACGUU  28

(2) INFORMATION FOR SEQ ID NO:57:

(i) SEQUENCE CHARACTERISTICS:
        (A) LENGTH: 26 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:57:

AGCGUAUUGU UUUAUUUAAA UUUUUG  26

(2) INFORMATION FOR SEQ ID NO:58:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:58:

CGAACCCGGA UCUUUGUUUU AUUGAGUU  28

(2) INFORMATION FOR SEQ ID NO:59:

(i) SEQUENCE CHARACTERISTICS:
        (A) LENGTH: 26 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:59:

CGUAUUUUAU UGUUUUAUUU GAAGUU                                    26

( 2 ) INFORMATION FOR SEQ ID NO:60:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:60:

AUUUUAGUUA GCGCUUUUCG AAUUUG                                    26

( 2 ) INFORMATION FOR SEQ ID NO:61:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:61:

AUUUAUAUAG UUUUUUUUAA UUUCG                                     25

( 2 ) INFORMATION FOR SEQ ID NO:62:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:62:

AUUUAUUUUG AUUUUAAGUA UGUAUCUU                                  28

( 2 ) INFORMATION FOR SEQ ID NO:63:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:63:

AUUUAUUUUA UGUUCUCGAU UCUA                                      24

( 2 ) INFORMATION FOR SEQ ID NO:64:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:64:

AUUUAUUUUU AUUUUUCUUA AGUUACUC                                  28

( 2 ) INFORMATION FOR SEQ ID NO:65:

( i ) SEQUENCE CHARACTERISTICS:
: ( A ) LENGTH: 26 base pairs
: ( B ) TYPE: nucleic acid
: ( C ) STRANDEDNESS: unknown
: ( D ) TOPOLOGY: unknown ( i i ) MOLECULE TYPE: RNA (genomic)

( x i ) SEQUENCE DESCRIPTION: SEQ ID NO:65:

AUUAUACUUU UUACACACAU UAUUGC 26

( 2 ) INFORMATION FOR SEQ ID NO:66:

( i ) SEQUENCE CHARACTERISTICS:
: ( A ) LENGTH: 27 base pairs
: ( B ) TYPE: nucleic acid
: ( C ) STRANDEDNESS: unknown
: ( D ) TOPOLOGY: unknown ( i i ) MOLECULE TYPE: RNA (genomic)

( x i ) SEQUENCE DESCRIPTION: SEQ ID NO:66:

AUUUACUUUC GUAUUUUUAU UUUAAAG 27

( 2 ) INFORMATION FOR SEQ ID NO:67:

( i ) SEQUENCE CHARACTERISTICS:
: ( A ) LENGTH: 31 base pairs
: ( B ) TYPE: nucleic acid
: ( C ) STRANDEDNESS: unknown
: ( D ) TOPOLOGY: unknown ( i i ) MOLECULE TYPE: RNA (genomic)

( x i ) SEQUENCE DESCRIPTION: SEQ ID NO:67:

AGAGUUGCCA AAAUCUUAUA UUUUUUUGGU U 31

( 2 ) INFORMATION FOR SEQ ID NO:68:

( i ) SEQUENCE CHARACTERISTICS:
: ( A ) LENGTH: 32 base pairs
: ( B ) TYPE: nucleic acid
: ( C ) STRANDEDNESS: unknown
: ( D ) TOPOLOGY: unknown ( i i ) MOLECULE TYPE: RNA (genomic)

( x i ) SEQUENCE DESCRIPTION: SEQ ID NO:68:

AACCCAUCCA UUUUAUUUUU CUUUCGUUGU UG 32

( 2 ) INFORMATION FOR SEQ ID NO:69:

( i ) SEQUENCE CHARACTERISTICS:
: ( A ) LENGTH: 28 base pairs
: ( B ) TYPE: nucleic acid
: ( C ) STRANDEDNESS: unknown
: ( D ) TOPOLOGY: unknown ( i i ) MOLECULE TYPE: RNA (genomic)

( x i ) SEQUENCE DESCRIPTION: SEQ ID NO:69:

ACGUUCUACU CCUAAUUUGA UUUUAGUU 28

( 2 ) INFORMATION FOR SEQ ID NO:70:

( i ) SEQUENCE CHARACTERISTICS:
: ( A ) LENGTH: 28 base pairs
: ( B ) TYPE: nucleic acid
: ( C ) STRANDEDNESS: unknown (D) TOPOLOGY: unknown (ii) MOLECULE TYPE: RNA (genomic)

(xi) SEQUENCE DESCRIPTION: SEQ ID NO:70:

AUUUGUUUUU UGUUUUUCAU UUUAGUCC 28

(2) INFORMATION FOR SEQ ID NO:71:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:71:

GUCCCAAAUC AGUUUUUCUU UUAUUGUU 28

(2) INFORMATION FOR SEQ ID NO:72:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:72:

ACACCCUAGU UUUGUUUUUU AAGUU 25

(2) INFORMATION FOR SEQ ID NO:73:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:73:

AUUAUUAUUU UGUAUUGUUU UUUAAAUC 28

(2) INFORMATION FOR SEQ ID NO:74:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:74:

AUUUCCGUUU UGCCACUUUC UUUUC 25

(2) INFORMATION FOR SEQ ID NO:75:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:75:

CCCCAUUUU AUUGUUUCAU UUUAA 25

( 2 ) INFORMATION FOR SEQ ID NO:76:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:76:

AGUCAGUUUU AUUUUAGGCC UUCC 24

( 2 ) INFORMATION FOR SEQ ID NO:77:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:77:

AUUUUUAAUU UUAAUUUUAG CUGUA 25

( 2 ) INFORMATION FOR SEQ ID NO:78:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:78:

GAAUGGCAUU UAUUUUGACG AA 22

( 2 ) INFORMATION FOR SEQ ID NO:79:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:79:

AUUUACUUUA GACACUUUAA UUUG 24

( 2 ) INFORMATION FOR SEQ ID NO:80:

( i ) SEQUENCE CHARACTERISTICS:
        ( A ) LENGTH: 11 base pairs
        ( B ) TYPE: nucleic acid
        ( C ) STRANDEDNESS: unknown
        ( D ) TOPOLOGY: linear ( i i ) MOLECULE TYPE: RNA (genomic)

( x i ) SEQUENCE DESCRIPTION: SEQ ID NO:80:

RWUUUAUUUW R 11

( 2 ) INFORMATION FOR SEQ ID NO:81:

( i ) SEQUENCE CHARACTERISTICS:
   ( A ) LENGTH: 109 base pairs
   ( B ) TYPE: nucleic acid
   ( C ) STRANDEDNESS: unknown
   ( D ) TOPOLOGY: unknown ( i i ) MOLECULE TYPE: cDNA ( x i ) SEQUENCE DESCRIPTION: SEQ ID NO:81:

```
CCGTTCCATG AGCCACTCAA TATCCTTCCA AATAATTTTT TTCTAAGTTA ACCATTCTTT        60
TGTTTTTCTA AGTTAACCAT TCTTTTGTTG TTTGAAAAAA AAAAAAAA                    109
```

( 2 ) INFORMATION FOR SEQ ID NO:82:

( i ) SEQUENCE CHARACTERISTICS:
      ( A ) LENGTH: 109 base pairs
      ( B ) TYPE: nucleic acid
      ( C ) STRANDEDNESS: unknown
      ( D ) TOPOLOGY: unknown ( i i ) MOLECULE TYPE: cDNA ( x i ) SEQUENCE DESCRIPTION: SEQ ID NO:82:

```
GGTAGGCAAA AAAAGATATC GCAGGAAGGC CCTCCGTGAT TCACTTCATA TGTTTATGTA        60
TTGGTTGAAT TATTTTTGTA ATTTTAAAAA AAAAAAAAAA AAAAAAAA                    109
```

( 2 ) INFORMATION FOR SEQ ID NO:83:

( i ) SEQUENCE CHARACTERISTICS:
      ( A ) LENGTH: 110 base pairs
      ( B ) TYPE: nucleic acid
      ( C ) STRANDEDNESS: unknown
      ( D ) TOPOLOGY: unknown ( i i ) MOLECULE TYPE: cDNA ( x i ) SEQUENCE DESCRIPTION: SEQ ID NO:83:

```
ACTGTTTTCC CACCAGCCTG TTGGCGAAGT TGCTGCTCCG GCATTCAGTA CCTGCTTCTT        60
CCTGTGAAAT AAAGTTAGTT TCTATTTTAT GTTAAAAAAA AAAAAAAAA                   110
```

( 2 ) INFORMATION FOR SEQ ID NO:84:

( i ) SEQUENCE CHARACTERISTICS:
      ( A ) LENGTH: 109 base pairs
      ( B ) TYPE: nucleic acid
      ( C ) STRANDEDNESS: unknown
      ( D ) TOPOLOGY: unknown ( i i ) MOLECULE TYPE: cDNA ( x i ) SEQUENCE DESCRIPTION: SEQ ID NO:84:

```
CATGTTTTCC CACCAGCCTG TTGGCGAAGT TGCTGCTCCG GCATTCAGTA CCTGCTTCTT        60
CCTGTGAAAT AAAGTTAGTT TCTATTTTAT GTTAAAAAAA AAAAAAAA                    109
```

( 2 ) INFORMATION FOR SEQ ID NO:85:

( i ) SEQUENCE CHARACTERISTICS:
      ( A ) LENGTH: 57 base pairs
      ( B ) TYPE: nucleic acid
      ( C ) STRANDEDNESS: unknown
      ( D ) TOPOLOGY: unknown ( i i ) MOLECULE TYPE: cDNA ( x i ) SEQUENCE DESCRIPTION: SEQ ID NO:85:

```
GTTTGTTGTT TTTCTATTAA ACTGCATAAA GAAACGGCAA AAAAAAAAA AAAAAA             57
```

( 2 ) INFORMATION FOR SEQ ID NO:86:

( i ) SEQUENCE CHARACTERISTICS:
        ( A ) LENGTH: 109 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:86:

```
GGCTGCCTTA  TAATTTTTGT  CTCTTTCTTT  CCCACCTTTA  ATTGTCAATG  GTTAAAAAAA        60
TGCTGTTTTC  TGATATTAAA  TTTTTATTAG  TGCATACCTT  AAAAAAAAA                    109
```

( 2 ) INFORMATION FOR SEQ ID NO:87:

( i ) SEQUENCE CHARACTERISTICS:
        ( A ) LENGTH: 97 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:87:

```
TATATGCGTT  AATATTTCTT  TCCATCTGTG  GATTGTTCTG  TCACTTATTT  TCTTTAATAA        60
ATGGGTTTCT  GAAAAAAAAA  AAAAAAAAA   AAAAAA                                    97
```

( 2 ) INFORMATION FOR SEQ ID NO:88:

( i ) SEQUENCE CHARACTERISTICS:
        ( A ) LENGTH: 115 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:88:

```
TTCCATGCCC  TGTTTTATTT  TCTACTTTAT  TGCCCCTGTT  CCCCAGGCAC  AAAGCTATGT        60
GCTGACATAC  ATTTGGCTCT  CAATAATACT  TGTCATATTT  GAAAAAAAAA  AAAAA            115
```

( 2 ) INFORMATION FOR SEQ ID NO:89:

( i ) SEQUENCE CHARACTERISTICS:
        ( A ) LENGTH: 96 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:89:

```
TTTTAATTTA  CATTTTTATT  TATTTTGTAA  TTATGATTTG  GGTTGGGGAA  GGGGGGGGCT        60
ACATTATAAA  CGCTTAGGAA  TTCGAGCTCG  GTACCC                                    96
```

( 2 ) INFORMATION FOR SEQ ID NO:90:

( i ) SEQUENCE CHARACTERISTICS:
        ( A ) LENGTH: 53 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:90:

TATCAAATAC CAAGTTTATT TCACAAACAC TAGGAAGATG GGTTGAGGGT GGG    53

( 2 ) INFORMATION FOR SEQ ID NO:91:

( i ) SEQUENCE CHARACTERISTICS:
        ( A ) LENGTH: 102 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:91:

ACAAATGGTA GGCAAAAAAA GATATCGCAG TAAGGCCCTC CGTGATTCAC TTCATATGTT    60

TATGTATTGG TTGAATTATT TATGTAAAAA AAAAAAAAAA AA    102

( 2 ) INFORMATION FOR SEQ ID NO:92:

( i ) SEQUENCE CHARACTERISTICS:
        ( A ) LENGTH: 83 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:92:

ATGTCTAACT TTTAATATGC TTGTTCAGCT CTAATAAAGT AATAAAGCTT GGTTGTCAGT    60

ATAAAAAAAA AAAAAAAAAA AAA    83

( 2 ) INFORMATION FOR SEQ ID NO:93:

( i ) SEQUENCE CHARACTERISTICS:
        ( A ) LENGTH: 57 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:93:

ATGAGCTTTA CTCAATAAAG CTGGCTTTCC CTGCAAAAAA AAAAAAAAA AAAAAA    57

( 2 ) INFORMATION FOR SEQ ID NO:94:

( i ) SEQUENCE CHARACTERISTICS:
        ( A ) LENGTH: 92 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:94:

CAAGGAGCAT AAGAGATGTT CTCGTAGCTC TGCGTTGTGT GAAATGTCCA TCTTAGTTTT    60

GTTAAAAAAA AAAAAAAAA AAAAAAAAA AA    92

( 2 ) INFORMATION FOR SEQ ID NO:95:

( i ) SEQUENCE CHARACTERISTICS:
        ( A ) LENGTH: 76 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:95:

CAATCCTGAT GCAAGAGAAG CCAATGATGG GCTCATTTCG AACTGTGTTA TATTATTTAG 60

GAAAAAAAAA AAAAAA 76

( 2 ) INFORMATION FOR SEQ ID NO:96:

( i ) SEQUENCE CHARACTERISTICS:
        ( A ) LENGTH: 55 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:96:

TCTTGATGTT ATGCAAGTAC AGACGTACTT TAAATTTTTG TTATGAAAAA AAAAA 55

( 2 ) INFORMATION FOR SEQ ID NO:97:

( i ) SEQUENCE CHARACTERISTICS:
        ( A ) LENGTH: 85 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:97:

ATGTCTTGAT GTTATGCAGG AAGTACAGAC ATACTTTAAA TTTTGTTATG AAAAAAAAA 60

AAAAAAAAA AAAAAAAAA AAAAA 85

( 2 ) INFORMATION FOR SEQ ID NO:98:

( i ) SEQUENCE CHARACTERISTICS:
        ( A ) LENGTH: 113 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:98:

ATGGACTATC AGAAATAGAC ACAGATTTGG GTCACAAAGC TGGCTCTGTA TTTGCATTTT 60

ATTTTTGTGT TCTTGTCAGT TTGGGAATGA TTAATATTAA AAAAAAAAA AAA 113

( 2 ) INFORMATION FOR SEQ ID NO:99:

( i ) SEQUENCE CHARACTERISTICS:
        ( A ) LENGTH: 114 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:99:

AGGCAAAAAA GATATGCAGG AAGGCCCTCC GAGATTCACT TCATATGTTT ATGTATTGGT 60

TGAATTATTT TTGTAATTTT AAAAAAAAA AAAAAAAAA AAAAAAAAA AAAA 114

( 2 ) INFORMATION FOR SEQ ID NO:100:

( i ) SEQUENCE CHARACTERISTICS:
        ( A ) LENGTH: 83 base pairs
        ( B ) TYPE: nucleic acid
        ( C ) STRANDEDNESS: unknown ( D ) TOPOLOGY: unknown ( i i ) MOLECULE TYPE: cDNA ( x i ) SEQUENCE DESCRIPTION: SEQ ID NO:100:

```
GTGCAGTGTA CCACATTTTC TTTATCCAGT CTATCATTGA TGGACATTAA AGGTTGATTG    60

ATGCAAAAA AAAAAAAAA AAA    83
```

( 2 ) INFORMATION FOR SEQ ID NO:101:

( i ) SEQUENCE CHARACTERISTICS:
        ( A ) LENGTH: 91 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:101:

```
AACCATTTTC ATATAATTTT ATCATACTGT ATCTGCAAAC TTTTATGTCC TGCTTTTCCC    60

TTGAATATTG TGTCATAAGC ATTTAAAAAA A    91
```

METHODS AND COMPOSITIONS USEFUL IN THE RECOGNITION, BINDING AND EXPRESSION OF RIBONUCLEIC ACIDS INVOLVED IN CELL GROWTH, NEOPLASIA AND IMMUNOREGULATION

This is a continuation-in-part of U.S. application Ser. No. 07/881,075, filed May 11, 1992, U.S. Pat. No. 5,444,149.

BACKGROUND OF THE INVENTION

1. Field of the Invention

This invention relates to proteins which contain amino acid sequences that bind to 3'-untranslated regions of mRNAs, particularly mRNA sequences containing "instability sequences" and sequences affecting the translation and localization of mRNA.

2. Discussion of the Background

General features of primary sequence that characterize RNA- and DNA-binding proteins have begun to become apparent. The helix-turn-helix (Pabo et al, *Annu. Rev. Biochem.*, (1984) 53: 293–321) and zinc-binding finger (Evans et al, *Cell* 1988) 52: 1–3) arrangements have both been observed as structural features of sequence-specific DNA-binding proteins. In eukaryotes, the homeobox domain seems to represent a widespread primary sequence motif for specific DNA-binding (Levine et al, *Cell* (1988) 55: 537–540; Robertson, *Nature* (1988) 336: 522–524, and references therein), and the members of the steroid hormone receptor superfamily of DNA-binding proteins utilize a common motif which forms zinc-binding fingers (Evans, *Science* (1988) 240: 889–895).

Early on RNA-binding proteins were less well studied than DNA-binding proteins; general features of RNA-binding proteins were not evident until the recognition of an amino acid octamer present in four proteins associated with mammalian nuclear RNAs (Adam et al, *Mol. Cell Biol.* (1986) 6: 2932–2943). The recognition of RNA by proteins has appeared to the inventors to be a key reaction in the regulation of expression of the genetic material of all cells.

One of the present inventors has studied RNA binding proteins of this group for many years and in 1983 isolated the first eukaryotic recombinant cDNA member of this family of proteins that encodes the human La RNA binding protein (Chambers et al, *Proc. Natl. Acad. Sci.* (USA) (1985) 82: 2115–2119; Chambers et al, *J. Biol. Chem.* (1988) 263: 18043–18051).

Subsequently, the observation by Dreyfuss and coworkers (Adam et al, *Mol. Cell. Biol.* (1986) 6: 2932–2943; Swanson et al, *Mol. Cell. Biol.* (1987) 1: 1731–1739) of an "RNP consensus" octamer in several eukaryotic proteins associated with RNA was an early indication that an amino acid sequence common among some RNA-associated proteins might exist.

Other publications by the Dreyfuss group (Dreyfuss et al, *TIBS* (1988) 13: 86–91) and from many other laboratories (Amrein et al, *Cell* (1988) 55, 1025–1035; Bell et al, *Cell* (1988) 55, 1037–1046; Bugler et al, *J. Biol. Chem.* (1987) 262: 10922-1-925; Chambers et al (1988), ibid; Deutscher et al, *Proc. Natl. Acad. Sci.* (USA) (1988) 85: 9479–9483; Goralski et al, *Cell* (1989) 56, 1101–1108; Keene, J. D., *J. Autoimmunity* (1989) 2: 329–337; Merrill et al, *J. Biol. Chem.* (1988) 263, 3307–3313; Sachs et al, *Mol. Cell. Biol.* (1986) 7, 3268–3276) noted the presence of related sequences surrounding the octamer and speculated that these regions might participate in RNA binding. It was not known at that time however whether these sequences might endow specific as opposed to nonspecific recognition of RNA or if discontinuous regions involving long-range interactions within these proteins might be required for RNA binding.

Some authors speculated that the octamer alone (Dreyfuss et al, *TIBS* (1988) 13: 86–91) or the octamer and its surrounding residues constituted an RNA binding domain and Dreyfuss and coauthors (ibid) chose an arbitrary size of 100 amino acids. Their theory was based upon the occurrence of similar sequences in a set of proteins that were all thought to be associated with RNA. Evidence for direct binding of such regions to specific RNA sequences was not available and no domains of proteins with binding activity were defined experimentally.

Included in this theory was the speculation that the 70K U1 snRNP protein contained an RNA binding domain of 93 amino acids from positions 94 to 186. Other investigators (Theissen et al, *EMBO J.* (1986) 5: 3209–3217) had speculated that a different region of the 70K U1 snRNP protein encompassing amino acid residues 241 to 437 as well as the same region speculated by Dreyfuss were either one or both involved in RNA binding. These speculations were based upon the relationship of the highly basic (positively charged) region at amino acids 241 to 437 of 70K protein to regions of other proteins (e.g., protamines and histones) known to bind nucleic acid. No experimental evidence was available to support these suggestions.

Although the 70K protein is one of ten proteins known to be associated with the U1 snRNP complex (Pettersson et al, *J. Biol. Chem.* (1984) 259: 5907–5914), there was no evidence of specific RNA protein contact between the 70K protein and any RNA species until the discovery of a specific and direct binding of the 70K protein to U1 RNA. Furthermore, of the other members of this group of proteins studied in the inventors' laboratory, as well as, in many other laboratories, none was shown to directly bind to a specific RNA sequence until one of the present inventors discovered the sequence-specific interaction between 70K U1 snRNP protein and U1 RNA (C. Query et al, *Cell* 57:89 (1989)).

The region of the protein involved in this specific binding involves a different amino acid sequence of 70K protein than that speculated by Theissen et al or by Dreyfuss et al. In fact, one of the sequences proposed by Theissen as being responsible for RNA binding actually interferes with the detection of specific binding activity. (C. Query et al, *Cell* 57:89 (1989); Query et al, *Mol. Cell Biol.* 9: 4872 (1989)).

In addition, the discovery that the precise RNA binding domain of the 70K protein includes additional important amino acid sequences not previously recognized by the theory of Dreyfuss et al, by the published work of other workers mentioned above or by some of the inventors themselves in their earlier studies of La (Chambers et al, ibid) and the 60 kD Ro (Deutscher et al, ibid) protein members of the group.

RNA binding proteins are now known to be involved in the control of a variety of cellular regulatory and developmental processes, such as RNA processing and compartmentalization, mRNA translation and viral gene expression. Some proteins that recognize and bind RNA can be classified into families based upon primary sequence homology, as well as higher order structure.

The family of RNA binding proteins containing an RNP consensus octamer and an 80 amino acid motif implicated in RNA recognition (RRM) has been the subject of intense investigation. Query et al, *Cell* (1989) 57: 89–101; Kenan et al, *Trends Biochem. Sci.* (1991) 16: 214–220. Based upon crystallographic and NMR spectroscopic studies of the U1 RNA binding domain of the U1 snRNP-A protein a model of the tertiary structure has been derived. The tertiary structural model together with RNA binding studies have led to the suggestion that the RNA binding surface resides on a monomeric unit with four anti-parallel β-strands which contains solvent exposed aromatic and basic residues. Kenan et al (1991) supra. Additional biochemical data have demonstrated that a determinant of RNA binding specificity resides in a loop which connects two β-strands. Bentley et al, *Mol. Cell. Biol.* (1991) 11: 1829–1839.

More than forty members of the RRM superfamily have been reported to date, the majority of which reside in all tissues and are ubiquitously conserved in phylogeny. Kenan et al (1991) supra. Tissue-specific members of the RRM family are less common, including X16 which is expressed in pre-B cells, Bj6 which is a puff-specific Drosophila protein and elav (embryonic lethal abnormal vision) which is neuronal-specific in Drosophila. For some RRM proteins the natural RNA ligands have been identified or surmised, but the RNA-binding sequences are not known in most cases.

The RNA ligands for the tissue-specific RRM proteins have not been reported and may prove difficult to determine because of their specialized roles in certain developmental processes. However, in order to understand their functions in cellular RNA metabolism and development, it will be essential to identify the RNA sequences to which they bind.

Oncogenes encode growth factors that affect the rate of cell proliferation by influencing cell cycle events such as mitosis, intracellular signaling pathways and gene expression. Some well known oncogenes are c-src, c-myc and c-fos. Lymphokines, which affect the growth properties of immunoregulatory cells, also function as growth factors similar to oncogene products. Although oncogene products (oncoproteins) are central components in the origin of the neoplastic state, they work through a variety of complex and largely unknown pathways. Consequently, methods to specifically control the functions of oncoproteins are generally lacking.

The more recent discovery of suppressor oncogenes (anti-oncogenes) has held promise for being able to counter the effects of oncogenes. Some examples of anti-oncogenes include: retinoblastoma (Rb) and p53. It is hoped that these factors can be used to counter the effects of oncoproteins and thus, provide new treatments for cancer. For example, breast tumors show a consistent defect in the p53 gene, thus, preventing p53 from countering the oncogenes that cause uncontrolled proliferation of the breast tumors. Unfortunately, there are likely to be dozens of anti-oncogenes, some being specific to a given type of cancer and others functioning in combinations in various cancers.

Given the potential for cellular growth proteins to generate defects in cellular proliferation and differentiation, it is essential that multiple mechanisms exist to balance against their overproduction. The complex molecular circuitry involving receptor and nonreceptor-mediated tyrosine phosphorylation, as well as the action of GTPases and transcription factors requires multiple control points (J. M. Bishop, *Cell* 64: 235 (1991); L. C. Cantley et al, *Cell* 64: 281 (1991)). For example, the transcription of growth regulatory genes is tightly regulated at the level of the DNA promoter (B. Lewin, *Cell,* 64: 303 (1991)). Likewise, one would expect similar control mechanisms to exist in the cytoplasm to prevent inappropriate translation of growth factor mRNAs. Direct evidence for control of growth factor production in the cytoplasm is lacking. However, it is clearly documented that the oncoprotein messages themselves are tightly regulated (G. Shaw et al, *Cell,* 46: 659 (1986); D. Caput et al, *Proc. Natl. Acad. Sci. USA* 83: 1670 (1986); G. Brewer, *Mol. Cell Biol.* 5: 2460 (1991); T. R. Jones et al, *Mol. Cell Biol.* 7: 4513 (1987); A. B. Shyu et al, *Genes & Devel.* 3: 60 (1989); P. L. Bernstein et al, *Genes & Devel.* 6: 642 (1992); A. B. Shyu et al, *Genes & Devel.* 5, 221 (1991); S. Savant-Bhonsale et al, *Genes & Devel.* 6: 1927 (1992); D. W. Cleveland et al, *The New Biologist* 1: 121 (1989); J. Malter, *Science* 246: 664 (1989); E. Vakalopoulou et al, *Mol. Cell Biol.* 11: 3355 (1991); P. R. Bohjanen et al, *Mol. Cell Biol.* 11: 3288 (1991)). In the case of mRNAs encoding c-fos, c-myc and cytokines, the RNAs are unstable and short lived, and it has been reported that they undergo translational regulation (V. Kruys et al, *Proc. Natl. Acad. Sci. USA* 84: 6030 (1987); V. Kruys et al, *Science* 245: 852 (1989); R. Wisdom et al, *Genes & Devel.* 5: 232 (1991)). However, alterations in the mRNA stabilities of these oncoproteins have been reported to result in cellular transformation (F. Meijlink et al, *Cell* 36: 51 (1985); Ch. Dani et al, *Proc. Natl. Acad. Sci. USA* 81: 7046 (1984); G. D. Schuler et al, *Cell* 55: 1115 (1988)). Recent evidence from various cellular systems have implicated 3' untranslated regions (3' UTRS) of mRNAs in the regulation of growth and differentiation (F. Rastinejad et al, *Cell* 72: 903 (1993)).

Accordingly, there is a strongly felt need for the discovery of materials generally useful in the recognition, binding and/or expression of ribonucleic acids involved in growth, neoplasia and immunoregulation. Such materials would have many uses, including regulation of cell proliferation in vitro and in vivo, regulation of immune cell expression, stimulation of cell growth and tissue regeneration, the production of transgenic animals and cell lines for pharmaceutical tests of cancer, immune function and neurological diseases, diagnostic reagents for the detection of autoantibodies associated with cancers, in vivo targeting systems, in diagnosing pathology specimens of neuronal origin, and/or as genetic or neurogenetic disease markers involving malformations of the central nervous system.

SUMMARY OF THE INVENTION

Accordingly, one object of this invention is to provide novel proteins, and their corresponding DNA and mRNA sequences, which can bind to mRNAs which encode growth regulatory proteins, oncoproteins or lymphokines.

It is another object of this invention to provide novel proteins, and their corresponding DNA and mRNA sequences, which can bind to untranslated regions of mRNAs, particularly 3'-untranslated regions of mRNA or mRNA "instability sequences", in eukaryotic cells.

It is another object of this invention to provide novel proteins, and their corresponding DNA and mRNA sequences, which can provide, in cell cultures or in vivo, the ability to modulate the expression of oncogenes and/or lymphokine-encoding genes in eukaryotic cells.

It is another object of this invention to provide novel proteins, and their corresponding DNA and mRNA sequences, useful in the regulation of cell proliferation in cell cultures and in vivo.

It is another object of this invention to provide novel proteins, and their corresponding DNA and mRNA sequences, which can be used to take cells out of a proliferative state and into a state of differentiation.

It is another object of this invention to provide novel proteins, and their corresponding DNA and mRNA sequences, useful in the regulation of immune cell gene expression.

It is another object of this invention to provide novel proteins, and their corresponding DNA and mRNA sequences, useful for stimulating or suppressing plant or animal cell growth.

It is another object of this invention to provide novel proteins, and their corresponding DNA and mRNA sequences, useful to produce transgenic plants or animals and cell lines for pharmaceutical tests of cancer, immune function and/or neurological diseases.

It is another object of this invention to provide novel proteins, and their corresponding DNA and mRNA sequences, useful as diagnostic and/or therapeutic reagents for the detection or therapy of autoantibodies present in the body of a cancer patient.

It is another object of this invention to provide novel proteins, and their corresponding DNA and mRNA sequences, which can be used for the in vivo targeting of certain substances.

It is another object of this invention to provide novel proteins, and their corresponding DNA and mRNA sequences, useful for diagnosing pathology specimens of neuronal origin.

It is another object of this invention to provide novel proteins, and their corresponding DNA and mRNA sequences, useful as genetic or neurogenetic disease markers in the diagnosis and/or therapy of patients in need thereof.

It is another object of the present invention to provide a method for obtaining subsets of mRNA which encode functionally related proteins such as those influencing cell proliferation or differentiation.

The present invention which satisfies all of the above objects of the invention, and others as can be seen from the description of the invention given hereinbelow, relates to novel proteins, named Hel-N1 and Hel-N2 (ΔHel-N1) by the inventors, and related proteins, discovered by the inventors as being able to bind to 3'-untranslated mRNAs, including sequences (such as the "instability sequences") that are present in messenger RNAs that encode oncoproteins and lymphokines. The "instability sequences", discovered by Shaw et al (*Cell* (1986) 46: 659–667), are one characteristic type of target element which reside in the 3'-noncoding regions of mRNAs which encode oncoproteins and lymphokines. These sequences represent only one of several target motifs in the noncoding regions of growth regulatory mRNAs which are addressed by this invention. The present invention also provides DNA and mRNA sequences corresponding to Hel-N1 and the related proteins.

BRIEF DESCRIPTION OF THE FIGURES

A more complete appreciation of the invention and many of its attendant advantages will be readily obtained as the same becomes better understood by reference to the following detailed description when considered in connection with the accompanying figures.

FIG. 1 provides an amino acid sequence comparison of two Drosophila neuron-specific proteins, elav (SEQ ID NO:1) and K3 (rbp9), (hereinafter referred to as K3; (SEQ ID NO:3)) with that of the human counterpart, Hel-N1 (SEQ ID NO:2). Open boxes represent the RNP2 consensus sequences of each RNA recognition motif, whereas, shaded boxes represent RNP1 consensus sequence. Vertical lines denote identical residues and hyphens denote gaps used to allow optimal alignment among the three sequences.

FIG. 2 provides a comparison of the three RRMs of elav (SEQ ID NOS:14, 17 and 20), K3 (SEQ ID NOS:15,18 and 21) and Hel-N1 (SEQ ID NOS:16, 19 and 22) with those of polypyrimidine tract binding protein (PPTB) (SEQ ID NO:4–6) (Garcia-Blanco et al, *Proc. Nat. Acad. Sci. (USA)* (1990) 87: 3082–3086, hnRNP-L (SEQ ID NOS:7–9) (Pinol-Roma et al, *J. Cell. Biol.* (1989) 109: 2575–2587, Drosophila sex lethal (Sxl) (SEQ ID NOS:10–11) and two other Drosophila proteins K1 (SEQ ID NO:12) and K2 (SEQ ID NO:13) as depicted by Kenan et al, (1991). Asterisks indicate key residues critical to the correct folding of the RNA binding domain.

FIGS. 3 and 4 set forth RNA sequences (SEQ ID NO:23–49) selected to bind Hel-N1 using a random RNA selection procedure (Tsai et al *Nucl. Acids Res.*, (1991) 19: 4931–4936). FIG. 3 sets forth thirty RNA sequences, 25 nucleotides in length, which were identified from clones generated by reverse transcription and PCR amplification of selected RNAs. Twenty seven of the sequences consistently contained short stretches of uridylate residues interspersed with other nucleotides (boxed region). Two of the U-rich sequences were obtained twice. The two selected sequences shown at the bottom of the figure (B-17 and B-5) lack the stretches of uridylates. FIG. 4 shows, among the sequences selected to bind Hel-N1 (FIG. 3), those that were found among the 3'-UTR instability sequences indicated by Shaw et al, *Cell* (1986) 46: 659–667.

FIG. 6 sets forth the nucleotide sequence (SEQ ID NO:50) and the amino acid sequence (SEQ ID NO:51) of a paraneoplastic encephalomyelitis antigen, HuD, reported by Szabo et al, *Cell* (1991) 67: 325–333.

FIG. 11 shows the sequences (SEQ ID NOS:52 and 53), respectively selected from a randomized RNA library by binding to Hel-N1 and Hel-N2 under high stringency conditions. This RNA pool contained a degenerate 25 nt. sequence in the middle of an 80 nt. synthetic oligonucleotide as described by D. E. Tsai et al, *Nuc. Acids Res.* 19: 4931 (1991). In the second round of selection, 0.53M NaCl was added to the NT2 washing buffer. In the third round selection 0.5M NaCl and 1.0 urea were added into the NT2 washing buffer. For Hel-N2, twenty selected RNAs (SEQ ID NOS:54–73) and for Hel-N1, six selected RNAs (SEQ ID NOS:74–79) are shown. The uridylate-rich stretches in each RNA are in bold characters and a deduced consensus sequence (SEQ ID NO:80) is shown which holds for both Hel-N1 and Hel-N2 selected RNAs.

DETAILED DESCRIPTION OF THE PREFERRED EMBODIMENTS

Figure 5:
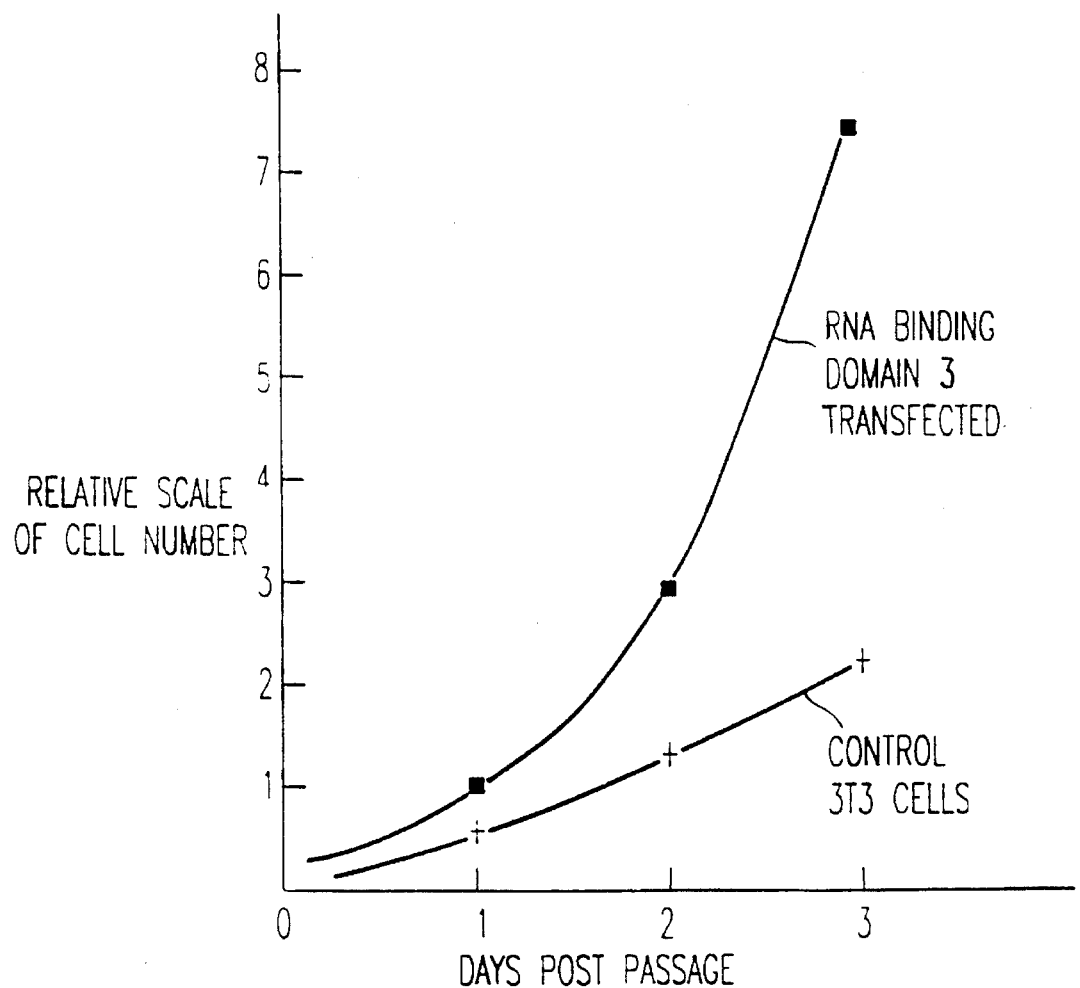
FIG. 5 illustrates a cellular growth curve obtained in accordance with the invention.

In this text, the following standard nomenclature is used.

TABLE 1

Amino acid symbols.

| Amino acid | Three-letter symbol | One-letter symbol |
| --- | --- | --- |
| Alanine | Ala | A |
| Arginine | Arg | R |
| Asparagine | Asn | N |
| Aspartic acid | Asp | D |
| Asn + Asp | Asx | B |
| Cysteine | Cys | C |
| Glutamine | Gln | Q |
| Glutamic acid | Glu | E |
| Gln + Glu | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The inventors have been isolating and characterizing RNA binding proteins, and studying their RNA-binding specificities. More particularly, as described in greater detail in application Ser. Nos. 07/536,943 and 07/436,779, filed on Jun. 12, 1990 and Nov. 15, 1989, respectively, all of which are hereby incorporated by reference, in studying the RNA-binding properties of the U1 RNA-associated 70K protein to elucidate regions of RNA-protein interaction, one of the inventors of the present invention, together with others, identified a central amino acid sequence involved in the specificity of gene expression at the level of pre-messenger RNA splicing in cells. While several structural motifs of proteins important in sequence-specific DNA-binding had been identified (e.g., helix-turn-helix and zinc-binding fingers) and two primary sequence motifs recently have been implicated directly in DNA-binding (homeoboxes and sequences within the steroid receptor family which form zinc-binding fingers), the structure or primary sequences of RNA-binding domains were not known prior to the invention of application Ser. Nos. 07/536,943 and 07/436,779.

A Drosophila protein, Elav, which is related to Hel-N1, is known to be involved in the early development of the central nervous system (CNS). Homozygous mutations of this gene locus give rise to numerous structural defects and hypotrophy of the CNS leading to embryonic lethality. Its role in neuronal growth and differentiation of the Drosophila nervous system is also underscored by the temporal appearance of elav transcripts during the differentiation of neuroblasts into primitive neurons.

In probing for rat and human elav counterparts, the inventors relied on a novel approach of using degenerate primers designed to simulate the RNP-1 octamer sequence present in two of the three RRMs of Drosophila elav and thereby isolated cDNA encoding a novel neuron-specific protein, named Hel-N1 by them, from human brain by a combination of degenerate PCR probing and hybridization and found it to contain three RNA-recognition motifs (RRMs)*. FIG. 1 provides the complete amino acid sequence of Hel-N1.

*The term "recognition motif" is used herein to designate an amino acid relationship; the term "RNA binding domain" designates a peptide segment shown to possess binding activity results. In this sense, RNA-binding domain 3 may be a dominant negative suppressor of the function of Hel-N1.

In in vitro studies they found that, in RNA binding, Hel-N1 prefers short stretches of uridylate residues and can bind the 3'-untranslated regions of c-myc, c-fos, and GM-CSF messenger RNAs, and that although Hel-N1 has three RRMs, the third one (the most C-terminal binding domain situated between about amino acid positions 259 and 359) is sufficient for mRNA 3'-untranslated region (which encompasses the instability sequence) binding activity. The inventors further discovered that full length Hel-N1, when transfected into a cell, caused cellular growth to cease. But, by contrast, and quite surprisingly, when only the third RNA binding domain was transfected into cells, the opposite result was obtained—the cells underwent rapid growth (as illustrated in FIG. 5).

It is not known whether transfection with the third RNA binding domain alone causes cellular transformation in the sense of an oncogene. By RNA binding the single domain alone can interfere with the ability of the full length Hel-N1 protein to bind in a multimeric fashion along the 3' UTR of the oncoprotein or lymphokine mRNA. Thus, apparently the mRNA is rendered functional and thus, more rapid proliferation The inventors' data demonstrates that the Hel-N1 protein binds as a multimer along the mRNA, presumably enhancing its localization, instability and/or regulating its translatability and/or deadenylating it (thus, less proliferation). This protein may be responsible for the growth cessation of neurons.

Figure 7:
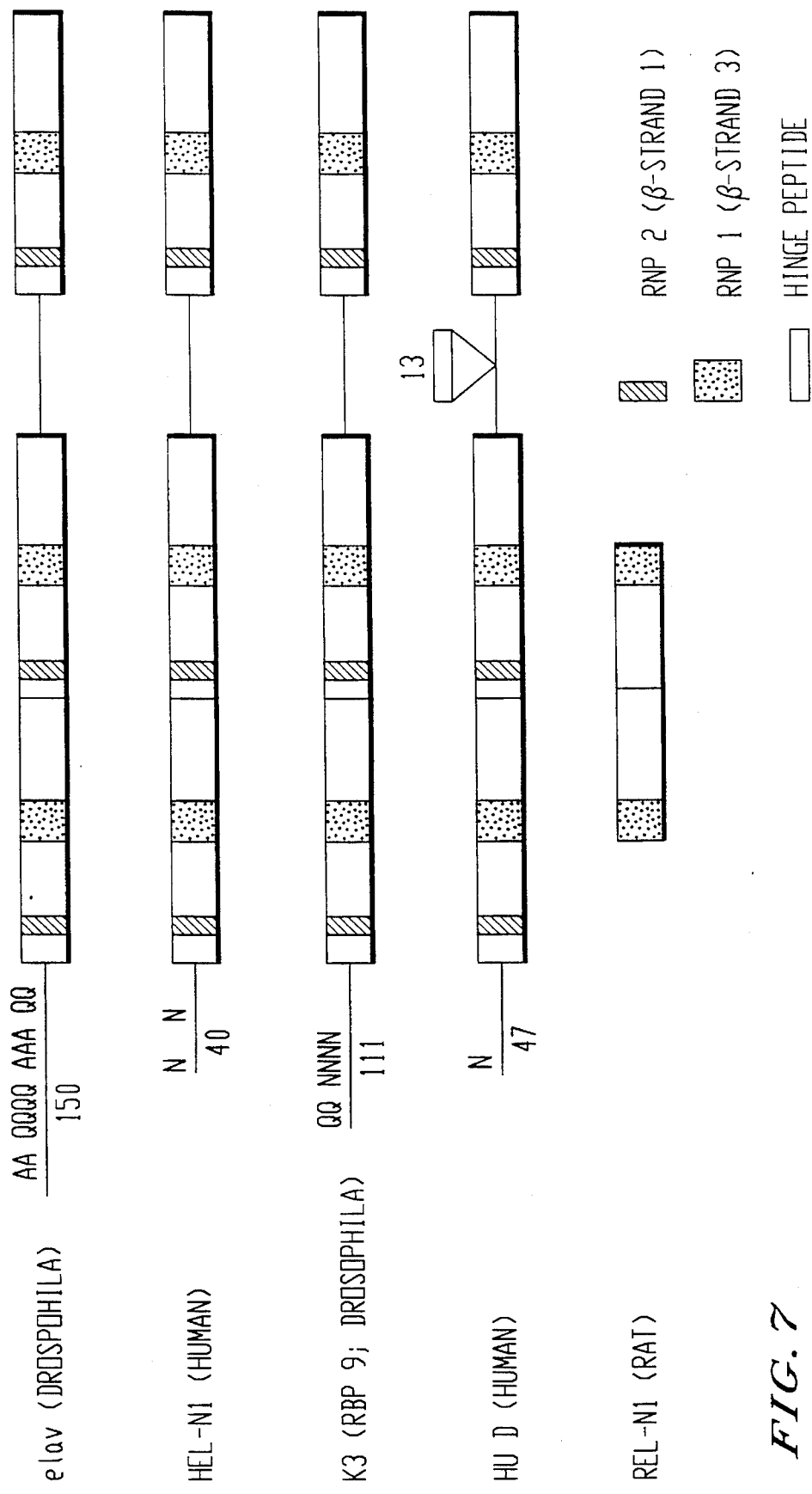
FIG. 7 is a comparative diagram of elav subfamily members' amino acid sequences.

Interestingly, recently Szabo et al (*Cell* (1991) 67: 325–333) reported the isolation of a cDNA encoding another human protein, termed HuD, based upon its reactivity with antisera from patients with paraneoplastic encephalomyelitis. But Szabo et al do not describe any binding by HuD to mRNA 3'-untranslated sequences, or mRNA instability sequences. HuD is also homologous to elav in the RRMs, but differs from elav, K3 and Hel-N1 at its amino terminus and other places (see FIG. 7). Thus, to date there are nine members of this subfamily (Hel-N1, Hel-N2, HuD1, HuD2, HuD3, HuC1, HuC2, K3(rbp9), elav) and more are likely to be discovered.

Due to the high level of homology between them, the segments of elav found between amino acid positions about 393 and about 483, of K3 found between amino acid positions about 345 and about 444, and of HuD found between amino acid positions about 280 and about 380 can be used in accordance with the invention in lieu of the third domain of Hel-N1. (The amino acid sequences of elav and of K3 are set forth in FIG. 1, that for HuD is set forth in FIG. 6.)

The present invention thus relates to the full length Hel-N1 protein, to its third domain and related elav, K3, HuC and HuD segments, and to the exploitation of any of these proteins and their binding reaction to the 3'-untranslated regions containing the instability sequence of oncoprotein and lymphokine mRNAs (Shaw et al, 1986) as well as to different structural fusions that can be produced to target these mRNAs for up or down regulation. Further, this invention is applicable to any other heterogenous nuclear RNA-binding proteins which allow for the partitioning of specific subsets of messenger RNA's.

The present proteins, namely either full length Hel-N1 or its third domain, can be used to obtain a binding reaction between two ligands in a manner analogous to that described in application Ser. Nos. 07/536,943 and 07/436,779, noted supra. For example, any number of other adducts (RNA or protein) can be attached to either of these ligands to create novel and useful ribonucleoproteins, or a ribonuclease can be attached to the RNA binding domain 3 using known techniques to directly target any of these mRNAs for destruction.

The proteins of the present invention can therefore be used as therapeutic reagents to provide for either growth suppression or growth stimulation. Full-length Hel-N1 can be used to cause growth suppression of cultured cells, presumably mediated through effects on the stability of messenger RNAs encoding growth factors. In accordance with the present invention, one can alter the growth properties of cells in which oncogenes and lymphokine genes are overexpressed. Thus, cancer cells, which may be targeted by any known standard means, including gene therapy, liposome-mediated delivery, retrovirus-mediated infection or direct infusion with Hel-N1 DNA, RNA or protein will consequently be retarded in their growth.

Likewise, immune cells regulated by cytokines, such as interleukins, interferons, and others can be growth suppressed using Hel-N1. In this embodiment, leukemic and lymphocytic cells targeted by delivery of Hel-N1 DNA, RNA or protein to the bone, thymus or bloodstream using known techniques become incapacitated. For example, immune B or T cells overproducing autoantibodies or other harmful antibodies can be targeted using antigens or antibodies imbedded in liposomes or other known carriers which in turn, deliver Hel-N1 DNA, RNA or protein as a growth suppressor to destroy their ability to proliferate. The cells producing the harmful antibodies become thus incapacitated and immunosuppressive therapy can be enhanced in a specific manner.

In these regimens, Hel-N1 DNA, RNA or protein can be injected directly into cancer patients using known techniques to affect tumor growth. Likewise it can be injected into patients to suppress the proliferation of immune cells. Thus, with many variations on these themes, it can be seen that delivery of Hel-N1 DNA, RNA or protein which can block cell proliferation by suppression of growth factor messenger RNAs is highly advantageous.

As noted above, the inventors have found that the third RNA recognition motif of Hel-N1, found between amino acid positions 259 and about 349 of the Hel-N1 amino acid sequence provided in FIG. 1, constitutes the core of the oncoprotein and cytokine mRNA binding domain. This approximately 100 amino acid-long fragment is responsible for the specific 3'-untranslated sequence binding activity.

The inventors also made the startling discovery that expression of this domain, by itself, results in rapid proliferation of cells. This is a result opposite to that obtained by using full length Hel-N1. Expression of RNA binding domain 3 of Hel-N1 caused an eightfold increase in the growth of cultured cells after 3 days, as illustrated in FIG. 5. This is a striking alteration in a rate of proliferation. Thus, the RNA binding fragment of the growth suppression protein, Hel-N1, can itself be used to lead to the reverse effects, rapid cell growth.

Delivery of this fragment to tissue can be used to regenerate growth of cells in that tissue. One can use this embodiment to regenerate nervous tissue, heart tissue, skin and other tissues of limbs and organs. Likewise, RNA binding domain 3 can be delivered to tissues involved in wound healing and at other sites that are unable to be otherwise stimulated. Immune cells that produce autoantibodies and other factors needed for protection of the body can be growth stimulated using this invention.

Hel-N1 is an autoimmune protein in certain patients who show central nervous system manifestations of cancer called paraneoplastic cerebellar degeneration of (PCD), paraneoplastic encephalomyelitis (PE) or paraneoplastic sensory neuropathy (PSN). A therapeutic regimen could involve injection of Hel-N1 or peptides derived from Hel-N1 in order to block the immune effect or cellular immune recognition for properties in these diseases. Large amounts of pure Hel-N1 or its third domain are readily available using standard DNA cloning technologies or protein synthesis technologies. The purified protein can be used for immuno depletion of harmful autoantibodies or autoantibody—producing cells using methods of apheresis or dialysis.

The inventors also surprisingly discovered that full-length Hel-N1 can take cells out of a proliferative state and into a state of differentiation. Illustratively, whereas the third RNA binding domain of Hel-N1 was discovered to cause increased cell growth and the whole Hel-N1 protein discovered to cause cessation of cell growth, the inventors also observed that when certain neuroblastoma cells of (B104) were subjected to expression of whole Hel-N1 protein the cells developed an altered morphology. The cells became elongated like muscle cells and began to produce myotubules consisting of myosin and actin fibrils.

A cell derived from brain tissue was caused to enter an apparent myogenic pathway of differentiation by use of a protein of the present invention. This effect was thought due to the presence of a growth factor whose mRNA contained a target sequence to which Hel-N1 was able to bind. In this case, the growth factor appears to be the Id protein which is known to suppress muscle differentiation or a related growth regulatory factor. In the case of other similar growth factors, Hel-N1 may affect the differentiation of any cell which depends upon the continued expression of a growth factor encoded by an mRNA containing a target sequence.

Thus, in another embodiment, Hel-N1 can be used in somatic or germline therapy to cause cells to undergo a desired pathway of differentiation. Hel-N1 has the further ability to control the balance between proliferation and differentiation that determines the developmental versus neoplastic consequences of gene expression.

The proteins of the present invention are also useful in therapeutic testing. An important need in the field of cancer research and immunology is for animal models which manifest altered growth properties or immune disregulation. Transgenic expression of polypeptides described in this application, using known techniques, can provide animals in which specific tissues or organs have been targeted to proliferate more rapidly or more slowly, thus allowing animal models of cancer or immune regulation to be produced. These animals are useful for testing the effect of chemotherapeutic drugs, radiation therapies, immune irregulatory agents, such as immunosuppressors and immunostimulators. Furthermore, Hel-N1 is itself an autoantigen to which patients with certain paraneoplastic diseases produce an autoantibody. The expression of Hel-N1 in transgenic tissues can allow production of an animal model for this autoimmune-type of cancer.

Proteins of the present invention are also useful in diagnostic applications. As a histological probe, Hel-N1 can be used to identify certain neuron types, such as granule cells or basket cells of the cerebellum. For example, in the pathology laboratory it is useful to stain cells with antibodies specific for Hel-N1 to determine the tissue origin of the specimen in question. Because Hel-N1 is present in certain neurons and not others, its presence in a tissue sample is an indicator of the type of tissue being examined.

Hel-N1 DNA constitutes a novel genetic marker for potential malformations of the central nervous system. For example, in the testing for genetic defects during prenatal examinations, many normal as well as abnormal markers are needed. For example, Hel-N1, in keeping with known oncogenes and antioncogenes, may be defective in patients suffering frmo natural cancers and leukemias. Full-length Hel-N1 DNA, RNA or protein may be used in the diagnosis and/or therapy of such individuals. Such therapy includes gene therapy, or targeted DNA, RNA or protein delivery. Hel-N1 is a useful, neuronal-specific probe. In testing for cystic fibrosis, Down's syndrome and similar genetic defects, one can get additional information on the status of CNS gene by monitoring Hel-N1 levels.

Thus in one embodiment, the present invention provides a polypeptide having the amino sequence of at least from the amino acid position 259 to 349 of Hel-N1 set forth in FIG. 1, and up to the whole amino acid sequence of Hel-N1. In another embodiment, the present invention provides a polypeptide which can be used to promote cell growth, where the polypeptide has the amino acid sequence of from amino acid position about 259 to about 349 of Hel-N1, or about position 393 to about position 483 of elav or about position 345 to about position 444 of K3, or about position 280 to about position 380 of HuD. In another embodiment, the present invention provides a polypeptide which can be used to suppress cell growth, and in particular expression of oncogenes and/or lymphokine encoding genes, by using a polypeptide having the whole amino acid sequence of Hel-N1.

In other embodiments, the present invention provides the corresponding DNA sequences and RNA sequences, optionally present in a liposome formulation, which may be either targeted or not targeted, or in a retroviral formulation, or in another formulation suitable for in vitro or in vivo delivery to cells or tissue. In other embodiments, these DNA and RNA sequences may be used in conjunction with gene therapy technology or to produce transgenic animals.

Another embodiment of the present invention relates to method for regenerating a mammalian tissue, including neuronal tissue, by administering to the tissue a polypeptide having the amino acid sequence of from about position 259 to about position 349 of Hel-N1 or the corresponding elav, K3 or HuD segments. The polypeptide may be administered to the tissue using any known means to deliver a polypeptide to a cell culture or in vivo to the cells of certain tissue, including gene therapy, liposome-mediated delivery, retrovirus-mediated infection, or direct infusion with the corresponding DNA, RNA or protein.

In another embodiment, the present invention is used to suppress the expression of an oncogene in a cell and/or of a lymphokine encoding gene in a cell, by causing the cell to express a polypeptide having about the whole amino acid sequence of Hel-N1. As with tissue regeneration, this may be achieved by using any standard means to cause the cell to express the desired polypeptide, including gene therapy, liposome-mediated delivery, retrovirus-mediated infection, or direct infusion with Hel-N1 DNA, RNA or protein. Particular oncogenes which may be targeted, include c-myc, c-fos or c-src, and others. Specific lymphokines which may be targeted in accordance with the present invention include GM-CSF, any interferon, or any interleukin, or others.

Hel-N1 and its associated DNAs and RNAs can also be used to produce transgenic animals and cell lines, using standard and known technologies, for pharmaceutical tests of cancer, immune functions and/or neurological diseases.

The present invention provides a method for using RNA-binding proteins to recognize and bind to a structurally and/or functionally related subset of messenger RNA molecules. NO such proteins have been described previously. Whether these mRNAs are networked or are present in a functionally accessible complex is not known. However, fluorescence data suggest that they may be clustered in specific cytoplasmic granules in medulloblastoma cells. One possible value of being structurally clustered includes the potential for coordinate regulation of mRNA expression in the cytoplasm. It would be highly significant if the growth regulatory factors containing these common 3' UTR sequences represented functionally related networks of intracellular circuits. However, whether Hel-N1 controls localization, translatability or stability of mRNAs involved in a particular growth pathway is not yet known.

The sequences to which Hel-N1 binds have been widely implicated in controlling the instability of the protooncogene and cytokine mRNAs because when the 3' UTR of the highly unstable GM-CSF mRNA was placed next to the coding sequence of b-globin mRNA, instability was conferred (G. Shaw et al, *Cell*, 46: 659 (1986); D. Caput et al, *Proc. Natl. Acad. Sci. USA* 83: 1670 (1986); G. Brewer, *Mol. Cell Biol.* 5: 2460 (1991); T. R. Jones et al, *Mol. Cell Biol.* 7: 4513 (1987); A. B. Shyu et al, *Genes & Devel.* 3: 60 (1989); P. L. Bernstein et al, *Genes & Devel.* 6: 642 (1992); A. B. Shyu et al, *Genes & Devel.* 5, 221 (1991); S. Savant-Bhonsale et al, *Genes & Devel.* 6: 1927 (1992); D. W. Cleveland et al, *The New Biologist* 1: 121 (1989); J. Malter, *Science* 246: 664 (1989); E. Vakalopoulou et al, *Mol. Cell Biol.* 11: 3355 (1991); P. R. Bohjanen et al, *Mol. Cell Biol.* 11: 3288 (1991); V. Kruys et al, *Proc. Natl. Acad. Sci.*

*USA* 84: 6030 (1987); V. Kruys et al, *Science* 245:852 (1989); R. Wisdom et al, *Genes & Devel.* 5: 232 (1991); F. Meijlink et al, *Cell* 36: 51 (1985); Ch. Dani et al, *Proc. Natl. Acad. Sci. USA* 81: 7046 (1984); G. D. Schuler et al, *Cell* 55: 1115 (1988)). The 3' UTR of GM-CSF is similar to the random RNA selection products obtained with Hel-N1 and Hel-N2 in that they contain short stretches of uridylate residues with a predominant AUUUA pentamer. However, careful examination of the sequences present in the 3' UTRs of the various proto-oncogene and cytokine mRNAs shows that a unified consensus sequence is not evident; instead a sequence of character is present with considerable redundancy (G. Shaw et al, *Cell,* 46: 659 (1986); D. Caput et al, *Proc. Natl. Acad. Sci. USA* 83: 1670 (1986); G. Brewer, *Mol. Cell Biol.* 5: 2460 (1991); T. R. Jones et al, *Mol. Cell Biol.* 7: 4513 (1987); A. B. Shyu et al, *Genes & Devel.* 3: 60 (1989); P. L. Bernstein et al, *Genes & Devel.* 6: 642 (1992); A. B. Shyu et al, *Genes & Devel.* 5, 221 (1991); S. Savant-Bhonsale et al, *Genes & Devel.* 6: 1927 (1992); D. W. Cleveland et al, *The New Biologist* 1: 121 (1989); J. Malter, *Science* 246: 664 (1989); E. Vakalopoulou et al, *Mol. Cell Biol.* 11: 3355 (1991); P. R. Bohjanen et al, *Mol. Cell Biol.* 11: 3288 (1991); F. Meijlink et al, *Cell* 36: 51 (1985); Ch. Dani et al, *Proc. Natl. Acad. Sci. USA* 81: 7046 (1984); G. D. Schuler et al, *Cell* 55: 1115 (1988); T. D. Levine et al, *Mol. Cell Biol.* 13: 3494 (1993); P. H. King et al, *J. Neurosci.*, in press). The present invention demonstrates that Hel-N1 recognizes and binds to a variety of target molecules which have certain sequence characteristics in common, but lack the same definitive binding site. Thus, there is likely a "hierarchy of affinities" that exists among these RNA sequences with sufficient differences among them to allow a broad latitude of RNA recognition.

If Hel-N1 or its associated proteins participate in the instability of growth regulatory mRNAs or otherwise suppress the expression of these mRNAs in the cytoplasm, redundancy in the RNA binding sites would be desirable. This is especially true in highly differentiated tissues like neurons, where expression of growth regulatory proteins could be deleterious. The present in vitro RNA binding studies suggest that Hel-N1 binds to c-myc and GM-CSF 3' UTRs in a multimeric fashion such that the entire RNA may be covered with protein. Thus, the 3' UTR may contain protein entry sites for nucleation of assembly which results in sequestration of the RNA. Whether this results in dysfunction of the mRNA or recruitment of other proteins (eg. nucleases) is not known. Yeast poly A binding protein, which is related to Hel-N1 in sequence, has been shown to recruit a specific endonuclease for deadenylation (J. E. Lowell, et al, *Genes & Devel.* 6: 2088 (1992)). Such a model is consistent with dozens of attempts to transfect Hel-N1 into cultured cells, which have repeatedly failed. On the other hand, transfection with the third RNA-binding domain of Hel-N1 resulted in rapid growth of 3T3 cells. Thus, Hel-N1 is thought to be a suppressor of mRNA expression of growth regulatory genes and can serve as a master recognition protein of 3' UTR sequences. Although the mechanism of its suppression is not known, its broad binding properties suggest that it probably affects mRNA expression through sequestration, translatability or instability.

Gaining access to novel growth regulatory genes

The present invention provides a method to use mRNA binding proteins which have multiple target sites among a functionally related subset of cellular mRNAs to gain access to the subset. This is a potentially powerful tool. Current methods for finding growth regulatory genes requires 1) biological or biochemical analysis or extraction; 2) homology probing or expression cloning; or 3) random sequencing of genomes. The first two approaches are intellectually systematic based upon investigative reductionism, but are slow and methodical. The last is a brute force approach without any functional rationale for finding or recognizing the end products except by homology. The ability to partition messenger RNA populations from any particular cell type using RNA-binding proteins which target multiple structurally and/or functionally related sequences should allow rapid access to important human genes, which otherwise are dispersed all over the human genome. It is highly probable that information obtained concerning the nested sets of growth regulatory genes will rapidly advance knowledge concerning basic mechanisms of growth, development and disease.

By using an RNA binding protein, such as the Hel-N1 RNA binding protein of the present invention, to perform an mRNA screen on total cell or tumor messenger RNA, one can obtain a partitioned subset of related messenger RNAs which then can be used in a variety of ways. The subset of mRNAs can be translated into their corresponding proteins by in vitro or in vivo techniques and the resulting group of proteins analyzed by two-dimensional gel electrophoresis to determine a fingerprint for the particular subset of proteins obtained. (FIG. 13) In the case of growth regulatory proteins obtained by Hel-N1 mRNA partitioning, the fingerprint obtained by the two-dimensional gel electrophoresis would provide an efficient diagnostic method for determining inbalances in growth regulatory proteins and the efficacy of various treatments to correct any inbalance.

From among the RRM proteins listed in Query et al, *Cell* 1989 and in U.S. application Ser. No. 07/436,779 to Keene et al, most are known to have binding specificity for polyadenylate or small nuclear ribonucleic acids (eg. U1, U2, etc.) transfer RNAs, 5S or 7S RNAs. Most RRM proteins do not have RNA binding targets that have been identified. Thus, any of the potential mRNA-binding RRM proteins listed in these references or in Kenan et al, *TIBS,* 1991 are candidates for being 3' UTR binding proteins useful for partitioning structurally or functionally-related subsets of messenger RNA. They include but are not limited to hnRNP proteins (A, B, C, D, E, F, G, H, I, K, L), RRM proteins CArG, DT-7, PTB, K1, K2, K3, K3, HuD, HUC, elav, rbp9, eIF4B, sxl, tra-2, AUBF, AUF, 32KD protein, ASF/SF2, U2AF, SC35, and others from the Kenan review.

Although authors have speculated about the nature of the binding targets for some of the RRM proteins (eg. polypyrimidine references preferences or homopolymeric binding in introns) no unique targets or specific binding sequences have been elucidated. More importantly, no RRM protein has been found to specifically target 3' untranslated sequences on multiple mRNAs until the present inventors discovered the specificity of HelN1 for 3'UTRs of growth regulatory mRNAs, including proto-oncogene and cytokine mRNAs.

One of ordinary skill would know which of these proteins to use by either:

1) using the random selection method shown in FIG. 11 as from D. E. Tsai et al, *Nuc. Acids Res.* 19: 4931 (1991) and T. D. Levine et al, *Mol. Cell Biol.* 13: 3494 (1993) and the parent of this application;

2) applying the method described in this patent application and sequencing the cDNA subset library.

Alternatively, the subset of messenger RNAs obtained using the screening procedure could be used to prepare a subset or library of functionally related genes, thus enabling chromosome mapping and genome sequencing of these functionally related genes.

Figure 13:
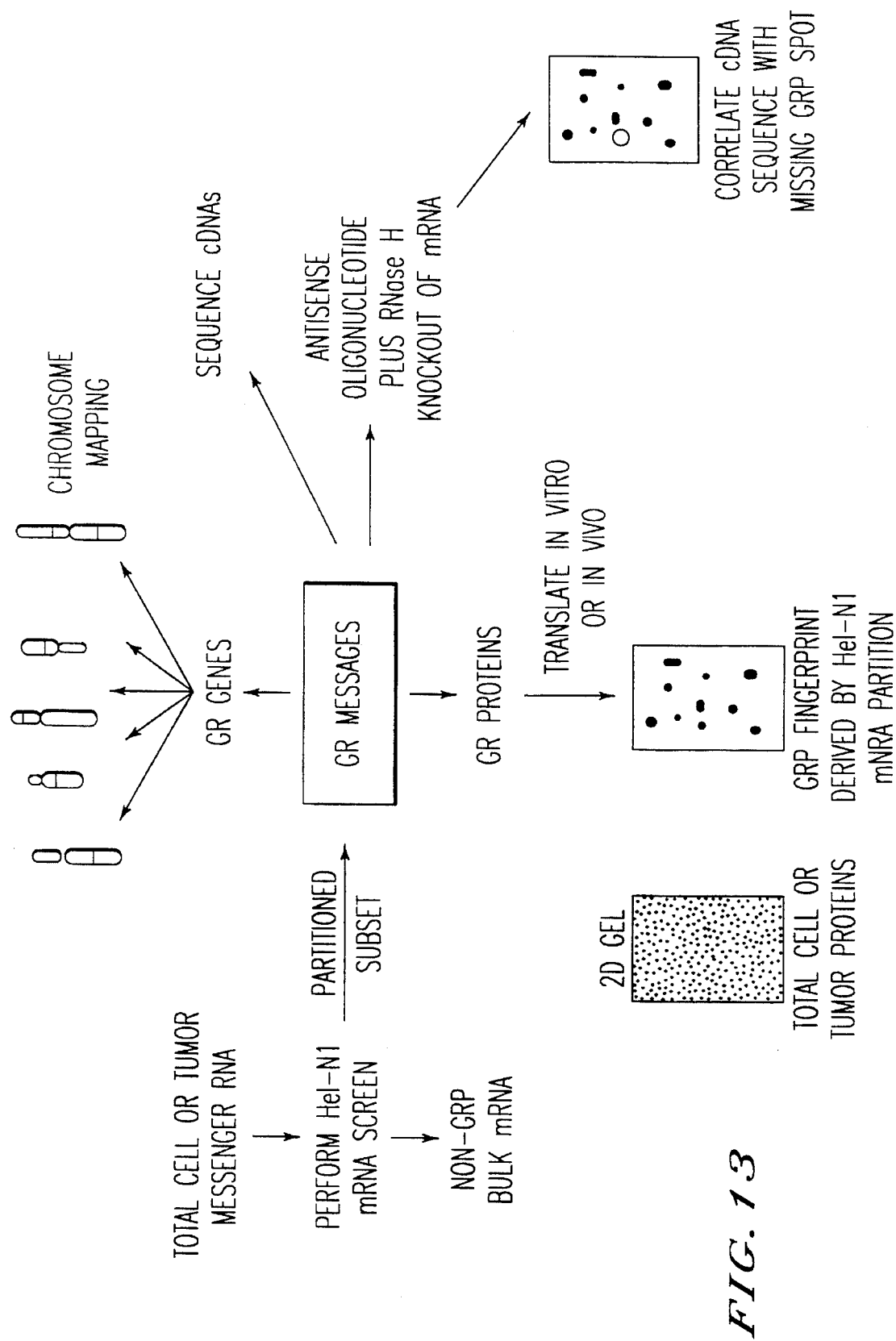
FIG. 13 provides a schematic showing the various uses of the partitioning method of the present invention.

In an additional embodiment, the cDNA sequences for each of the subset of mRNAs could be obtained and each of these cDNAs systematically correlated to the particular corresponding protein of the subset by the use of antisense oligonucleotides in combination with an RNase in order to specifically knock out one of the messenger RNAs of the subset, followed by two-dimensional gel electrophoresis of the in vivo or in vitro translated protein (FIG. 13). Thus, after the electrophoresis is run, one would obtain a characteristic pattern or fingerprint for the subset in which one of the spots signifying the targeted protein would be missing. Such a procedure can be used to identify and map the growth regulatory proteins which characterize a given cell, tissue or tumor.

Having generally described this invention, a further comparator can be obtained by reference to certain specific examples which are provided herein for purpose of illustration only and are not intended to be limiting unless otherwise specified.

Hel-N1 and a rat cDNA, Rel-N1, appear to be homologous to Drosophila elav within the RNA recognition motifs; however, these proteins differ markedly in other regions. Analysis of mRNA expression in rat tissues demonstrated that Rel-N1, like elav, was specific to brain tissue. In situ hydribization localized Rel-N1 mRNA to neurons of the hippocampus and neocortex, but not to Purkinje cells, glial cells, or white matter.

The mRNA of the rat counterpart of elav was found to reside in a subset of neurons in the brain. It was not detected in glial cells or white matter and was found within the hippocampus and cerebral cortex of the rat. Using in vitro RNA binding methods, it was found that the human counterpart, Hel-N1 (Human elav-like Neuronal protein-1) could bind in vitro to the 3'-untranslated regions (3'-UTR) of certain mRNAs, including the mRNA "instability regions" of c-myc, c-fos and GM-CSF mRNA.

These growth regulatory proteins are known to play important roles in cell proliferation, differentiation and immunoregulation. Thus, these observation show that Hel-N1, and perhaps other members of the elav sub-family, represent tissue-specific transacting factors involved in post-transcriptional mRNA metabolism.

Rat and human cDNA counterparts of the Drosophila neuronal protein, elav, were isolated using degenerate oligonucleotides, PCR, and library screening. RNAs capable of binding the human neuronal protein, Hel-N1, include 3'-UTRs of mRNAs encoding the oncoproteins, c-myc and c-fos and the lymphokine, GM-CSF. These RNA sequences encompass the "instability region" that is known to correlate with lability of these mRNAs (Meijlink et al, *Proc. Nat. Acad. Sci. (USA)* (1985) 82: 4987–4991; Shaw et al, *Cell* (1986) 46: 659–667; Jones et al, *Mol. Cell Biol.*, (1987) 7: 4513–4521).

RNA binding results were obtained using recombinant Hel-N1 followed by: (1) selection of uridylate stretches from a degenerate pool of RNAs, (2) immunoprecipitation of c-myc, c-fos and GM-CSF mRNAs using two types of Hel-N1-specific antibodies, and (3) crosslinking to c-myc and GM-CSF 3'-UTR with uv light. The 3-UTR of these mRNAs are U-rich, but also contain other identifiable features of primary sequence. For example, the pentameric sequence, AUUUA defined by Malter *Science* (1989) 246: 664–666 and the octameric sequence, UUAUUUAU proposed by Caput et al, (1986), are common among the 3'-UTR of these mRNAs. These findings indicate that Hel-N1 and related proteins participate in the post-transcriptional regulation of unstable messenger RNAs.

Shaw et al *Cell* (1986) 46: 659–667, demonstrated a role for the A/U-rich 3'-UTR of protooncogene and lymphokine mRNAs in the instability of the RNA. In addition, they demonstrated that instability could be conferred to otherwise stable mRNAs by placement of the instability region in the 3'-UTR.

However, it should be noted that other regions of certain mRNAs, including c-myc, c-fos, histone and transferin receptor, have also been implicated in destabilizing their mRNA (reviewed by Cleveland and Yen, 1989; Atwater et al, 1990). Verma and coworkers (Meijlink et al, 1985) demonstrated that removal of the 3'-UTR from c-fos mRNA resulted in increased levels of c-fos protein and cell transformation.

These studies show that regulatory events at the 3'-UTR are important for growth control. However, the A/U-rich 3'-UTR sequences span hundreds of nucleotides and the precise sequences involved in instability have not been identified. Recent work suggests that the AUUUA sequences are not required for instability, but that an upstream secondary structure in the 3'-UTR is more important. Thus, the role of the sequence elements within the 3'-UTR of these protooncogene and lymphokine mRNAs are not clearly defined at this time.

Proteins that interact with the 3'-UTR of oncoprotein and lymphokine mRNAs are poorly understood. Cross-linking with UV light and label transfer experiments by Vakalopoulou et al, *Mol. Cell. Biol.* (1991) 11: 3355–3364, noted a 32 kD protein that binds this region. Malter, *Science* (1989) 246: 664–666, observed a factor composed of three subunits, termed AUBF, in Jurkat cells that crosslinked to four repeats of the pentameric AUUUA sequence. More recently, Myer et al, *Proc. Nat. Acad. Sci. (USA)* (1992) found that small RNA transcripts from herpes simplex virus contain the AUUUA sequence and are capable of being UV cross-linked to the 32 kD protein from HeLa cell extracts. These findings suggest that there may be many proteins capable of recognizing sequences in the 3'-UTR. To date, none of these proteins have been defined biochemically as to amino acid sequence or precise RNA target sequence. The binding specificity of Hel-N1 to the 3'-UTR of c-myc, c-fos, GM-CSF represents the only defined RNA-protein interaction in this region.

Using an in vitro RNA degradation assay Brewer (1991) identified and partially purified an activity termed, Auf, from human erythroleukemia cells that appears to be involved in instability of c-myc mRNA. Based upon a mobility shift assay, he postulated that proteins of 37 kD and a 40 kD present in these fractions were involved in binding to c-myc RNA. Although these factors were implicated in instability, they have not been characterized as to sequence or binding specificity.

Hel-N1 represents an amino acid sequence containing an RNA-binding domain that can recognize and bind to 3'-UTR of mRNAs containing the instability sequence. It is possible that Hel-N1 represents a neuron-specific counterpart of one of several proteins shown to bind A/U-rich 3'-UTR sequences in UV crosslinking studies. Given that it contains three different RRMS, it is possible that Hel-N1 functions as a structural component of an RNP which interacts in the 3'-UTR through one or more RNA binding domains and carries another small RNA to that site. Alternatively, the RNA binding domains could perform a structural role in RNA bridging interactions as proposed for the U1 snRNP-A protein (Lutz-Freyermuth et al, *Proc. Nat. Acad. Sci. (USA)* (1990) 87: 6393–6397) or as an RRM combinatorial, synergistic mode as shown for the hnRNPA/B-type proteins (Tsai et al submitted).

As an RNP, an RRM combinatorial or a bridging protein, Hel-N1 (or related proteins) may play a role in other post-transcriptional processes such as mRNA compartmentalization or translation. By this analogy, Hel-N1 may be involved in neuron-specific localization or functional supression of mRNAs in the central nervous system.

Thus, members of the elav subfamily might recognize similar subsets of RNAs, but be functionally distinct based upon other differences in their amino acid sequences. Expansion of the subfamily and determination of the tissue specificity and developmental regulation of each member will be required to address these possibilities.

Hel-N1, like HuD, was observed by the inventors to be reactive with an autoantibody present in the sera of patients with paraneoplastic disease, putting it in the category of other human autoantigens that are members of the RRM superfamily (Saitta et al, *Rheumatology Clinics of North America*, D. Pisetsky, ed., pp. 1–25 (1992)). The potential to bind to oncoprotein mRNAs adds an element of intrigue because these patients are a subset of those inflicted with small lung cell carcinoma in which levels of c-myc protein are elevated. However, the mechanism of initiation of the autoimmune response to these self antigens remains as elusive as that of the systemic snRNP autoantigens. In addition, there is no evidence that Hel-N1 or HuD play a role in the derivation of the paraneoplastic syndrome or of small cell carcinoma. Additional information concerning the influence of Hel-N1 and related proteins on the production of cellular growth factors will be required to argue for such a link.

cDNAs encoding a variety of putative RNA-binding proteins were isolated by probing with degenerate oligonucleotides derived from conserved portions of the RRM (Query et al, *Cell*, 1989, ibid). For members of the RRM family that contain multiple RRMs, oligonucleotides derived from the sequence of the RNP1 octamers were used. Primers representing sense and antisense strands of the RNP 1 of RRM 1 and the RNP 1 of RRM 2 of elav DNA (Robinow et al, *Science* (1986) 242: 1570–1572) were used to probe mRNA from rat pup brain following reverse transcription with random primers. A PCR product was isolated and found to contain an ORF with an amino acid sequence termed, Rel-N1, which was, in turn, used to screen a human fetal brain library under high stringency conditions. A 2.2 kD DNA insert containing an open reading frame (ORF) of 359 amino acids was obtained. In vitro transcription and translation of the human cDNA produced a protein, termed Hel-N1, of the predicted size. Hel-N1 were identical in amino acid sequence and greater than 92% homologous in nucleic acid sequence.

Figure 2A:
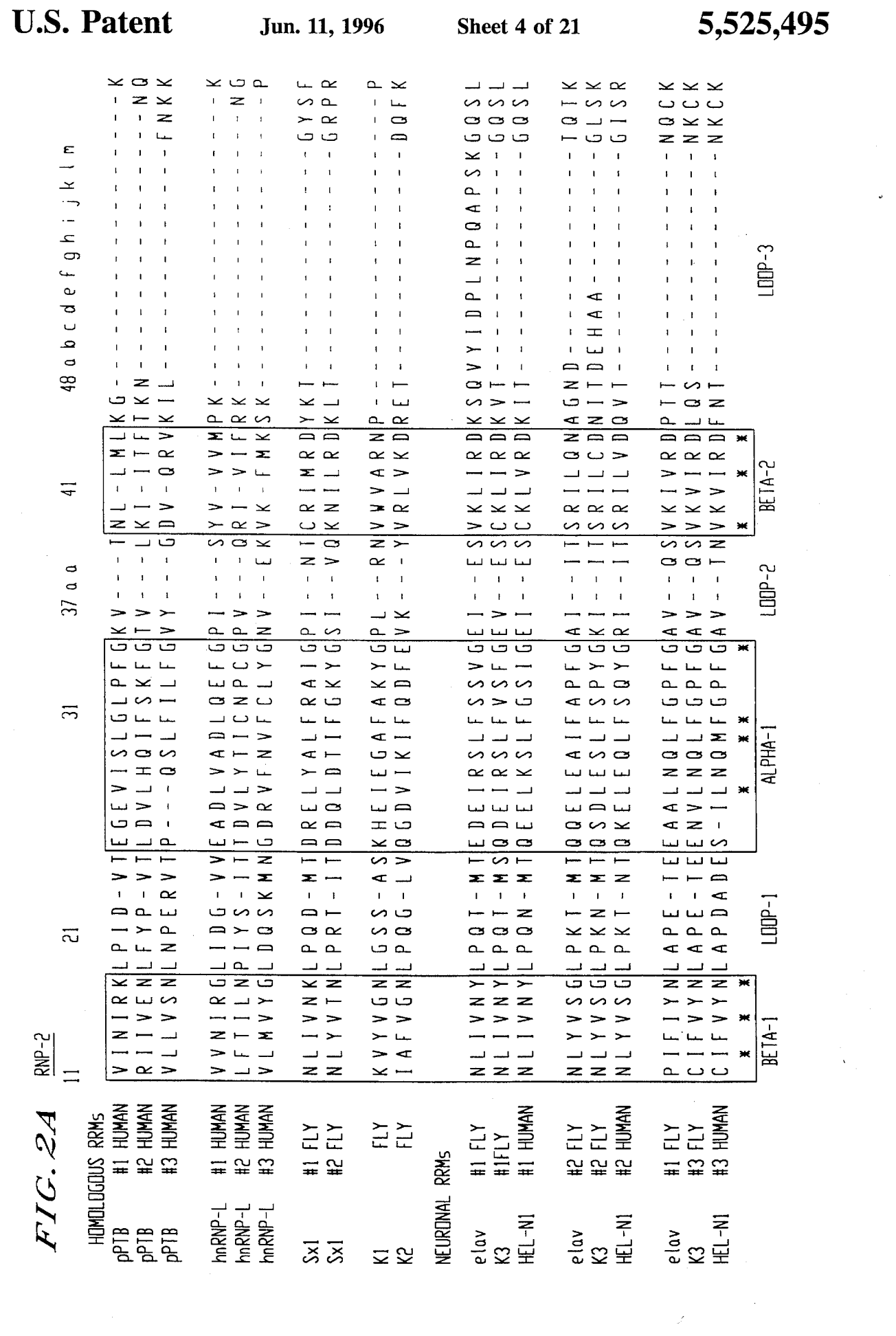
Figure 2B:
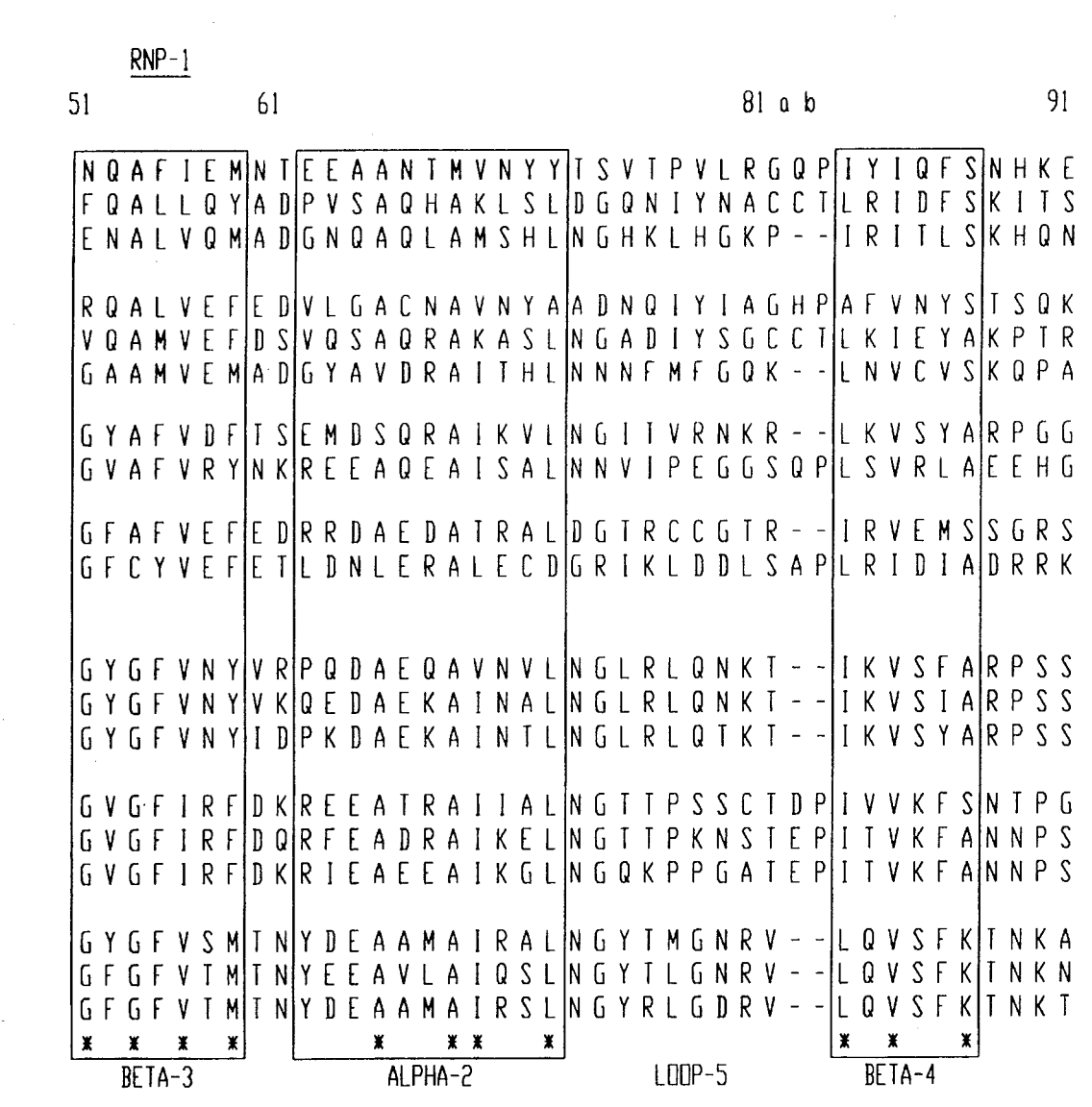

As shown in FIGS. 1 and 2, Hel-N1 contains three potential RNA binding domains as evidenced by RRMs 1, 2 and 3, which matched the structural criteria of Kenan et al (1991), supra, and each contained an RNP1 octamer (boxed and shaded) and an RNP2 hexamer (boxed) sequence. Sequence comparison of elav and the related Drosophila protein, K3, with Hel-N1, revealed strong similarities in the RRMs (FIGS. 1 and 2). On the other hands, Hel-N1 was only 76% the length of elav because the region amino terminal to the first RRM of the proteins demonstrated striking sequence differences (FIG. 1).

The amino terminus of Hel-N1 lacks the homopolymeric stretches of alanine, asparagine and glutamine seen in the amino termini of elav and K3, leaving it considerably shorter in length. This divergence is of unclear significance, especially in light of rescue studies done in Drosophila bearing the lethal mutation elavE5. These studies demonstrated that deletion of a 40 amino acid portion in the amino terminal does not prevent rescue from lethality. Thus, elav, Hel-N1 and K3 represent members of a subfamily of the RRM superfamily of RNA-associated proteins (Kenan et al, (1991), supra. This shows the existence of an elav-like subfamily of RNA binding proteins and, except for authentic elav, they can be designated by species as human (H) or rat (R) and tissue specificity as neuronal (N) of origin.

Kenan et al, *Trends. Biochem. Sci.* (1991) 16: 214–220, have proposed that pPTB and hnRNP-L represent a distinct subset of the RRM superfamily of RNA binding proteins in that they lack the characteristic RNP 1 and RNP 2 sequences. Also evident in FIG. 2 are the sequence differences in loop 3 that connects β-strand 2 to β-stand 3 (RNP 1). Loop 3 has been described as highly variable among RRM family members (Bentley et al, *Mol. Cell. Biol.* (1991) 11: 1829–1839. In the case of the U1 snRNP-A protein, sequences residing in loop 3 were shown to affect the specificity of RNA recognition (Bentley et al, 1991; reviewed in Kenan et al, 1991); thus, representing one determinant of specificity. It is apparent that Hel-N1 differs from elav most strikingly in RRM 1, while RRMS 2 and 3 are highly similar (FIG. 2). This may indicate that the potential RNA-binding domains at RRM 1 of elav and Hel-N1 recognize different RNA ligands.

Rel-N1 is neuron-specific

RNAs extracted from various rat tissues were analyzed by ribonuclease protection assays using Rel-N1 as probe. Protected bands were found only in RNA from rat brain; however, longer exposures revealed a small amount of RNA detectable in rat testes. To identify the specific neuroanatomic loci expressing Rel-N1 mRNA, 4% paraformaidehyde-fixed rat brain sections were hybridized with [35S]-labeled antisense RNA derived from the PCR fragment of Rel-N1 using the method of Fremeau et al, *EMBO J* (1990) 9: 3533–3538.

Data (King et al. *J. Neurosci.*, in press) revealed that Rel-N1 mRNA was heterogeneously distributed in adult rat brain. Prominent hybridization signals were observed throughout all layers of the cerebral cortex and within the hippocampus. High levels of expression were observed in the CA3-CA4 fields of Ammon's Horn. In contrast, only low levels of expression were observed in the CA1 field of Ammon's horn and the granule calls of the dentate gyrus. Prominent hybridization signals were also observed throughout the thalamus and brainstem. Particularly intense hybridization signals were observed in the parafascicular and midline thalamic nuclei. In the cerebellum, only a small percentage of labeled cells were observed in the granule cell layer while only background labeling was observed over the molecular layer, the Purkinje cell layer, and the white reafter tracts. Grains were not observed over the choroid plexus, ependymal cells of the cerebral ventricles, and control sections hybridized with a sense-strand probe.

In sum, these data indicate that Rel-N1 mRNA is expressed most highly in the hippocampus and cerebral cortex, as well as in certain neurons in the granule cell layer of the cerebellum, but not in Purkinje cells of the cerebellum.

Given that the RNA binding ligands are not known for any of the four known elav sub-family members, several standard RNA binding assays (Lerner et al, *Proc. Nat. Acad. Sci. (USA)*, (1979) 76: 5495–5499) using total 32P labeled RNA isolated from HeLa, glioblastoma and neuroblastoma cells were attempted. In addition, in vitro RNA binding procedures which have been used effectively for other members of the RRM family of proteins (Query et al, *Cell* (1989) 57:

89–101; Lutz-Freyermuth et al, *Proc. Nat. Acad. Sci. (USA),* (1990) 87: 6393–6397; Bentley et al, 1991) did not reveal a cognate RNA species for Hel-N1.

As an alternative approach, we used a random RNA selection procedure to define the RNA ligand site for Hel-N1. A synthetic oligodeoxynucleotide containing a stretch of 25 degenerate nucleotides was used to create a large heterogeneous pool of RNA sequences for selection of binding ligands (Tsai et al, *Nucl. Acids Res.* (1991) 19: 4931–4936). Binding of the degenerate RNA pool to recombinant Hel-N1, followed by immunoprecipitation of the complex using the epitope tag, g10, was carried out as described previously (Lutz-Freyermuth et al, 1990; Bentley et al, 1991).

After three complete cycles of binding and selection, 30 independent clones, representing individual coimmunoprecipitated RNA species were evaluated by sequence analysis. The sequences of the bound RNAs showed a preponderance of uridylate residues in short stretches interrupted by other nucleotides. However, two of the 30 sequences (B-17 and B-5) did not contain this U-rich pattern. These variants were rare in the population and thus, may represent ligands of lower binding affinity. Alternatively, because Hel-N1 contains three potential RNA binding domains, these other sequences may represent ligands which were bound by one of the domains not involved in recognition of the U-rich regions. This possibility is compatible with the proposal that Hel-N1 may exist as an RNP that bridges between two or more RNAs via its multiple RRMs as proposed for the U1 snRNP-A protein (Lutz-Freyermuth et al, 1990). It remains possible that RRMs 1 and 2 of Hel-N1 bind to sequences in the 3'-UTR, perhaps augmenting the binding of RRM 3.

This random RNA selection procedure has proved useful in our laboratory with other members of the RRM family of proteins to derive RNA ligand consensus sequences (Tsai et al, 991), but in no other case has a short stretch U-rich sequence been selected. In the experiments using Hel-N1, RNA sequences with a U-rich character were derived using the selection procedure, but a single consensus sequence was not evident.

The sequences selected from the in vitro RNA selection protocol were suggestive of biologically relevant sites known to exist in mammalian RNAs such as 3' UTRs in labile RNAs, the polypyrimidine tract near 3' splice junctions, sequence 5' of the polyadenylation signal, and in mitochondrial telomeres. The most striking feature was that short uridylate stretches flanked by either A, G or C could be located within the 3' UTRs listed by Shaw et al, *Cell* (1986) 46: 659–667 in their study of the instability sequences of proto-oncogene and lymphokine messenger RNAs. Thus, we conducted a series of direct RNA binding experiments to examine this possibility.

DNA constructs encoding portions of the 3' UTR of c-myc, GM-CSF, and c-fos mRNAs were used to synthesize radiolabeled transcripts for binding to recombinant Hel-N1 protein using our standard methods (Bentley et al, 1991). We utilized $^{32}P$ labeled transcripts corresponding to the 3' UTR sequences, as well as to a variety of unrelated RNAs. As with the RNA selection procedure used above, Hel-N1 was fused to the g10 epitope for precipitation. c-fos, GM-CSF and c-myc transcripts were precipitable, while other transcripts were not precipitable.

The specificity of Hel-N1 binding to 3'-UTR of c-myc, GM-CSF, and c-fos 3' UTR was substantiated by the use of many control RNAs including total HeLa cell RNA, transcripts of various small RNAs, precursor mRNAs, various vector RNA transcripts and other RNAs. In addition, RNA binding was always in the presence of carrier transfer RNA and poly A (Query et al, 1989; Bentley et al, 1991).

Control transcripts for RNA binding specificity also included hY3 antisense RNA that contained a single AUUUA pentamer. This sequence has been suggested to represent the most conserved element present in the 3' UTR of the unstable protooncogene and lymphokine RNAs (Shaw et al, Cell (1986) 46: 659–667; Caput et al, (1986); Malter, *Science* (1989) 246: 664–666. Vakalopoulou et al, *Mol. Cell. Biol.* (1990) 11: 3355–3364, showed previously that the specificity for binding of these 3' UTRs to a 32 Kd protein present in Hela nuclear cell extracts resided in multiple copies of an AUUUA motif contained within a uridylate-rich region.

It should be noted that the hY3 RNA did not contain a uridylate-rich region surrounding the AUUUA. N-myc was also used as a control transcript because it contained a stretch of thirteen uridylates, but no AUUUA pentamer. None of these various control RNAs were significantly immunoprecipitated indicating that binding to Hel-N1 did not occur.

Among the control transcripts, we employed precursor mRNA-in-pieces (PIP vectors) which encode uridylate-rich stretches of RNA that are active in in vitro splicing and can be cross-linked with uv light to pPTB (Garcia-Blanco et al, 1990), supra. PIP transcripts also failed to bind Hel-N1. Several other RNA transcripts failed to bind Hel-N1 including coding regions of N-myc mRNA, U1 RNA, a transcript encoding neomycin resistance, noncoding regions of U1 snRNP-70K mRNA, and coding regions of the dopamine 1 receptor.

In these studies, RNAs in the supernatants of the binding reactions were analyzed for the presence of intact non-bound RNA to rule out degradation. Although Hel-N1 binding to other untested U-rich sequences remains a possibility, its preference for the instability sequences at the 3' UTR of c-myc, GM-CSF, and c-fos mRNAs was compelling.

As an alternative confirmation of the RNA-binding specificity of Hel-N1 with the 3'-UTRs of these rapidly degraded mRNAs, label transfer experiments involving uv crosslinking with 32P labeled RNA were performed using standard procedures. HeLa cell nuclear extract and recombinant Hel-N1 in an *E. coli* extract were incubated with 32P labeled c-myc or GM-CSF mRNAs and exposed to UV light to mediate covalent cross-linking between the RNA and associated proteins. After cross-linking, excess RNA was digested with RNase A and analyzed on an SDS-acrylamide gel.

The label transfer to Hel-N1 revealed two predominant bands of 70 kD and 28 kD; similar results were obtained with GM-CSF (data not shown). The higher molecular weight band was found to be an artifact of IPTG induction, since control *E. coli* extracts lacking Hel-N1 also showed the 70 kD cross-linked band. The 28 Kd band (termed Hel-N1') was 10 Kd smaller than the expected size of Hel-N1. While it is possible that the bound RNA or the cross-linking protocol caused Hel-N1 to migrate aberrantly, we observed that the 28 Kd band contained Hel-N1 epitopes (see below).

Direct label transfer experiments using HeLa cell extracts and radiolabeled c-myc mRNA demonstrated the ability to uv crosslink several proteins similar to that reported by Vakaloupoulu et al (1991). To determine whether Hel-N1 can compete with cross-linked proteins in the HeLa cell nuclear extract for binding to c-myc, increasing amounts of Hel-N1 were added prior to UV exposure. Neither the 32 kD protein identified by Valakopoulou et al (1991) nor hnRNP C protein (45 kD) diminished significantly upon addition of Hel-N1. In addition, the 28 kD Hei-N1 band (Hel-N1') appeared during the crosslink competition.

These results indicate that Hel-N1, the 32 kD protein, and hnRNP-C protein can bind simultaneously to the 3'-UTR of c-myc MRNA. On the other hand, a band of 65 kD was competed by Hel-N1, while E. coli extracts lacking Hel-N1 had no effect. The identity of the competed 65 kD protein remains unknown. These data suggest that while the HeLa 32 Kd protein and hnRNP C may share similar RNA binding characteristics with Hel-N1, their binding sites as defined by uv crosslinking are not identical.

Recent studies into several paraneoplastic neurologic disorders including paraneoplastic sensory neuropathy (PSN), paraneoplastic cerebellar degeneration (PCD), and paraneoplastic encephalomyelitis (PEM) have reported the identification of several antigens recognized by the sera of patients with these disorders (Dropcho et al, *Proc. Nat. Acad. Sci.(USA)* (1987) 84: 4552–4556; Anderson et al, *Neurology* (1988) 38: 1018–1026; Dalmau et al, *Ann. Neurol.* (1990) 27: 544–557; Szabo et al, *Cell* (1991) 67: 325–333).

One such antigen, HuD, displays strong similarity to recombinant Hel-N1, but possesses important differences. Both HuD and Hel-N1 contain three RRMs which share approximately 70% overall homology. The major differences exist in the amino termini and in a stretch of thirteen amino acids between the second and third RRMs.

Using anti-HuD sera, we demonstrated cross reactivity with Hel-N1 by Western blotting. When used in the RNA binding protocol in place of the g10 serum, an anti-Hu serum was found to immunoprecipitate c-myc transcripts that bound to Hel-N1 in vitro. Control RNAs did not bind Hel-N1. Furthermore, four normal human sera lacked the ability to immunoprecipate these mRNPs. These experiments demonstrate that the complex formed between HuD antibodies and Hel-N1 does not interfere with the ability of the protein to recognize its RNA ligand.

To confirm the antiHuD RNA binding assay, the label transfer experiments using cmyc 3'-UTR and g10-Hel-N1 as described above were followed by immunoprecipitation of the 28 Kd Hel-N1' band with HuD sera. Normal human sera were always negative. In addition, the 70 Kd *E. coli* band was not immunoprecipitated by any of these sera, as expected of the nonspecific *E. coli* protein. These data show that HuD sera can also immunoprecipitate a preformed complex of RNA bound to Hel-N1. Thus, Hel-N1, and presumably HuD, appear to possess autoantigenic epitopes that are distinct from the RNA-binding domain(s) that recognize the uridylates.

It is interesting to note that the 28 Kd band (Hel-N1') was immunoprecipitated with the HuD sera, but not with the g10 serum or normal sera. Thus, it was assumed that the amino terminus was lost by cleavage. Estimation of the resultant size of Hel-N1' suggests that cleavage occurred at a site C-terminal to the first RRM, leaving a fragment containing RRMs 2 and 3. The source of this unexpected cleavage event is currently under investigation. These results suggest that the interaction between c-myc mRNA and Hel-N1 is specific to the second or third RRM; one of which may constitute the RNA binding domain.

Experimental Procedures
Cloning Rel-N1 and Hel-N1 by PCR and hybridization

Degenerate PCR primers were synthesized based on the first seven amino acids of the RNP1 consensus sequence in the first (sense) and second (antisense) RRMs of elav. Inosine residues were placed in positions degenerate for all 4 nucleotides and Eco R1 restriction sites were placed at the 5' end of each oligonucleotide. cDNA was prepared by reverse transcribing total cytoplasmic RNA from a Sprague-Dawley rat pup brain according to the manufacturer's specifications (Cetus®): 6mg total RNA, 1 mM dNTPs, 100 picomoles of random hexamers (Pharmacia®), GeneAmp buffer, 20 U RNASIN (Promega®), 200U BRL reverse transcriptase. 40 cycles of PCR amplification were carried out using an annealing temperature of 37 and an extension temperature of 55 C. (cycles 1–4) and 72 (cycles 540). A PCR product of 281 bp was purified on a 1% agarose gel using Geneclean® (Bio 101) and subcloned into a TA vector (in Vitrogen®). The clone Rel-N1, was sequenced and found to have a high degree of homology with elav, including a 100% homologous RNP2 consensus sequence within the second RRM.

A random primed cDNA probe was generated using Rel-N1 and used to screen a λZAPII human fetal brain library (Stratagene®). Seven positive plaques were isolated from an initial population of 500,000 phage screened using the following hybridization conditions: 50% formamide, 6×SSC, 0.1% SDS and 0.01% Blotto. Filters were hybridized for 18 hours at 42 C. and then washed two times at room temperature (10 minutes each) in 2×SSC/0.1% SDS followed by a final wash at 65 C. in 0.2×SSC/0.1% SDS for 45 minutes. The Bluescript® plasmids of the positive phage were then isolated according to the manufacturer's specifications (Stratagene®).

Sequencing Hel-N1 cDNA

EcoR1 inserts within the Bluescript® plasmids were sequenced by exonuclease digestion and primer extension using the dideoxynucleotide chain termination with a modified T7 DNA polymerase from the Sequenase system (USB). Oligonucleotides were synthesized on an Applied Biosystems® 391 DNA synthesizer.

Expression of Hel-N1 in *E. coli*

An inducible T7 RNA polymerase expression system was used for production of Hel-N1 protein. By using PCR mutagenesis, a conservative point mutation was introduced into the carboxy portion of the ORF to delete an NcoI site, such that the only NcoI site remaining was at the translation-initiation methionine. An NcoI-EcoR1 insert from this construct was then subcloned in frame into pET-3c containing the T7 12-amino acid (g10) sequence at the 5' cloning site. After transfection of this construct into BL21(DE3)pLysS, the bacteria were induced with IPTG. The cells were washed twice in SM buffer and then resuspended in a small volume of *E. coli* lysis buffer (1 XTBS, 10 mM EDTA, 0.05% Tween, 3mM DTT and PMSF). Lysis was completed by freeze-thawing the cells. The extract was centrifuged at 10,000×g to remove insoluble debris. The amount of induction was evaluated by sodium dodecylsulfatepolyacrylamide gel electrophoresis and Western blotting as well as Coomassie staining.

In Situ Hybridization

In situ hybridization was conducted on 4% paraformaldehyde-postfixed adult rat brain sections as previously described (Fremeau et al, *EMBO J* (1990) 9: 3533–3538). Briefly, adult Sprague-Dawley rats were anesthetized with 300 mg of sodium pentobarbital, and killed by decapitation. Brains were removed and frozen on an aluminum block cooled with liquid nitrogen. Frozen sections (10 u) were prepared in a cryostat, mounted onto room temperature slides (Onasco Biotech®; Houston, Tex.) and stored at −70° C. until processed for in situ hybridization.

Tissue sections were thawed and fixed for 10 min in 4% paraformaldehyde in phosphate-buffered saline at 4° C. The sections were then rinsed in 2×SSC, covered with a minimal volume of 2×SSC, and illuminated with a germicidal UV-lamp (30 W, wide spectrum UV light) for 5 min at a distance of 30 cm. The sections were then rinsed in 2×SSC, and covered with prehybridization buffer (50% formamide, 0.6M NaCl, 10 mM Tris-HCl (pH 7.5), 0.02% Ficoll, 0.02% polyvinyl pyrollidine, 0.1% bovine serum albumin, 1 mM EDTA (pH 8.0), 50 ug/ml salmon sperm DNA, 500 ug/ml yeast total RNA, 50 ug/ml yeast tRNA and stored at 50° C. for 1 hr.

Prehybridization buffer was removed, and the slides were covered with hybridization buffer (50% formamide, 0.6M NaCl, 10 mM Tris-HCl (pH 7.5) 0.02% Ficoll, 0.02% polyvinyl pyrollidone, 0.1% bovine serum albumin, 1 mM EDTA (pH 8.0), 10 ug/ml salmon sperm DNA, 50 ug/ml yeast total RNA, 50 ug/ml yeast tRNA, 10 mM dithiothreitol, 10% dextran sulphate containing 35S-labeled probes ($2.5$–$5.0 \times 10^6$ cpm/ml; heat-denatured for 15 min at 65° C).

Hybridization was performed for 16–18 hrs at 50° C. Following hybridization, the sections were washed for 60 min in 2×SSC at 50° C. and then treated with RNase A (50 ug/ml) for 60 min at 37° C. The sections were then washed in 2×SSC for 60 min at 50° C. followed by a final high stringency wash in 0.1×SSC, 14 mM b-mercaptoethanol, 0.15% sodium pyrophosphate for 3 hr at 50° C., the heat was then turned off and the slides were allowed to gradually cool to room temperature overnight. The hybridized sections were dehydrated through graded ethanols containing 0.3M ammonium acetate, vacuum dried, and dipped in Kodak® NTB2 emulsion diluted 1:1 with $H_2O$. After 4–6 week exposure times, the slides were developed as previously described (Fremeau et al, 1990) and photographed under dark-field illumination with kodachrome 160 tungsten slide film (Kodak®).

RNA Probes

Rel-N1 cDNA was excised from the TA vector and subcloned into pGEM-3Zf(+) and linearized. $^{35}S$ (for in situ hybridization) or 32P (for RNAse protection assay) labeled single stranded antisense RNA probes were synthesized using T7 RNA polymerase in the presence of [35S]UTP (New England Nuclear®) or [32P]UTP (ICN). Sense RNA probe, made in a similar way, was used as a control for the in situ hybridization experiments. Unincorporated nucleotides were removed by G50 Sephadex (Pharmacia®) columns.

Ribonuclease Protection Assays.

Total cellular RNA was prepared from various tissues of an adult male Sprague-Dawley rat according to standard methods. Assays were carried out using 15 ug of total RNA from each tissue source essentially as described by Zinn et al *Cell*, 34, 865–879 (1983). Protected fragments were electrophoresed on a denaturing 5% polyacrylamide gel. The integrity of the RNA was ascertained by protection assay using 32P labeled antisense RNA transcribed from mouse β2-microglobulin cDNA.

RNA selection procedure

The RNA selection process was done according to the method described by Tsai et al (1991). Briefly, an oligodeoxynucleotide containing a T7 promoter sequence (T7Univ) at one end, followed by 25 degenerate nucleotides and then a reverse universal primer sequence (RevUniv) at the other end was used in a PCR reaction (1 min. 94, 1 min. 50, 2 min. 72 in 10 mM Tris-HCl (pH 8.3), 50 mM KCl, 1.5 mM $MgCl_2$, 0.01% gelatin, 0.1 mg of T7Univ and RevUniv primers, 200 mm dNTPs and 2.5 U of Taq DNA polymerase) to create double stranded template for transcription. RNA was synthesized using T7 polymerase using standard methods (*Maniatis*, 1990).

In binding conditions described previously (Query et al, 1989), the degenerate pool of RNA was then incubated with g10 -Hel-N1 fusion protein which had been prebound to protein-A beads (Sigma) using the g10 antibody. The beads were subsequently washed 5 times with NT2 buffer, and the immunoprecipitated RNA was then phenol extracted and ethanol precipitated in the presence of 10 ug of carrier tRNA (Sigma®). The RNA was resuspended in 10 ul of doubly distilled water, and 3 ul was used for PCR amplification under conditions described above. The T7 and RevUniv primers had Bam-H1 restriction sites incorporated in the 5' ends such that any multimer products were reduced to monomers with Bam-H1 digestion. The same process was then carried out two more times. After the final PCR amplification and Bam-H1 digestion, the product was subcloned into pGEM-3Zf(+) and sequenced.

Plasmids and mRNA transcripts

The 3' end of the GM-CSF gene (240 bp fragment between Nco I and Eco RI cleavage sites) inserted into the polylinker, pGem3 containing the 3' end of the human c-fos gene (250 bp RsaI-Tth111I) inserted into the Hinc II site, and pGem3 containing the NsiI-AflII fragment of the 3' end of the human c-myc gene were used. The plasmids were linearized as follows: GM-CSF in PSP64 was cut at BgIII and transcribed with Sp6 RNA polymerase; pGEM 3 containing c-fos was linearized with Kpn 1 and transcribed with T7 RNA polymerase; pGEM3 containing c-myc DNA was linearized with BamHI and transcribed with Sp6 RNA polymerase.

Linearized plasmid DNA was transcribed with SP6 RNA polymerase for c-myc and GM-CSF, or T7 RNA polymerase for c-fos. These reactions were carried out in the presence of 1.25 mm ATP, CTP, GTP; 0.75 mm UTP, and 5 ul of 1u Ci/ul 32P UTP.

RNA Binding to Hel-N1

For each binding reaction 4 mg of Protein A beads were washed three times in NT2 Buffer (150 mm NaCl, 50 mm Tris-HCl pH 7.4, and 0.05% NP40). 5 ul of rabbit anti-g10 antibody, or 20 ul of human serum, was incubated with Protein A for 10 minutes on ice and washed three times with NT2 buffer. 35 ul of Hel-N1 *E. coli* extract was then added and incubated for ten minutes on ice and washed three times with NT2 buffer. After the final wash, the protein complex was resuspended in 0.1 ml of RNA Binding Buffer and equimolar amounts of labeled transcripts were added.

After a 5 min. incubation at room temperature, the binding reaction was washed five times with NT2 buffer and resuspended in 0.1 ml of NT2 buffer. 0.1 ml of the supernatant from the first wash was saved and treated identically as the bound pellet. 0.1 ml of diethyl pyrocarbonate treated water was added as well as 13 ul of 5M NaCl and 1 ul of 10 mg/ml of tRNA. The reactions were PCI extracted and EtOH precipitated. The pelleted RNA was run on a 6% urea polyacrylamide gel.

UV Cross Linking

Hela cell nuclear extract was prepared as described by Dignam (1983) and label transfer from RNA to protein was carried out as described by Wilusz et al, *Cell* (1988) 52: 221–228. 500,000 cpm of labeled transcripts were incubated with 5 ug of nuclear extract in a total reaction volume of 10 ul. The reaction was performed in a microtiter plate and irradiated for 10 minutes on ice. RNase A was added for a final concentration of 1 mg/ml and incubated for 15 minutes at 37° C. The reactions were mixed with Laemmli buffer and run on a 10% SDS polyacrylamide gel.

Hel-N1 crosslinking was carried out as above, except that the protein was dissolved in a uv cross-linking buffer (20 mm Hepes, 1 mm $MgCl_2$, 60 mm KCl 10% glycerol). Competition experiments included 5 ug of Hela cell nuclear extract in the presence of increasing amounts of Hel-N1 maintaining a total reaction volume of 10 ul.

Cellular Growth

NIH 3T3 cells where transfected with a pBC vector derived from the CMV promoter containing DNA expression RNA binding domain 3 (RBD3) of Hel-N1 using the calcium phosphate method. Cells were co-transfected with a plasmid encoding resistance to neomycin and colonies were selected with neomycin in the growth medium. After approximately three weeks of selection cells were examined by immunoflorescence and found to express RBD3(–), while control cells transfected with neomycin resistance alone (+) did not express RBD3. Cells were counted at passage and planted on culture plates for determination of growth rate. At days 1, 2 and 3 a plate of each was sacrificed and the cell numbers determined. It was readily evident that those cells expressing RBD3 entered into rapid proliferation, while the control cells grew at the same rate as normal 3T3 cells.

Cellular RNA-Binding Targets

The present invention provides a proto-oncogene mRNA-binding protein, Hel-N1, that is a human neuronal counterpart of Drosophila ELAV (T. D. Levine et al, *Mol. Cell Biol.* 13: 3494 (1993); P. H. King et al, *J. Neurosci.*, in press). Mutations in the ELAV locus result in defective development of the nervous system of the fly with improper migration of neuroblasts and failure to fully differentiate (S. Robinow et al, *Dev. Biol.* 126:294 (1988); S. Robinow et al, *Science* 242:1570 (1988)). Binding of Hel-N1 in vivo to the 3' UTRs of certain oncoprotein and cytokine mRNAs has been shown above, but a cognate in vivo neuronal target was not identified. In practicing the present invention, Hel-N1 has been found to have multiple growth regulatory mRNA targets which can be directly coimmunoprecipitated with Hel-N1 from extracts of medulloblastoma cells or which can be bound in vitro to recombinant protein. These medulloblastoma tumor cells were found to express a deleted form of Hel-N1 (Hel-N2) that was not detectable in whole human brain which may indicate its correlation with rapid growth. However, a small amount of Hel-N2 was detected in mRNA from fetal brain, which may indicate its correlation with rapid growth. In addition, mRNA 3' UTR sequences that were able to bind to Hel-N1 using whole brain RNA and those which bound to Hel-N2 in medulloblastoma cells included previously identified growth regulatory factors such as nonreceptor tyrosine kinases and factors involved in the ras signal transduction pathway. Of fifty cDNA clones producing RNAs that bound to Hel-N1 or to Hel-N2, ten percent were identified as known growth regulatory proteins in the current databases.

In no case was a cDNA found that encodes a known protein that is not a growth regulatory factor. Thus, the forty five unidentified cDNAs appear to represent previously unknown growth regulatory proteins.

The mRNA-binding protein Hel-N1, has allowed the present inventors to gain access to a related set of cDNAs that encode growth-regulatory proteins. This is presumably because these constitute multiple 3' UTR targets for Hel-N1. Furthermore, Hel-N1 appears to function as a master recognition protein for growth factor mRNAs involved in cellular proliferation and differentiation.

Most growth regulatory proteins would be expected to be regulated by messenger RNA-binding proteins in the cytoplasm, but no proteins specific for these mRNAs have been cloned and demonstrated. It is reasonable to expect that mRNA-binding proteins involved in suppressing growth regulatory factors would be more prevalent in quiescent or highly differentiated cells than in rapidly growing cells. However, previous attempts to isolate proteins associated with proto-oncogene and cytokine mRNAs have utilized rapidly growing cells. Thus, being highly differentiated, with minimal ongoing proliferation, one might expect neurons to express proteins capable of suppressing expression of growth regulatory mRNAs. Evidence to date from the present invention indicates that Hel-N1 is the first such protein.

Cytoplasmic localization of Hel-N1 and related proteins

Figure 8A:
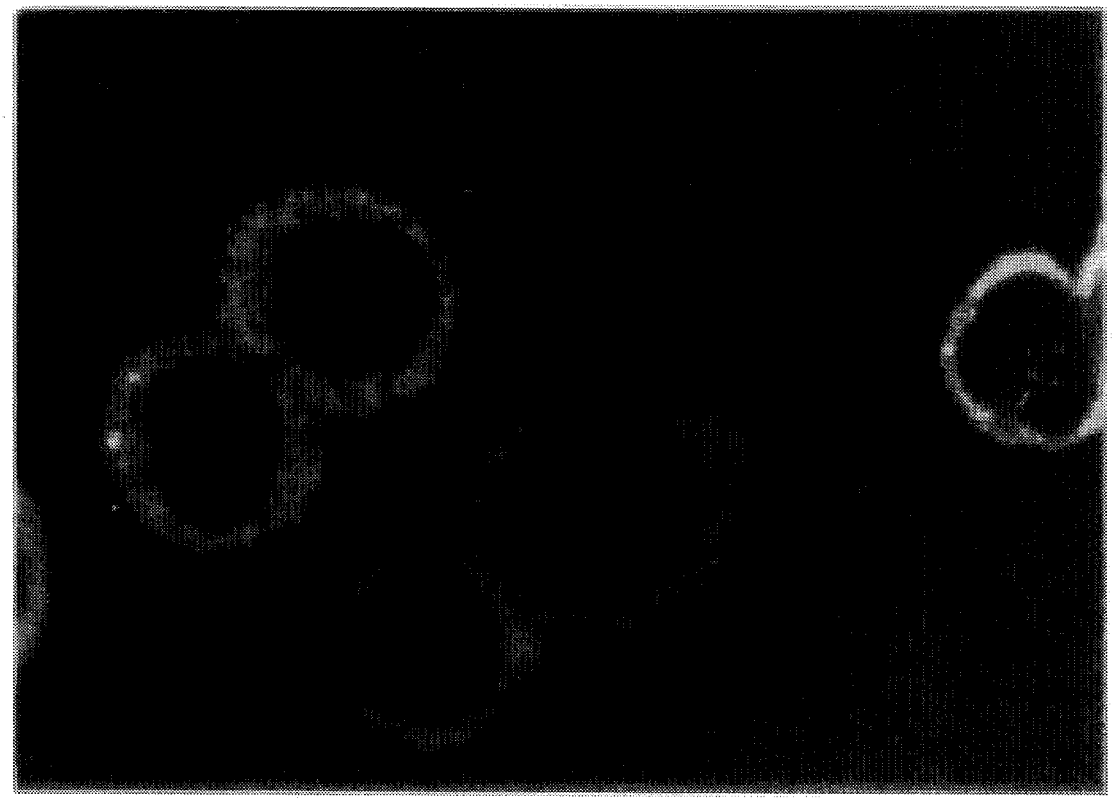
FIG. 8 shows the localization of Hel-N1 and Hel-N2 in human medulloblastoma cells. Panel A: Immunofluorescence using rabbit anti-Hel-N1 antibodies prepared against the partially purified recombinant protein described in T. D. Levine et al, *Mol. Cell Biol.* 13: 3494 (1993); P. H. King et al, *J. Neurosci.*, in press, and D. E. Tsai et al, *Nuc. Acids Res.* 19: 4931 (1991). Human medulloblastoma cell line D283 was obtained from Dr. D. Bigner, Department of Pathology, Duke University Medical Center (S. H. Bigner et al, *Cancer Res.* 50: 2347 (1990)). Panel B: Western blot analysis using rabbit anti-Hel-N1 antibodies. Lanes indicate the use of total cell extracts; cytosolic factions; or nuclear fractions from D283 cells. Panel C: Western blot analysis of the same fractions used in the panel B, but using hnRNP C-specific antibody to indicate the quality of the nuclear-cytoplasmic separation.
Figure 8B:
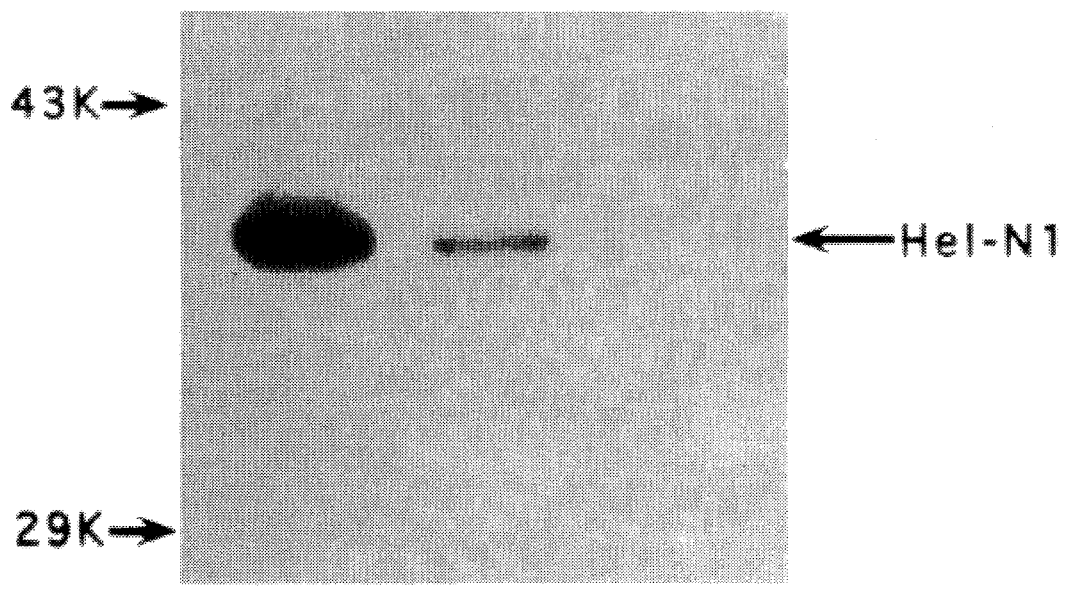
Figure 8C:
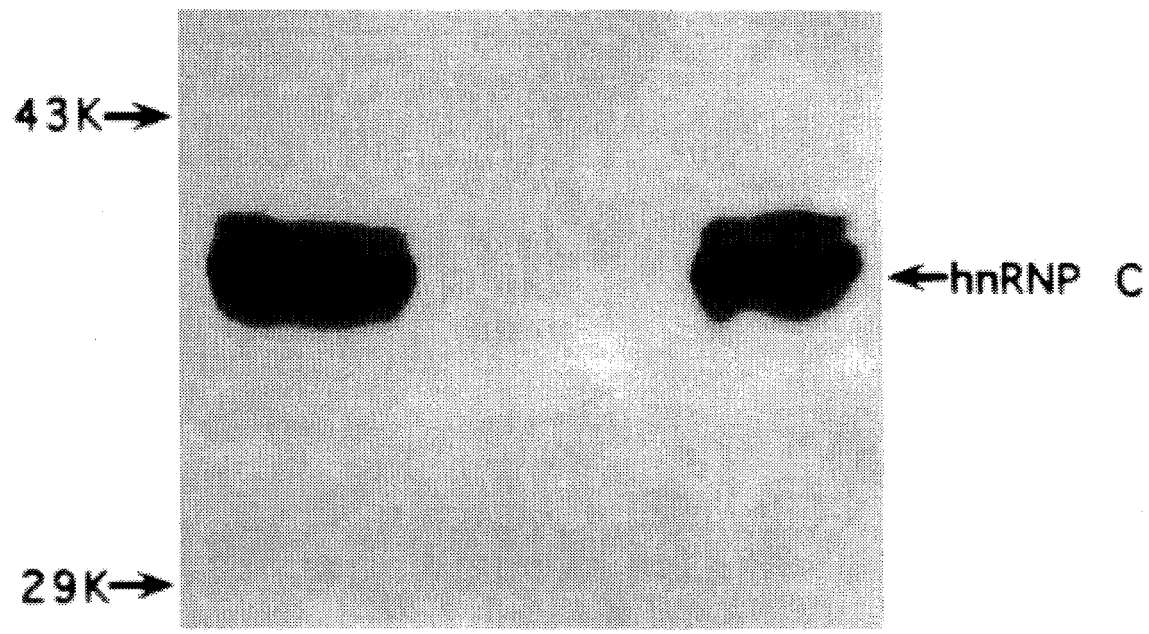

Examination of a variety of cell types for Hel-N1 and related proteins involved the use of rabbit antibodies prepared against the recombinant protein (S. Robinow et al, *Dev. Biol.* 126:294 (1988); S. Robinow et al, *Science* 242:1570 (1988)). Western blot analysis indicated that the antibody recognized proteins in certain neuroblastoma cells, small cell carcinoma cells and in childhood medulloblastoma cells. In order to examine the location of the Hel-N1 proteins in medulloblastoma cells immunofluorescence studies were performed. As shown in FIG. 8A, speckled cytoplasmic staining of these cells with only minor nuclear staining was evident. To confirm this finding cells were fractionated using standard methods and the nuclear and cytoplasmic fractions examined by Western blotting (FIG. 8B). It was clearly apparent that the antibody reacted with a cytoplasmic protein. As a control for both the fluorescence and the cell fractionation experiment, hnRNP C was determined to be strictly nuclear by biochemical fractionation (FIG. 8C) and by double fluorescence. Thus, the Hel-N1-specific antibody reacted with cytoplasmic components present in distinct speckled or granular particles.

Characterization of Hel-N1 in medulloblastoma cells

In order to determine the expression pattern of Hel-N1 in medulloblastoma cells, reverse transcription PCR was performed using oligonucleotide primers spanning the region between the highly conserved RRM 2 and 3 sequences defined by King et al.(P. H. King et al, *J. Neurosci.*, in press). Total cytosolic RNA was isolated from medulloblastoma cells and from control HeLa cells. As shown in FIG. 2, total brain RNA gave rise to a band of 188 nts. which is identical to that found previously using Hel-N1 cDNA as shown from the sequence of King et al. This band was evident in fetal brain and two medulloblastoma cell lines D283 and D341. This band was sometimes a doublet that presumably resulted from the reverse transcription reaction. A major species of 144 nts. was observed in the medulloblastoma RNAs and represents Hel-N2. In addition, the fetal brain mRNA contained a barely detectable band representing the Hel-N2 band. In all of these experiments, an internal control oligonucleotide representing the U1snRNP-70K protein demonstrated the integrity and relative sampling of the RNA (lower panel).

From several experiments, the ratio of Hel-N1 to Hel-N2 in medulloblastoma cells D283 and D341 was calculated to be 1:14 and 1:3, respectively. Although the RT-PCR is not highly quantitative, the combined results of Western blotting, cDNA cloning and RT-PCR indicated that Hel-N2 is the predominant form of this protein in medulloblastoma cells. Hel-N2 lacks a small fragment present in Hel-N1

Figure 9:
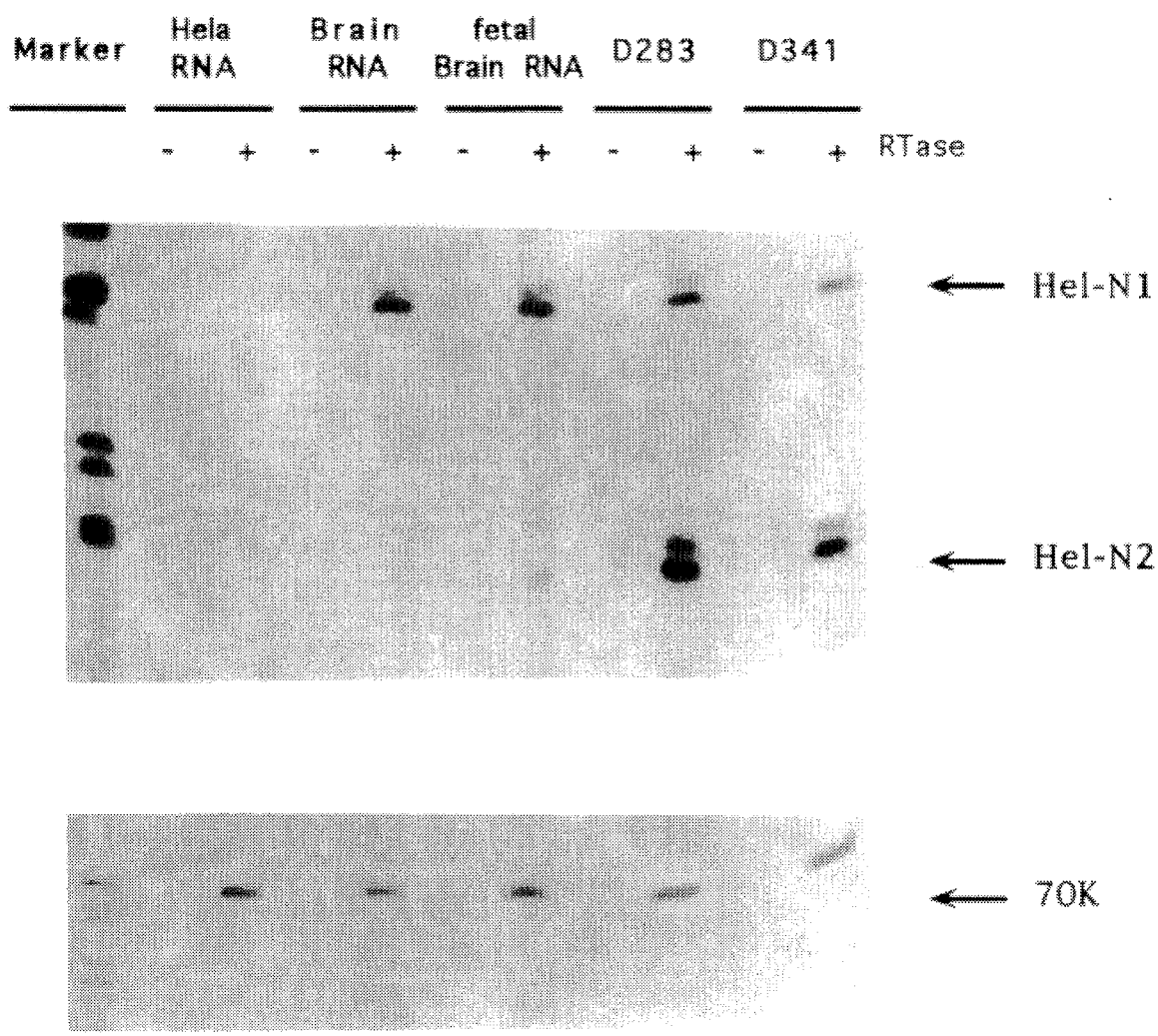
FIG. 9 is the expression pattern of Hel-N1 and Hel-N2 using reverse transcription-PCR of human brain, fetal brain and medulloblastoma cell messenger RNA. Hela RNA was used as a negative control. All reactions were performed in the presence (+) or absence (−) of reverse transcriptase. Upper panel: two Hel-N1 specific oligonucleotide primers spanning the region between RRMs 2 and 3 (T. D. Levine et al, *Mol. Cell Biol.* 13: 3494 (1993); P. H. King et al, *J. Neurosci.*, in press, and D. E. Tsai et al, *Nuc. Acids Res.* 19: 4931 (1991)) were used to detect variations in this region. The larger band corresponds to Hel-N1 mRNA, the smaller band corresponds to Hel-N2 mRNA (see FIG. 10). Lower panel: internal control RT-PCR products using the identical RNA samples and oligonucleotides specific for the U1snRNP-70K protein (C. Query et al, *Cell* 57:89 (1989)) to indicate the quality and relative quantity of the RNA preparations.
Figure 10:
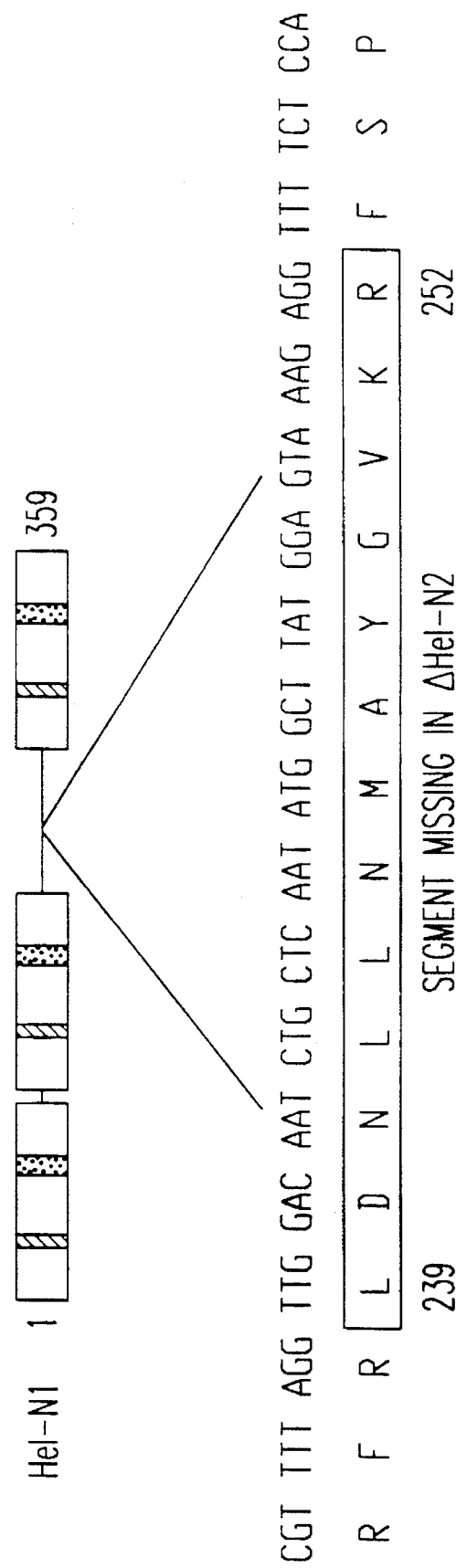
FIG. 10 is a diagram representing the basic structure of Hel-N1 and Hel-N2 (also known as ΔHel-N1), the deleted form of Hel-N1 present in human medulloblastoma cells. RRMs are represented by three open boxes in which shaded regions represent RNP1 and RNP2 (D. J. Kenan et al, *Trends in Biochem. Sci.* 16: 214 (1991)). Partial amino acid and nucleotide sequences between the second and the third RRM representing the differences between Hel-N1 and Hel-N2 are shown. The boxed region at the bottom indicates the 13 amino acid segment missing in Hel-N2. Numbers indicate the amino acid positions of the 13 amino acid segment present in Hel-N1.

Using oligonucleotides representing the terminal flanking sequences of Hel-N1, cDNA clones representing the Hel-N1 and Hel-N2 bands shown in FIG. 9 were obtained. The smaller form may represent an alternatively spliced form of Hel-N1 missing 39 nts. which encode 13 amino acids in HelN1 as shown in FIG. 10. The significance of this deleted form is not known, but it is likely that it is the band detected by the rabbit antibody in the cytoplasm in FIG. 8. From several experiments under a variety of conditions and cell types, including COS cell transfections, it was evident that both Hel-N1 and Hel-N2 appeared to be predominantly cytoplasmic.

RNA binding specificity of Hel-N2

The RNA recognition specificity of RRM proteins, including Hel-N1 has been determined by using RNA binding and selection from degenerate pools of randomized RNA. To examine the RNA binding specificity of Hel-N2, a high stringency selection protocol was used, that involved washing with high salt and urea (FIG. 11). High stringency binding is expected to yield only high affinity RNA ligands, whereas lower affinity selection like that used previously for Hel-N1 yields a broader collection of potential binding sites (T. D. Levine et al, *Mol. Cell Biol.* 13: 3494 (1993); P. H. King et al, *J. Neurosci.*, in press). A recognition consensus sequence for binding by both Hel-N2 and Hel-N1 is shown in FIG. 11 which indicates a strong match with the short uridylate sequences known to reside in the 3' UTR regions of proto-oncogene and cytokine mRNAs. These data demonstrate that the RNA binding specificity of Hel-N2 and Hel-N1 are indistinguishable and both are consistent with the previous findings implicating Hel-N1 in recognition of these proto-oncogene and cytokine mRNA 3' UTR sequences (T. D. Levine et al, *Mol. Cell Biol.* 13: 3494 (1993); P. H. King et al, *J. Neurosci.*, in press). Identification of mRNA-binding targets for Hel-N1 and Hel-N2

Medulloblastoma cells were subjected to standard RNP immunoprecipitation methods used to study various small nuclear RNPs (M. Lerner et al, *Proc. Natl. Acad. Sci. USA* 76: 5495 (1979); M. G. Kurilla et al, *Cell* 34: 837 (1983); C. Query et al, *Cell* 57:89 (1989)). Cell extracts were combined with rabbit anti-Hel-N1 antibodies and immunoprecipitated with Staph A Sepharose beads with repeated washing. Washed pellets were phenol extracted and the bound RNAs recovered by ethanol precipitation. Hel-N1 and Hel-N2 bound mRNAs were reverse transcribed using oligo dT, tailed with oligo dC at the 5' end and recovered by PCR.

Figure 12:
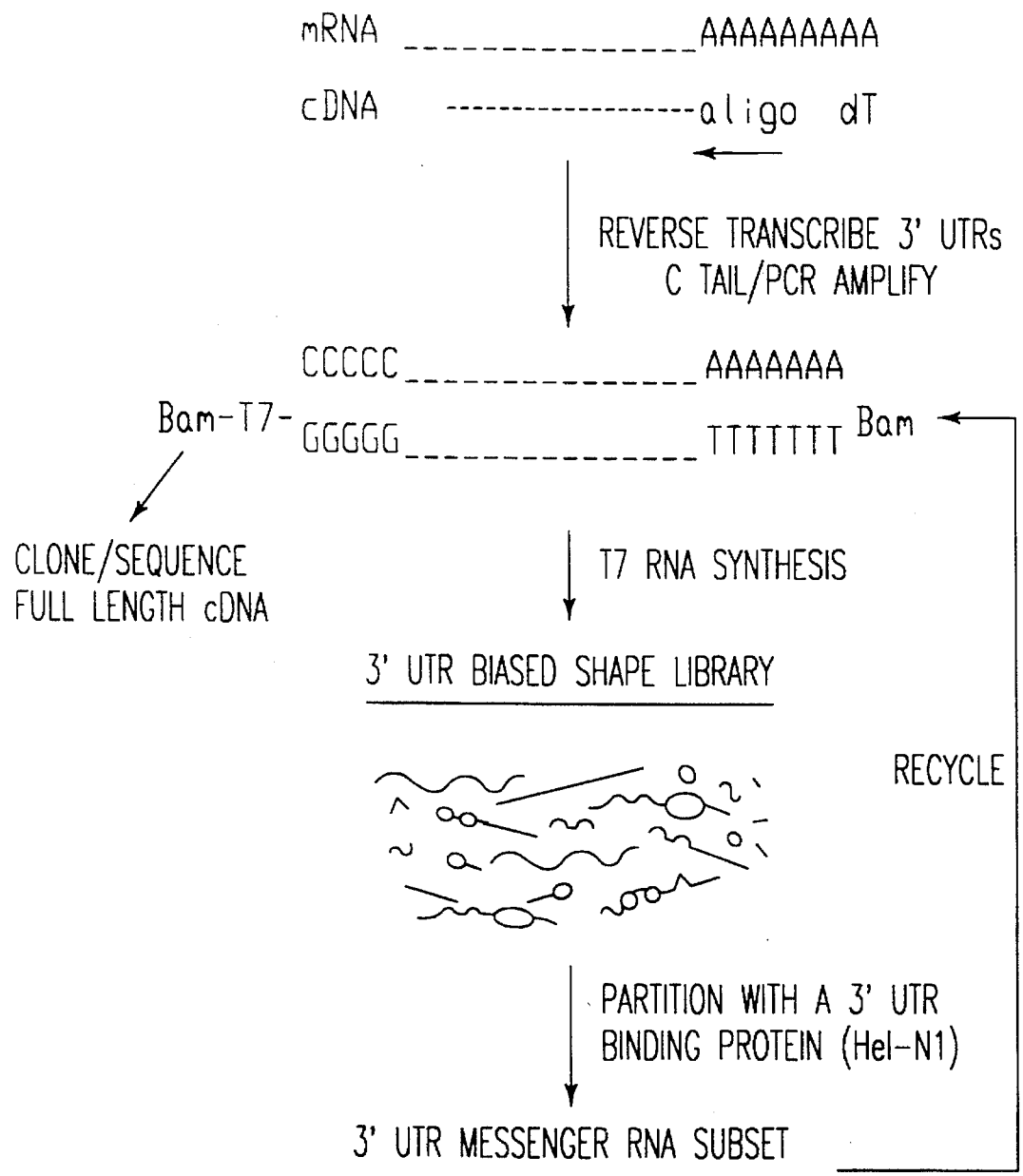
FIG. 12 shows an outline for the procedure to partition messenger RNA subsets using a 3' UTR shape library.

The cDNA-subset library was prepared according to the outline shown in FIG. 12. A key step which distinguishes this approach is the inclusion of a T7 polymerase promoter sequence next to the oligo G PCR primer. This allows resynthesis of the mRNA target sequences from the cDNA subset library which is a key step for recycling the mRNA/Hel-N1 binding reaction to assure specificity of target recognition. In addition, the ability to use repeated cycles of binding and rebinding of the mRNA subset allows the stringency of the binding to be varied such that the subset population is larger or smaller. Stringency is higher (smaller subset population) when using 0.5M NaCl and/or 0.5M urea in one of the binding cycles. The cDNA sequences in the subset library can be determined using any standard DNA sequencing procedure, thus yielding the desired Hel-N1 targets.

Messenger RNAs selected to bind Hel-N1 in vitro

Direct in vitro mRNA binding methods similar to those described above and by Levine et al. who used c-myc, c-fos, Id and GM-CSF 3' UTRs (T. D. Levine et al, *Mol. Cell Biol.* 13: 3494 (1993); P. H. King et al, *J. Neurosci.*, in press) were used here.

Two different sources of mRNA have proved feasible. In one case, total cell mRNA is bound to Hel-N1, the subset of bound mRNAs partitioned and the cDNA library prepared as described above for the medulloblastoma immunoprecipitation experiment. In the other approach, the cDNA library was prepared first using a PCR primer containing a T7 promoter (FIG. 12). The production of synthetic RNA improved the abundancy of mRNA for the preparation of the cDNA subset library. Sequences so derived are listed in Table II.

TABLE II

Growth Regulatory Protein (GRP) cDNAs isolated from human brain mRNA using Hel-N1

GRP-7: (SEQ ID NO: 81)
CCGTTCCATGAGCCACTCAATATCCTTCCAAATAATTTTTTCTAAGTTAACCATTCTTTTGTTTTCTAAGTTAACCATTCTTTTGTTTGTTTGAAAAAAAAAAAAAA

GRP-8: (SEQ ID NO: 82 (same as m-1 clone)
GGTAGGCAAAAAAGATATCGCAGGAAGGCCCTCCGTGATTCACTTCATATGTTTATGTATTGGTTGATTAATTAATTTTGTAATTTTAAAAAAAAAAAAAAAAAAAAA GRP-9: (SEQ ID NO: 83) (tyrosine kinase ACK)
CATTTTTCCCACCAGCCTGTTGGCGAAGTTGCTGCTCCGGCATTCAGTACCTGCTTCTCCTGTGAAATAAAGTTAGTTTCTATTTTATGTTAAAAAAAAAAAAAAA GRP-6: (SEQ ID NO: 84) (same as GRP-9)
CATGTTTTCCCACCAGCCTGTTGGCGAAGTTGCTGCTCCGGCATTCAGTACCTGCTTCCTGTGAAATAAAGTTAGTTTCTATTTTATGTTAAAAAAAAAAAAAAA

GRP-1' (SEQ ID NO: 85)
GTTTTGTTGTTTTCTATTAAACTGCATAAAGAAACGGCAAAAAAAAAAAAAAAAAAA

GRP-16 (SEQ ID NO: 86)
GGCTGCCTTATAATTTTTGTCTCTTTCTTTCCCACCTTTAATTGTCAATGGTTAAAAAAATGCTGTTTTCTGATATAAATTTTTATTAGTGCATACCTTAAAAAAAAA

GRP-10' (SEQ ID NO: 87)
TATATGCGTTAATATTTCTTTCCATCTGTGATTGTTCTGTCACTTATTTTCTTTAATAAATGGGTTTCTGAAAAAAAAAAAAAAAAAAAA

GRP-24 (SEQ ID NO: 88)
TTCCATGCCCTGTTTTATTTTCTACTTTATTGCCCCTGTTCCCCAGGCACAAAGCTATGTGCTGACATACATTGGCTCTCAATAATACTGTCATATTTGAAAAAAAAAAAAAA

GRP-2: (SEQ ID NO: 89)
TTTTAATTTACATTTTTATTTATTTTGTAATTATGATTTGGGTTGGGAGGGGGGGCTACATTATAAACGCTTAGGAATTCGAGCTCGGTACCC

GRP-15' (SEQ ID NO: 90)
TATCAAATACCAAGTTTATTTCACAAACACTAGGAAGATGGGTTGAGGGTGGG

GRP-1: (SEQ ID NO: 91): (M-8)
ACAAATGGTAGGCAAAAAAAGATATCGCAGTAAGGCCCTCCGTGATTCACTTCATATGTTTATGTATTGGTTGAATTATTTATGTAAAAAAAAAAAAAA

GRP-2: (SEQ ID NO 92)
ATGTCTAACTTTTAATATGCTTGTTCAGCTCTCAATAAAGTAATAAAGCTTGGTTGTCAGTATAAAAAAAAAAAAAAAAAAA

GRP-3: (SEQ ID NO 93)
ATGAGCTTTACTCAATAAAGCTGGCTTTCCCTGCAAAAAAAAAAAAAAAAAAA

GRP-5 (SEQ ID NO 94)
CAAGGAGCATAAGAGATGTTCTCGTAGCTCGCGTTGTGTGAAATGTCCATCTTAGTTTTGTTAAAAAAAAAAAAAAAAAAAAAAA

GRP-8' (SEQ ID NO 95): (m-22)
CAATCCTGATGCAAGAGAGAAGCCAATGATGGCTCATTTCGAACTGTGTTATTATTAGGAAAAAAAAAAAAAA

GRP-7' (SEQ ID NO 96): (GRP-20)
TCTTGATCTTATGCAAGTACAAGACGTACTTTAAATTTTTGTTGTTATGAAAAAAAAAAAA

GRP-5' (SEQ ID NO 97)
ATGTCTTGATGTTATGCAGGAAGTACAGGAAGTACAGACATACTTTAAATTTGTTATGAAAAAAAAAAAAAAAAAAAA

GRP-14 (SEQ ID NO: 98)
ATGGACTATCAGAAATAGACAACACAGATTTGGGTCACAAAGCTGGCTCTGTATTTGCATTTATTTTGTGTCTTGTCAGTTTGGGAATGATTAATATTAAAAAAAAAAAAAA

GRP-14' (SEQ ID NO: 99)
AGGCAAAAAAGATATGCAGGAAGGCCCTCCGAGATTCACTTCACTTCATATGTTTATGTATTGGTTGAATTATTTTGTAATTTTAAAAAAAAAAAAAAAAAAAAAA

GRP-21 (SEQ ID NO: 100)
GTGCAGTGTACCACATTTTCTTTATCCAGTCTATCATTGATGGACATTAAAGGTTGATTGATGCAATAAAGGTTGCAAAAAAAAAAAAAAAA

GRP-23 (SEQ ID NO: 101):
AACCATTTCATATAATTTTATCATATACTGTATCTGCAAACTTTATGTCCTGCTTTCATAAGCATTAAAAAA

It is evident that all of the mRNA sequences recovered contained the characteristic short stretches of uridylates found in the random RNA selection experiments (FIG. 11 and Shaw & Kamen, 1986, ibid). In many cases, these sequences were near the poly A stretch, but in each case they were within the 3' UTR because the experiments were designed to bias for sequences near the 3' end (termed 3' UTR shape library). From among a collection of fifty cDNA 3' UTR sequences obtained, approximately ten percent were recognizable in the nucleic acid sequence databases. In every case, these previously known cDNAs represented growth regulatory proteins including, the ACK nonreceptor tyrosine kinase (which was found twice), the SYN (src/yes-type) proto-oncoprotein, and the BTG1 (P3/P4/interferon related) growth regulatory protein. (The human ACK non receptor tyrosine kinase as described in E. Manser et al, *Nature* 363: 364 (1993); the BTG1 representing the family of PC 3 and PC 4, lymphokine-related proteins involved in neuronal differentiation and antiproliferation, see: J. P. Rouault et al, *EMBO J.* 11:1663 (1992); A. Bradbury et al, *Proc. Natl. Acad. Sci. USA* 88: 3353 (1991); F. Tirone et al, *Proc. Natl. Acad. Sci. USA* 86: 2088 (1989); the yes and src-related protooncogene syn, which is a non-receptor tyrosine kinase described in K. Semba et al, *Proc. Natl. Acad. Sci. USA* 83: 459 (1986)). In the binding experiments shown in Table II, no housekeeping genes or non-growth related genes were detected. This is in stark contrast to the random cDNA sequencing experiments of Venter and coworkers in which they used the same brain mRNA source (M. D. Adams et al, Nature 355: 632 (1992)). Out of 2,375 cDNA clones, 15% of those obtained by Venter (348) were recognizable in the database. Among the cDNAs of Venter, only five were evident as growth regulatory proteins. Thus, while fewer than 2% of the cDNAs revealed by random sequencing were growth related protooncogene proteins, 100% of the known Hel-N1-derived cDNAs found using the present invention were implicated in tightly regulated functions, signal transduction or growth related pathways.

These findings demonstrate that Hel-N1 can provide access to a nested set of cDNAs and their cognate genes because of its ability to recognize and bind to 3' UTR sequences. The only recognizable common characteristics among these cDNAs is their 3' UTR binding sites (short stretches of uridylates) and their demonstrated functions as growth regulatory proteins. Therefore, the probability is very high that the 85 to 90% of unidentified cDNAs revealed by this screening procedure represent novel growth regulatory genes which contain similar 3' UTR binding signals. In the experiment of Table II, total brain mRNA was used, but mRNA from any differentiated tissue or cell type, including immune cells or tumors, can be used for this growth regulatory mRNA selection procedure with Hel-N1 and similar proteins. Also, it is likely that additional multitarget RNA binding proteins will be discovered that provide access to other structurally and functionally related subsets of messenger RNA. These also could potentially represent unified growth regulatory pathways or circuits which are encoded by distinct constellations of cytoplasmic mRNAs.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for obtaining a cDNA library having members encoding a group of structurally or functionally related proteins, from total cell mRNA comprising:

binding RNA representing total cell mRNA to an RNA-binding protein having specific binding to 3'-untranslated regions of a subset of said total cell mRNA, wherein said RNA-binding protein is Hel-N1 or Hel-N2;

preparing a cDNA library from the resulting bound products.

2. The method of claim 1, wherein said RNA-binding protein is Hel-N1.

3. The method of claim 1, wherein said RNA-binding protein is Hel-N2.

4. The method of claim 1, wherein said total cell mRNA is a member selected from the group consisting of human brain mRNA, plant mRNA and tumor cell mRNA.

5. The method of claim 1, further comprising expressing one or more members of said cDNA library to provide one or more proteins from a group of functionally related proteins.

6. The method of claim 5, wherein said group of functionally related proteins comprise growth regulatory proteins, proto-oncogenes, cytokines, lymphokines or anti-oncogene proteins.

7. The method of claim 6, wherein said group of functionally related proteins comprise growth regulatory proteins.

\* \* \* \* \*